US011690957B2

(12) United States Patent
Chuang et al.

(10) Patent No.: US 11,690,957 B2
(45) Date of Patent: Jul. 4, 2023

(54) SAFETY-ENHANCED NEEDLE-FREE INJECTOR

(71) Applicant: MIRACLE MANAGEMENT PTE LTD, Singapore (SG)

(72) Inventors: Ping Derg Chuang, Singapore (SG); David Samuel Leon Chuang, Singapore (SG)

(73) Assignee: MIRACLE MANAGEMENT PTE LTD, Singapore (SG)

( * ) Notice: Subject to any disclaimer, the term of this patent is extended or adjusted under 35 U.S.C. 154(b) by 395 days.

(21) Appl. No.: 16/346,374

(22) PCT Filed: Oct. 31, 2017

(86) PCT No.: PCT/SG2017/050546
§ 371 (c)(1),
(2) Date: Apr. 30, 2019

(87) PCT Pub. No.: WO2018/080402
PCT Pub. Date: May 3, 2018

(65) Prior Publication Data
US 2020/0046902 A1      Feb. 13, 2020

(30) Foreign Application Priority Data

Oct. 31, 2016   (SG) .......................... 10201609111W

(51) Int. Cl.
*A61M 5/30* (2006.01)
*A61M 5/20* (2006.01)
*A61M 5/24* (2006.01)

(52) U.S. Cl.
CPC ............ *A61M 5/30* (2013.01); *A61M 5/2053* (2013.01); *A61M 5/24* (2013.01); *A61M 2005/2013* (2013.01); *A61M 2205/3331* (2013.01)

(58) Field of Classification Search
CPC ........ A61M 5/30; A61M 5/2053; A61M 5/24; A61M 2005/2013; A61M 2205/3331;
(Continued)

(56) References Cited

U.S. PATENT DOCUMENTS 3,859,996 A      1/1975   Mizzy et al.
5,569,189 A  *  10/1996   Parsons ............... A61M 5/1782
                                                        604/22
(Continued)

FOREIGN PATENT DOCUMENTS

WO      WO-98-15307 A1     4/1998

OTHER PUBLICATIONS

International Search Report and Written Opinion issued in PCT/SG2017/050546, dated Mar. 22, 2018; ISA/EP.
(Continued)

*Primary Examiner* — Theodore J Stigell
(74) *Attorney, Agent, or Firm* — Harness, Dickey & Pierce PLC

(57) ABSTRACT

A method for needle-free injection and a needle-free injector device are provided. The method includes automatically injecting an injectable into a surface in contact with the needle-free injector in response to a skin compression parameter of an end of the needle-free injector. A needle-free injector device (102) includes predefined structures formed on it to inject an injectable through a non-porous material. The predefined structures engage an airlock mechanism such that an airlock in the non-porous material and operably coupled to the airlock mechanism can only be opened and closed to enable needle-free injection through the non-porous material without disrupting an integrity of the non-porous material by the needle-free injector device. Other functions, embodiments and methods for using and programming the needle-free injector device are also provided.

6 Claims, 47 Drawing Sheets

(58) Field of Classification Search
CPC ........ A61M 5/2033; A61M 2005/2418; A61M 2205/6045
See application file for complete search history.

(56) References Cited

U.S. PATENT DOCUMENTS

| | | |
|---|---|---|
| 8,617,099 B2 | 12/2013 | Williamson |
| 8,740,838 B2 | 6/2014 | Hemond et al. |
| 2009/0292240 A1* | 11/2009 | KraMer .................. A61M 5/19 604/82 |
| 2013/0150820 A1 | 6/2013 | Cappello et al. |

OTHER PUBLICATIONS

International Preliminary Report on Patentability (Chapter II) issued in PCT/SG2017/050546, Date of Completion of Report: Apr. 9, 2019; IPEA/ EP.
Australian Examination Report for corresponding Application No. 2017352017 dated Jun. 16, 2022.
European Communication for Application No. 17798015.8-1122, dated Dec. 14, 2022 (7 Pages).

* cited by examiner

☐ Start Position
■ End Position
↖ Path

Legend

2100

2110

2120

2130

2140

2150

2160

2640

2650

SAFETY-ENHANCED NEEDLE-FREE INJECTOR

CROSS REFERENCE TO RELATED APPLICATIONS

This application is a U.S. National Phase Application under 35 U.S.C. 371 of International Application No. PCT/SG2017/050546 filed on Oct. 31, 2017, which claims the benefit of priority from Singapore Patent Application No. 10201609111W filed Oct. 31, 2016. The entire disclosures of all of the above applications are incorporated herein by reference.

TECHNICAL FIELD

The present invention generally relates to systems and devices for needle-free injection, and more particularly relates to systems and devices for safety-enhanced needle-free injection and/or needle-free injection through both a porous and a non-porous material.

BACKGROUND OF THE DISCLOSURE

Needle-free injectors are used to provide needle-free injections through skin to intra-dermal, subcutaneous and, sometimes, intra-muscular regions under the skin. However, conventional needle-free injectors have many flaws. First, needle-free injectors are susceptible to leakage at the injection site. A person must be taught the minimum skin pressure to prevent leakage, which usually results in a large safety margin to prevent a leaky injection. This is particularly problematic if the person's tactile sensors are dulled by wearing heavy gloves or numb from cold, or when the surface pressure is difficult to feel because of an unwieldy injector design.

Some conventional needle-free injectors attempt to overcome this leakage issue by incorporating a close loop mechanical sensor at a single pre-determined surface pressure setting. Human experience is needed to regulate this pressure setting as circumstances change because, whereas a skilled human sensor knows what to do, a different human sensor has to be taught this skill to differentiate the pressure settings for different skin surfaces such as for a cow, a grown chicken or a young chick so as not to injure or kill the subject. Also, soft human tissue on the face or sensitive human tissue on the penis or vagina or delicate tissues of internal organs require an extensive learning process to acquire these skills.

U.S. Pat. No. 8,740,838 to Hemond of MIT describes an electrical close loop servo-controlled computerized device, the sensors primarily relating to the propulsion of the injectable fluid at the point of injection and during the course of an injection. However, the injector sensors are not configured to sense skin properties at a time prior to the injection, say t−n seconds, where t is the time of injection and n is the time prior to the injection and prior to deformation of an ampoule and prior to propulsion pressure (for example, t−1 second or t−1 ms). In addition, the forces utilized for the Hemond needle-free injection system require hard materials designed to be impact resistant so as to contain the high pressures of a jet stream which may go up to 250 Newton, while pressure against the skin for injection is differentiated in tens of gram force.

Conventional needle-free injection systems also assume proper delivery of the injectable and typically do not provide a safety solution if an injector with excessive pressure is used with the ampoule, or when one or more orifices of a multiple orifice ampoule are blocked. Some conventional injectors provide for over pressure safety by intentionally weakening the barrel of an ampoule. If an excessively powered injector is accidentally used with the ampoule, or if one or more multi-orifice holes are blocked by the medication, the excess pressure will cause the wall to distort from over pressurization and leak the injectable or cause dangerous fragmentation.

Further, in a setting where electrical devices coupled to the injectors or operating as a part of the injector system are either incompatible or wieldy, there is no way for protecting or personalizing the injector or, when use with external devices is desired (e.g., robotic surgery), for the injector to communicate with such external devices.

Thus, what is needed is a method, system and device for needle-free injection which addresses the problems of prior art devices and systems and provides a safety-enhanced needle-free injection system with robust non-electrically-enabled protection and communication capabilities. In addition, a method and system for needle-free injecting a subject through a non-porous material is needed. Furthermore, other desirable features and characteristics will become apparent from the subsequent detailed description and the appended claims, taken in conjunction with the accompanying drawings and this background of the disclosure.

SUMMARY

According to at least one embodiment of the present invention, a safety-enhanced needle-free injector system is provided. The safety-enhanced needle-free injector system includes a housing, a bolt carrier, an ampoule and a user-sensible safety mechanism. The bolt carrier includes one or more springs held at a first end and a firing chamber formed therein from the one or more springs to an opening at a second end opposite the first end. The bolt carrier also includes a spring-driven member coupled to the one or more springs and located in the firing chamber. The ampoule is coupleable to the bolt carrier and includes a compartment for storing an injectable for needle-free delivery and a seal for driving the injectable out an opening at a first end of the ampoule. A plunger couples between the spring-driven member of the bolt carrier and the seal of the ampoule when a first end of the ampoule is coupled to the bolt carrier. The plunger allows the spring-driven member to engage the seal to drive the injectable along a length of the ampoule from the first end of the ampoule to a second end of the ampoule and out an opening at the second end of the ampoule, the opening comprising one or more orifices. The user-sensible safety mechanism includes a pressure-sensed, tactile-sensed or visual-sensed mechanism for preventing inadvertent user activation of the needle-free injector system to provide safety-enhanced needle-free injection of the injectable.

In accordance with another aspect of the present invention, a system for needle-free injection through a non-porous material is provided. The non-porous material has an airlock formed in it and the system includes an injector and an ampoule. The ampoule includes a compartment for storing the injectable for needle-free delivery and an injectable seal for driving the injectable out an opening at a first end of the ampoule. The ampoule couples to the injector at a second end of the ampoule to allow the injector to engage the injectable seal with a plunger for driving the injectable out the opening at the first end. The ampoule also includes one or more predefined structures formed at the first end of the ampoule and orthogonal to the length of the ampoule for engaging and forming an airtight seal with the airlock. The airlock determines whether to open and provide access through the non-porous material in response to firm airtight engagement between the ampoule and the airlock and in response to a number of and shapes of the one or more predefined structures.

In accordance with further aspect of the present invention, a method for needle-free injection through a non-porous material having an airlock is provided. The airlock is formed in the non-porous material and the method includes coupling an ampoule having a compartment for storing the injectable for needle-free delivery and an injectable seal for driving the injectable out an opening at a first end of the ampoule to a needle-free injector at a second end of the ampoule to allow the injector to engage the injectable seal for driving the injectable out the opening at the first end. The method also includes coupling the ampoule to the airlock to engage and form an airtight seal with the airlock in response to interactive coupling of one or more predefined structures formed at the first end of the ampoule and orthogonal to the length of the ampoule with the airlock, and includes determining whether to open and provide access through the non-porous material in response to firm airtight engagement between the ampoule and the airlock and in response to a number of and shapes of the one or more predefined structures.

In accordance with yet another aspect of the present invention, a leak-resistant needle-free injector system is provided for injecting an injectable through a porous material. The system includes an injector, an ampoule and an orifice seal. The ampoule includes a barrel for storing the injectable for needle-free delivery and an injectable seal connectable to a plunger for ejecting the injectable out an opening comprising an orifice or orifices at a first end of the ampoule. The ampoule couples to the injector at a second end of the ampoule to allow the injector to engage the plunger to drive the injectable seal towards the first end to eject the injectable out the opening at the first end. The orifice seal engages the ampoule at the first end and is formed such that an opening in the orifice seal aligns with one or more orifices in the opening at the first end of the ampoule. The orifice seal includes a pliable compressible material for forming a firm leak-resistant seal with an injectable surface of the porous material during injection of the injectable into the surface of the porous material.

In accordance with a further aspect of the present invention, a needle-free injector system is provided. The needle-free injector system includes a housing, a bolt carrier and an ampoule. The bolt carrier includes one or more compression springs held at a first end and having a firing chamber formed therein from the one or more compression springs to an opening at a second end opposite the first end. The bolt carrier also includes a spring-driven member coupled to the one or more compression springs and located in the firing chamber. The ampoule couples to the bolt carrier and includes a compartment for storing an injectable for needle-free delivery and an injectable seal for driving the injectable out an opening at a first end of the ampoule. The injectable seal couples to the spring-driven member via a plunger and a plunger pad when a second end of the ampoule is coupled to the bolt carrier to allow the spring-driven member to engage the injectable seal for driving the injectable seal along a length of the ampoule from the second end of the ampoule to a first end of the ampoule to eject the injectable out the opening at the second end of the ampoule, the opening at the second end of the ampoule comprising one or more orifices. The ampoule also has one or more ampoule predefined structures formed at the second end of the ampoule and formed at an angle to a central longwise axis of the ampoule for physically inhibiting coupling of the ampoule to the bolt carrier when the one or more ampoule predefined structures do not match up to corresponding injector predefined structures formed on a plug on the second end of the bolt carrier.

In accordance with an additional aspect of the present invention, a finite state machine mechanical computer (FSMMC) is provided. The FSMMC includes two or more devices, each of the two or more devices having a predefined structure formed at a surface thereof. A first predefined structure mechanically interactively couples with a second predefined structure such that a predetermined series of movements of a corresponding first device in relation to a corresponding second device defines one of a plurality of functions of the FSMMC, the predetermined series of movements corresponding to one of a plurality of predefined constrained sequence of movements defined by the mechanically interactive coupling of the first predefined structure with the second predefined structure to change the FSMMC from a first finite state to a second finite state.

In accordance with another aspect of the present invention, a modal logic physical system is provided. The modal logic system includes two or more devices, each of the two or more devices having a predefined structure formed at a surface thereof. A first predefined structure mechanically interactively couples with a second predefined structure such that a predetermined series of movements of a corresponding first device in relation to a corresponding second device defines one of a plurality of functions of the modal mechanical device, the predetermined series of movements corresponding to one of a plurality of predefined constrained sequence of movements defined by the mechanically interactive coupling of the first predefined structure with the second predefined structure to change from a first modal logic to a second modal logic.

In accordance with yet another aspect of the present invention, a needle-free injection system is provided. The needle-free injection system includes a needle-free injector, an ampoule and a restraining device. The ampoule couples to the needle-free injector at a first end of the ampoule and has a compartment for storing an injectable for needle-free delivery. The ampoule also includes an injectable seal cooperatively coupled to a plunger for driving the injectable out an opening at a second end of the ampoule, the plunger coupling to the needle-free injector to allow driving of the plunger along a length of the ampoule from the first end to the second end to eject the injectable out an opening at the second end of the ampoule. The restraining device couples to the needle-free injector and extends beyond the opening at the second end of ampoule and includes mechanical means to provide back-pressure support for the needle-free injection system.

In accordance with a further aspect of the present invention, an injector restraining accessory device is provided. The injector restraining accessory device includes a first member and a second member. The first member couples to an injector for facilitating handling and use of the injector during injection of an injectable. The second member couples to the first member for providing back-pressure support for the injector during injection of the injectable.

In accordance with yet an even further aspect of the present invention, a system for programming a finite state machine mechanical computer (FSMMC) is provided. The system for programming the FSMMC includes a computing device, a communication network and a structure inscribing device. The computing device generates information for defining FSMMC structures. The communication network is coupled to the computing device and transmits the information through the communication network. The structure inscribing device is coupled to the communication network and inscribes a first predefined structure on a first device in response to the information, the first predefined structure mechanically interactively coupleable to a second predefined structure on a second device such that a predetermined series of movements of the first device in relation to the second device defines one of a plurality of FSMMC functions. The predetermined series of movements corresponds to one of a plurality of predefined constrained sequence of movements defined by the mechanically interactive coupling of the first predefined structure with the second predefined structure to change a FSMMC finite state of a FSMMC defined by the first and second devices.

In accordance with yet an additional aspect of the present invention, a method for personalizing an apparatus in accordance with a PING Replicator system is provided. The apparatus includes at least a first device and a second device and the method includes receiving information for defining finite state machine mechanical computer (FSMMC) structures; and inscribing first predefined structures on the first device in response to the information. The first predefined structures mechanically interactively couple to second predefined structures on the second device such that a predetermined series of movements of the first device in relation to the second device defines one of a plurality of FSMMC functions. The predetermined series of movements correspond to one of a plurality of predefined constrained sequence of movements defined by the mechanically interactive coupling of one or more of the first predefined structures with one or more of the second predefined structure to change a FSMMC finite state of a FSMMC defined by the first and second devices.

In accordance with a further aspect of the present invention, a system for providing injectable treatment is provided. The system includes a programmable needle-free injector for needle-free injecting injectable and a device which couples to the programmable needle-free injector. The programmable needle-free injector injects a programmed number of doses of the injectable at a programmed injection pressure and in a programmed injection amount. The device couples to the programmable needle-free injector to program a treatment regimen. The treatment regimen includes one or more of the programmed number of doses of the injectable medication, the programmed injection pressures and the programmed injection amounts to provide a user first time success treatment regimen.

In accordance with another aspect of the present invention, a method for needle-free injection through a non-porous material is provided. The non-porous material has an airlock formed in it to allow access through the non-porous material from a first side of the non-porous material to a second side of the non-porous material. The airlock includes an airlock adaptor with a sealable channel to control access through the non-porous material, the sealable channel including an outer chamber and an inner chamber. The airlock also includes a first portion protruding from the first side of the non-porous material which includes the outer chamber and a second portion protruding from the second side of the non-porous material which includes the inner chamber. The method includes inserting a needle-free injector device having predefined structures formed at one end into an outer chamber of the airlock adaptor until it reaches an engagement position within the outer chamber for the predefined structures to engage the airlock adaptor and moving a part or parts of the needle-free injector device, a part or parts of at least a portion of the airlock adaptor or part or parts of both the needle-free injector device and the at least a portion of the airlock adaptor in a predetermined manner while engaged to open the channel. The method also includes inserting the needle-free injector device into the opened channel so that at least a portion of the needle-free injector device passes through the airlock to the second side of the non-porous material and injecting an injectable in at least a portion of the needle-free injector device into a surface on the second side of the non-porous material, the injectable injected into the surface from an orifice formed at an end of the at least a portion of the needle-free injector device which contacts the surface.

In accordance with a further aspect of the present invention, a needle-free injector device is provided. The needle-free injector device includes predefined structures formed on it to engage an airlock mechanism such that an airlock in a non-porous material and operably coupled to the airlock mechanism can only be opened and closed to enable needle-free injection through the non-porous material without disrupting an integrity of the non-porous material by the needle-free injector device.

In accordance with another aspect of the present invention, a needle-free injection system is provided. The needle-free injection system includes an injector and an ampoule. The ampoule includes predefined structures formed thereon in a manner such that only the ampoule is required to disassemble the injector into its component parts. The ampoule disassembles the injector by operably coupling the predefined structures on the ampoule to predefined structures formed on the injector and performing one or more predetermined movements of the ampoule and the injector in relation to one another.

In accordance with a further aspect of the present invention, a system for reloading a needle-free injector is provided. The needle-free injector includes a housing and a bolt carrier with one or more compression springs. The system includes a cable, a reset chamber and a reloader. The reset chamber couples to the housing and includes a slide movably coupled to a reloading pin at one end and coupled to the cable at a second end, the reloading pin coupling to the one or more compression springs during reloading. The reloader couples to the cable for sliding the slide within the reset chamber when coupled to the housing to compress the one or more compression springs.

In accordance with yet another aspect of the present invention, a method for needle-free injection is provided. The method includes automatically injecting an injectable in at least a portion of a needle-free injector device into a surface in contact with the needle-free injector in response to either a contact surface pressure an end of the needle-free injector against the surface or a skin compression parameter of an end of the needle-free injector against the surface.

In accordance with yet a further aspect of the present invention, a motion compensating needle-free injection system is provided. The system includes a housing and a bolt carrier. The bolt carrier includes one or more compression springs held at a first end and a firing chamber formed therein from the one or more compression springs to an opening at a second end opposite the first end. The bolt carrier also includes a spring-driven member coupled to the one or more compression springs and located in the firing chamber. And the bolt carrier includes a relocatable firing ring coupled to a pressure sensing spring for automatically firing the bolt carrier in response to a sensed surface pressure of the needle-free injection system against an injection surface exceeding a predetermined surface pressure threshold. Relocating the relocatable firing ring adjusts one or both of time of firing or distance of firing, the time of firing corresponding to the predetermined surface pressure threshold and the distance of firing corresponding to a stroke of the spring-driven member.

In accordance with an additional aspect of the present invention a pre-programmable limited use triggerable firing system is provided. The system includes a housing, a firing member and a limited use control device. The firing member includes one or more compression springs held at a first end and having a firing chamber formed therein from the one or more compression springs to an opening at a second end opposite the first end. The firing member also includes a spring-driven member coupled to the one or more compression springs and located in the firing chamber for traversing the firing chamber in response to triggering decompression of the one or more compression springs. The limited use control device physically inhibits use of the firing member after a predetermined number of uses, each use comprising one triggering.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment. The illustrations and descriptions in this document cover numerous components that come in various sizes and shapes. These illustrations and descriptions are not necessarily to scale, and some components or parts of components are intentionally magnified or reduced to give clarity to the fine details.

FIG. 1, comprising FIG. 1A and FIG. 1B, depicts needle-free injectors in accordance with a present embodiment and functional operation thereof, wherein FIG. 1A depicts perspective views of two needle-free injectors in accordance with the present embodiment and FIG. 1B depicts planar views of functional operation of either of the two needle-free injectors of FIG. 1A.

FIG. 2, comprising FIGS. 2A and 2B, depict views of ampoule safety solutions in accordance with the present embodiment, wherein FIG. 2A illustrates a perspective view of a user-fillable seal and plunger ampoule and FIG. 2B illustrates side and top planar views of both the user-fillable seal and plunger ampoule and a factory prefillable ampoule module containing a seal and plunger ampoule.

FIG. 3, comprising FIGS. 3A and 3B, also depict views of ampoule safety solutions in accordance with the present embodiment, wherein

FIG. 4, comprising FIGS. 4A, 4B, 4C, 4D and 4E, depict views of front seals of the ampoule in accordance with various aspects of the present embodiment, wherein FIG. 4A depicts perspective and planar views of various front seals, FIG. 4B depicts a perspective view of a front seal extending above and beyond an edge of the ampoule's orifice, FIG. 4C depicts a perspective view of multiple detachable front seals, FIG. 4D depicts planar views of a detachable multi-groove front seal, and FIG. 4E depicts planar views of a detachable screw-threaded front seal.

FIG. 6, comprising FIGS. 6A and 6B, depicts perspective and side and top planar views of key code systems for ampoules and injectors in accordance with the present embodiment, wherein FIG. 6A depicts perspective views of the key codes systems of the ampoules and the injectors and FIG. 6B depicts side and planar views of the ampoules with the key code systems including two-sprocket key codes and a special null key code.

FIG. 16, comprising FIGS. 16A, 16b, 16C and 16D, depicts views of a password feature in accordance with the present embodiment, wherein FIG. 16A depicts a diagram of pathways for a simple password, FIG. 16B depicts a diagram of a complicated password, FIG. 16C depicts a diagram of a maze of pathways for the complex password, and FIG. 16D depicts a perspective view of a password key.

FIG. 17, comprising FIG. 17B is a transparent perspective view of a rear end of the injector with the arithmetic ring with a stop at four count, FIGS. 17C and 17D are top planar view of the rear end of the housing with a window to view the arithmetic ring setting, and FIG. 17E is a top planar view of a multiple count arithmetic ring with gated rotation allowing multiple incremental counts.

FIG. 18, comprising FIGS. 18A, 18B, 18C, 18D, 18E, 18F, 18G and 18H, depicts various pathways for FSMMC operation in accordance with the present embodiment, wherein FIG. 18A depicts pathways for a conditional branch operation, FIG. 18B depicts pathways for a stop at two operation, FIG. 18C depicts angular pathways, FIG. 18D depicts a one-way pathway and a stop pathway, FIG. 18E depicts a curved pathway, FIG. 18F depicts an alternate angular pathway, FIG. 18G depicts a screw pathway, and FIG. 18H depicts a combinatory pathway.

FIG. 19, comprising FIGS. 19A, 19B, 19C, 19D and 19E, depicts various pathways for FSMMC logic, arithmetic and memory operations in accordance with the present embodiment, wherein FIG. 19A depicts pathways for a logic AND operation, FIG. 19B depicts pathways for a logic OR operation, FIGS. 19C and 19D depict a memory such as a Flip Flop or SRAM, FIG. 19E depicts a LEFT SHIFT MULTIPLY operation.

FIG. 20, comprising FIGS. 20A, 20B, 20C and 20D, depicts perspective views of restraining adaptors for use with the needle-free injection system in accordance with the present embodiment, wherein FIG. 20A illustrates a restraining adaptor, FIG. 20B illustrates the restraining adaptor with a hook and a hook cushion, FIG. 20C illustrates the restraining adaptor with a pincher and a step edge aid, and FIG. 20D illustrates the restraining adaptor with a long flat restraint.

FIG. 21, comprising FIGS. 21A, 21B, 21C, 21D, 21E, 21F and 21G, depicts perspective views of orthogonal, horizontal and skew angle use of the restraining adaptors of FIG. 20 in accordance with the present embodiment, wherein FIG. 21A depicts use of the restraining adaptor with the hook restraint for hydroporation treatment, FIG. 21B depicts use of the restraining adaptor with the hook restraint for hydroporation treatment of crow's feet, FIG. 21C depicts use of the restraining adaptor with the pincher and step edge aid for treatment of crow's feet, FIG. 21D depicts use of the restraining adaptor for treatment of erectile dysfunction, FIG. 21E depicts use of the restraining adaptor for treatment of Dupuytren's Contracture, FIG. 21F depicts use of the restraining adaptor for intra-cavity treatment, and FIG. 21G depicts use of the restraining adaptor with the pincher and step edge aid for horizontal intradermal of Langerhans cells.

FIG. 22, comprising FIGS. 22A, 22B, 22C and 22D, depicts magnified views of the injector with pinching restrainer assembly during operation in accordance with the present embodiment, wherein FIG. 22A is a cross-sectional planar view of a pincher and a step-edge aid during injection, FIG. 22B is a bottom left front perspective view the pincher, the step-edge aid and the ampoule orifice, FIG. 22C is a planar view of a subcutaneous tissue jet injection, and FIG. 22D is a planar view of an intradermal tissue jet injection.

FIG. 24, comprising FIGS. 24A, 24B and 24C, is planar and perspective views of the injector, a reset chamber and in-situ reloaders in accordance with the present embodiment, wherein FIG. 24A illustrates the injector and reset chamber at various stages of reloading, FIG. 24B depicts the foot pedal reloader, and FIG. 24C depicts the throttle reloader.

FIG. 26, comprising FIGS. 26A, 26B, 26C and 26D, depicts illustrations of a PING Replicator System in accordance with the present embodiment, wherein FIG. 26A illustrates the PING Replicator System, FIG. 26B illustrates the programmability of a needle-free injector using the PING Replicator System, FIG. 26C illustrates needle-free injector system parts manufacturable by the PING Replicator System, and FIG. 26D depicts input and output devices for the needle-free injector system.

FIG. 29, comprising FIGS. 29A, 29B and 29C, is an exploded perspective parts view with reference numerals of the airlock adaptor of FIG. 28 in accordance with the present embodiment, wherein FIG. 29A depicts a perspective view and an exploded parts perspective view of the airlock adaptor, FIG. 29B depicts a planar view and a perspective view of the outside of the airlock adaptor in the open and closed states, and FIG. 29C depicts a perspective view of the inside of the airlock adaptor in the closed position and a cutaway perspective view of the inside of the airlock in the closed position.

FIG. 33, comprising FIGS. 33A, 33B and 33C, depicts perspective views illustrating alternative airlock adaptors in accordance with the present embodiment, wherein FIG. 33A depicts a ball valve adaptor, FIG. 33B depicts a rotating gate adaptor, and FIG. 33C depicts a sliding gate adaptor.

Skilled artisans will appreciate that elements in the figures are illustrated for simplicity and clarity and have not necessarily been depicted to scale or shown with all of the components for ease of illustration.

DETAILED DESCRIPTION

The following detailed description is merely exemplary in nature and is not intended to limit the invention or the application and uses of the invention. Furthermore, there is no intention to be bound by any theory presented in the preceding background or the following detailed description. It is the intent of the present embodiment to present systems and devices for safety-enhanced needle-free injection at injection surfaces of a subject or material. An injection "surface" means a porous surface into which the injection is made and can include skin of human or animals or other non-skin biological surfaces such as tissue, a surface of an internal organ or the bark of a tree (e.g., to kill fungi). While those skilled in the art of needle-free injection conventionally use "skin pressure" to mean a pressure of a jet stream ejected from a needle-free injector ampoule to penetrate the skin, in the present document this pressure is referred to as "jet stream pressure". In accordance with aspects of the present embodiment, the term "skin pressure" or "surface pressure" is used to indicate a pressure of the orifice end of the ampoule against a surface/skin and is used as a skin compression parameter for firing the needle-free injector.

In accordance with one aspect, a safety-enhanced needle-free injector for dermal injection at intra-dermal, subcutaneous and intra-muscular levels is presented. In accordance with another aspect, a method and system for needle-free injection through a non-porous material such as a spacesuit or a biohazard protection suit is presented. In accordance with yet another aspect, a finite state machine mechanical computer and method of operation, including application of such mechanical computer for enhancing safety of a needle-free injector and controlling use of the needle-free injector, is presented. In accordance with a further aspect, accessories for a needle-free injector, including various restrainers for needle-free injection in sensitive areas and reloaders for resetting a spring-loaded needle-free injector, and use of such accessories are presented. And, in accordance with yet a further aspect, a system and method for personalizing safety controls and/or operation of needle-free injectors is presented.

Figure 1A:
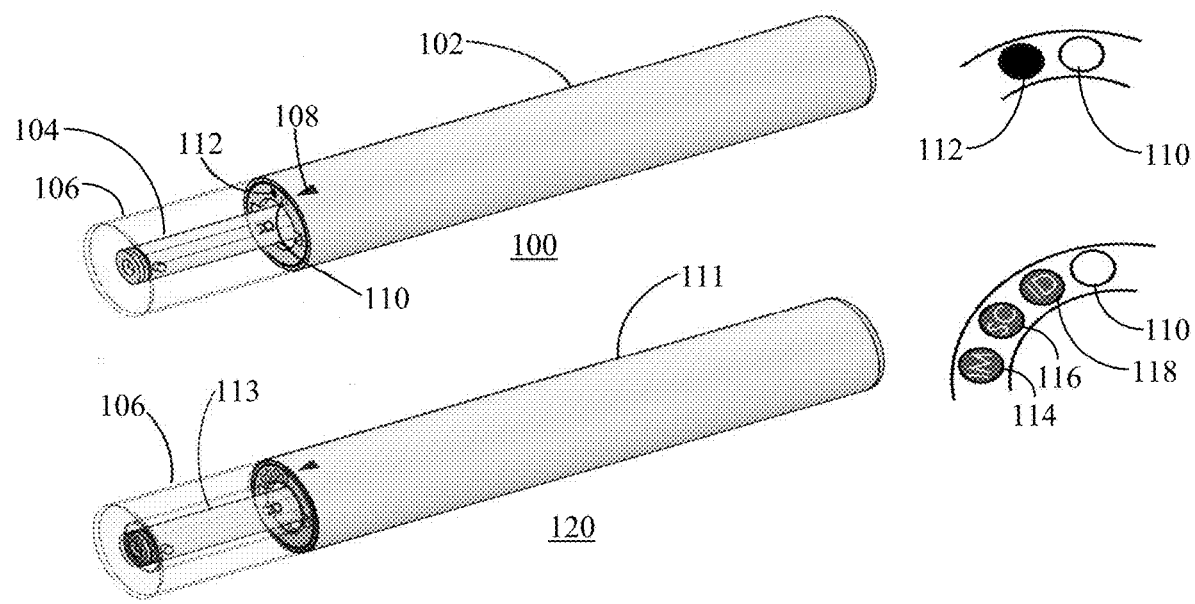

Referring to FIG. 1A, two perspective views 100, 120 depict a needle-free injector 102, an ampoule 104 and an ampoule cover 106 (in outline to see the ampoule 104 within) in accordance with a present embodiment. In the view 100, the ampoule 104 is a user-filled ampoule and the needle-free injector 102 has a single injection type configuration with a single surface pressure setting where rotating a status indicator 108 on the needle-free injector 102 from pointing to a "SAFE" indication 110 to pointing to an "ARM" indication 112 arms the needle-free injector 102.

In the view 120, a needle-free injector 111 is coupled to an ampoule module 113 and has a multiple injection type configuration with multiple surface pressure settings where the status indicator 108 on the needle-free injector 102 can be rotated from pointing to the "SAFE" indication 110 to pointing to an "IM ARM" indication (IM) 114 to arm the needle-free injector 102 for intra-muscular injections. Similarly, rotating the status indicator 108 from pointing to the "SAFE" indication 110 to pointing to a "SC ARM" indication (SC) 116 arms the needle-free injector 111 for subcutaneous injections and rotating the status indicator 108 from pointing to the "SAFE" indication 110 to pointing to an "ID ARM" indication (ID) 118 arms the needle-free injector 102 for intradermal injections. Those skilled in the art will realize that intra-muscular injections, subcutaneous injections and intradermal injections differ in the amount of pressure at which the medicine is ejected from the ampoule 104 by a plunger (not shown) within the needle-free injector 102.

Figure 1B:
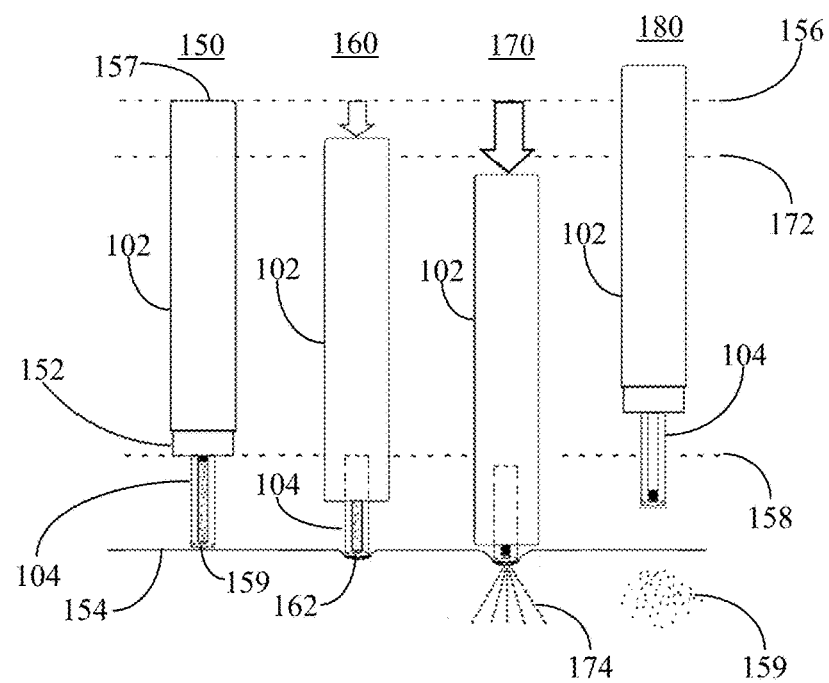

Referring to FIG. 1B, four planar views 150, 160, 170, 180 depict an exemplary functional operation of the needle-free injector 102. When the needle-free injector 102 is armed, a bolt carrier inside a housing of the needle-free injector 102 protrudes from an end of the housing displaying a colored protruding ring 152 on a protruding end of the bolt carrier, thereby providing a visual safety cue to the user that the needle-free injector 102 is armed. The user then places an end of the ampoule against skin 154 of a subject. At this point, the needle-free injector 102 extends from line 156 at an end 157 of the housing of the needle-free injector 102 to line 158 at the end of the colored protruding ring 152. The ampoule 104 includes injectable 159 for needle-free injection through the skin 154.

Referring to the view 160, the user depresses the needle-free injector 102 against the skin 154 where the ampoule 104 forms a dimple 162 in the skin 154 due to the skin pressure exerted by the needle-free injector 102. Between the view 160 and the view 170, the user exerts additional pressure on the needle-free injector against the skin 154. As the end 157 of the needle-free injector 102 passes line 172 indicating a desired trigger point, the skin pressure exceeds the threshold for firing the needle-free injector 102 thereby propelling a plunger through the ampoule 104 and ejecting a jet stream 174 of the injectable 159 into the subject through the skin 154. In view 180, as the user removes the needle-free injector 102 from the skin 154, the injectable 159 remains hypodermic.

Ampoule and the Ampoule Module

Conventional needle-free injectors assume proper delivery of the injectable and do not provide a safety solution if an injector with excessive pressure is used with an ampoule, or when one or more orifices of a multiple orifice ampoule are blocked. In accordance with the present embodiment, three designs for a safety solution are provided: a seal and plunger ampoule, an ampoule module containing a seal and plunger ampoule, and an ampoule module containing a seal only ampoule. Whereas the seal and plunger ampoule for user filled medication is sold empty, both ampoule modules are prefilled by the factory.

Figure 2A:
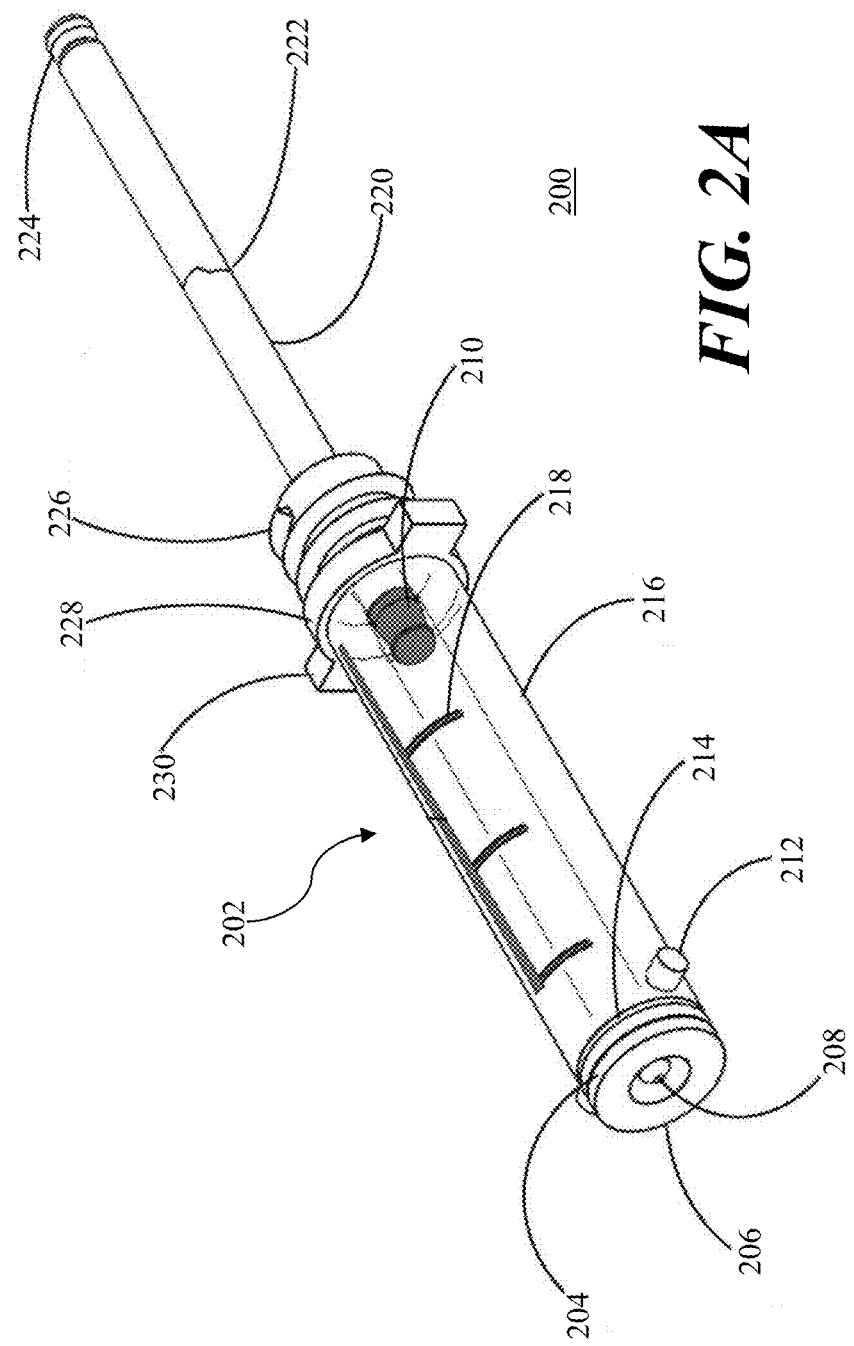

Referring to FIG. 2A, a perspective view 200 depicts a seal and plunger ampoule 202 which consists of a front seal 204, a front seal coating 206, an orifice 208 for the injectable to exit the ampoule when under impact pressure from a rear seal 210, sprockets 212 to lock onto another device, an over pressure safety ring 214, a barrel 216 to hold the injectable, a printed scale 218 for reading the amount of injectable, the rear seal 210 to contain the injectable in the barrel 216, a plunger 220 connected to the rear seal 210, an impact bridge 222 which is dislocated during injection, a plunger ring 224 to assist in user filling, a screw threaded connector to the injector 226, a notch ring 228 for attaching a key code, and a key code 230 connected to the notch ring 228. The seal and plunger ampoule 202 is sold empty so that a user can fill it with injectable medication, using the printed scale 218 for reading the amount of injectable medication. Once the user injects the medication, the impact bridge 222 is dislocated by the impact force of the injection, thereby rendering the seal and plunger ampoule 202 incapable of a second use. In this manner, the seal and plunger ampoule 202 is a single use device to prevent cross-contamination from multiple uses.

Figure 2B:
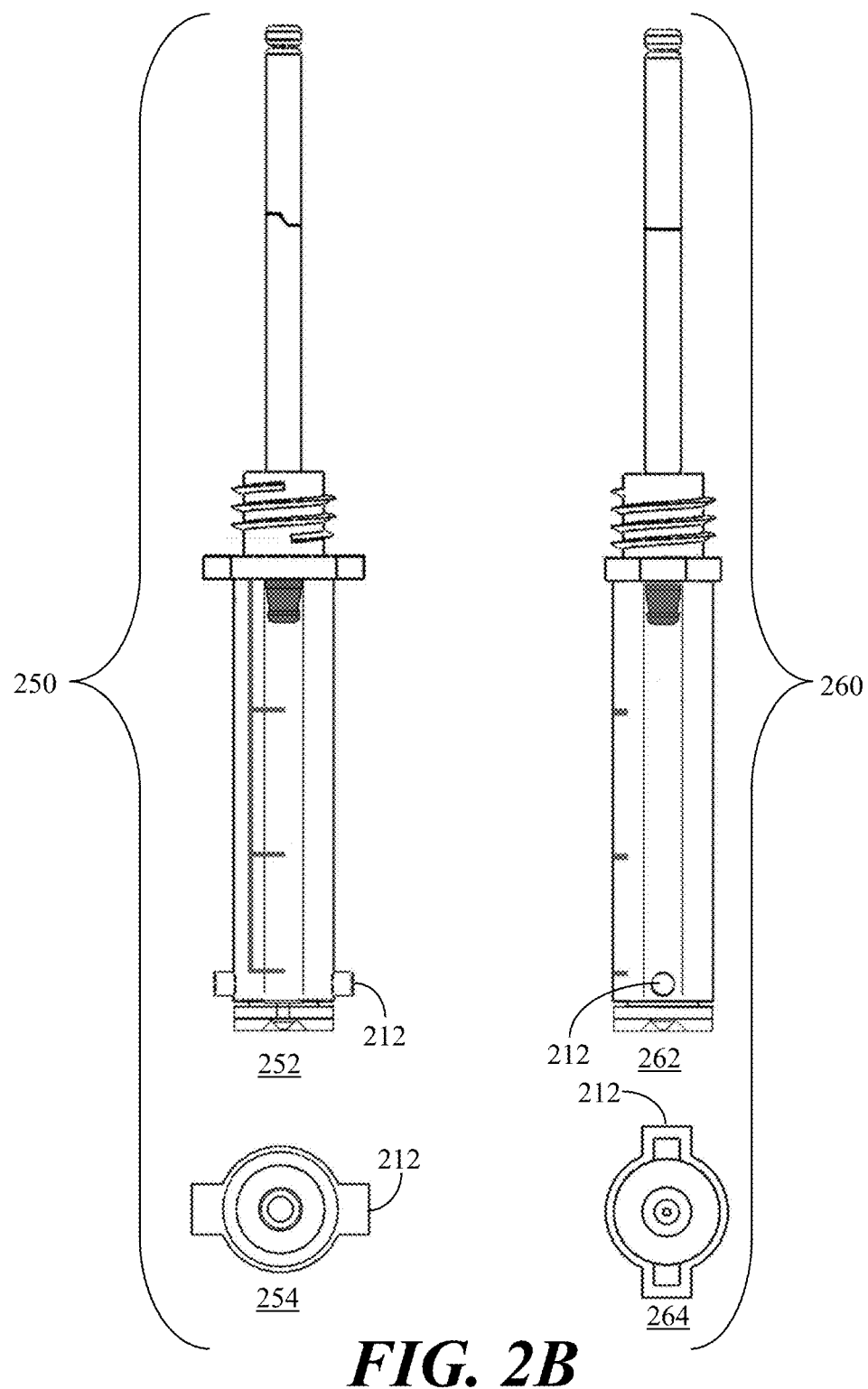

Referring to FIG. 2B, a first view 250 includes a side planar view 252 and a top planar view 254 of a seal and plunger ampoule with side safety sprockets 212. A second view 260 includes a side planar view 262 and a top planar view 264 of an ampoule module containing a seal and plunger ampoule with safety sprockets 212.

Figure 3A:
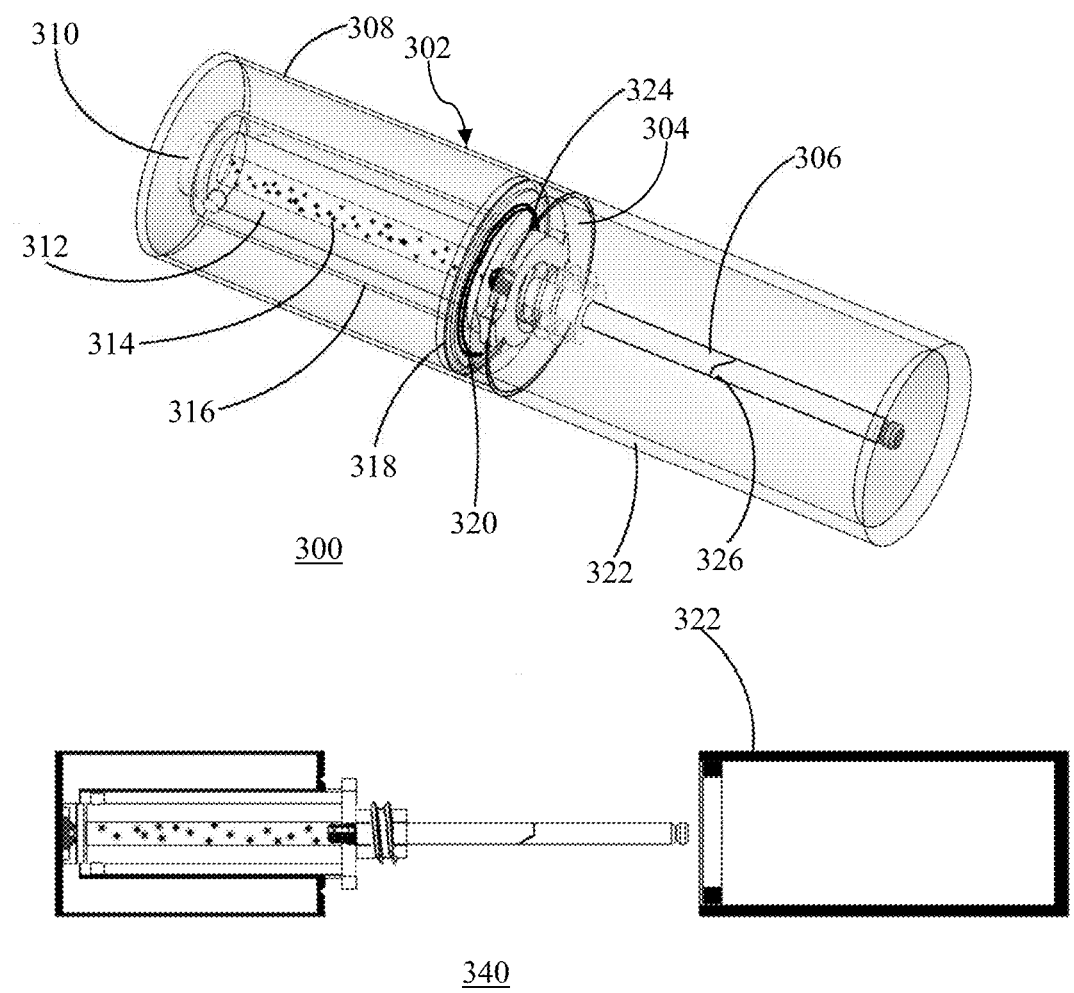
FIG. 3A illustrates a perspective view and a side planar view of an ampoule module having a seal and plunger ampoule configuration and FIG. 3B illustrates a perspective view and a side planar view of an ampoule module having a seal only ampoule configuration.

FIG. 3A depicts a perspective view 300 and a side planar view 340 of an ampoule module 302 with a rear seal 304 connected to a plunger 306. The ampoule module 302 includes a front cover 308, an orifice plug 310, a standard ampoule 312 as described hereinabove, prefilled injectable 314, a safety wall 316, a base plate 318, a quick snap ring 320, a rear cover 322 and an ampoule module key code 324 integrated with the ampoule key code 230 (FIG. 2). The module key code 324 can be different from the ampoule key code 230 as it is a superset of the ampoule key code. The module key code 324 contains information of both the ampoule and the pre-filled injectable in the ampoule module.

The rear cover 322 is removed (as shown in the view 340) for the ampoule module to be inserted into an injector. The front cover 308 is removed prior to an injection by using a quick snap motion made possible by the quick snap ring 320. The orifice plug 310 on the front cover plugs the factory filled injectable 314 in the ampoule 312 for storage and transportation. The safety wall 316 provides safety protection in the case of over-pressurization accidents. An impact bridge 326 also provides protection from cross-contamination by ensuring a single use for the ampoule module 302.

Figure 3B:
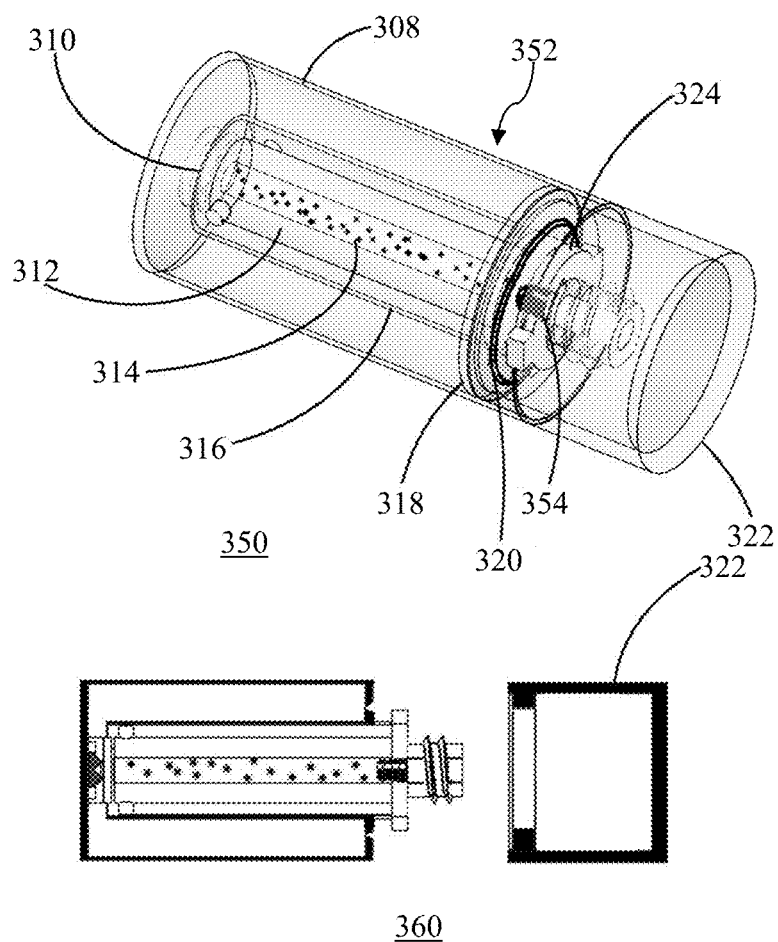

FIG. 3B depicts a perspective view 350 and a side planar view 360 of a rear seal only ampoule module 352 with just a rear seal 354. Besides the difference in the rear seal, both ampoules are the same.

The features on the standard ampoule 202 such as a) the front seal 204, b) the front seal coating 206, c) usage of the sprockets 212, d) the impact bridge 22, and e) the key code 230 are unique to the present embodiment and f) the front cover 308, g) the overpressure safety ring 214 and the safety wall 316 together, and h) the key code 324 differentiate the ampoule modules 302, 352 from conventional ampoule modules.

Front Seal

Typically, the front seal 204 is of pliable material and used to provide a cushioning effect to stretch and hold the skin taut and to provide an adhesive or cohesive effect to prevent lateral movement and/or slippage and/or abrasion during injection. The front seal 204 also provides an airtight and watertight seal when the ampoule is placed on the skin under pressure. Likewise, the front seal 204 provides an airtight and watertight seal when the ampoule is connected to another device. In addition, the front seal 204 provides a base for surface coatings and communicates with the surface upon contact. For instance, the front seal 204 provides a pressure cue to inform the patient that the injection is in process. Another form of communication by the front seal is to initiate safety handshaking with an external device, such as an airlock adaptor as discussed hereinbelow.

Figure 4A:
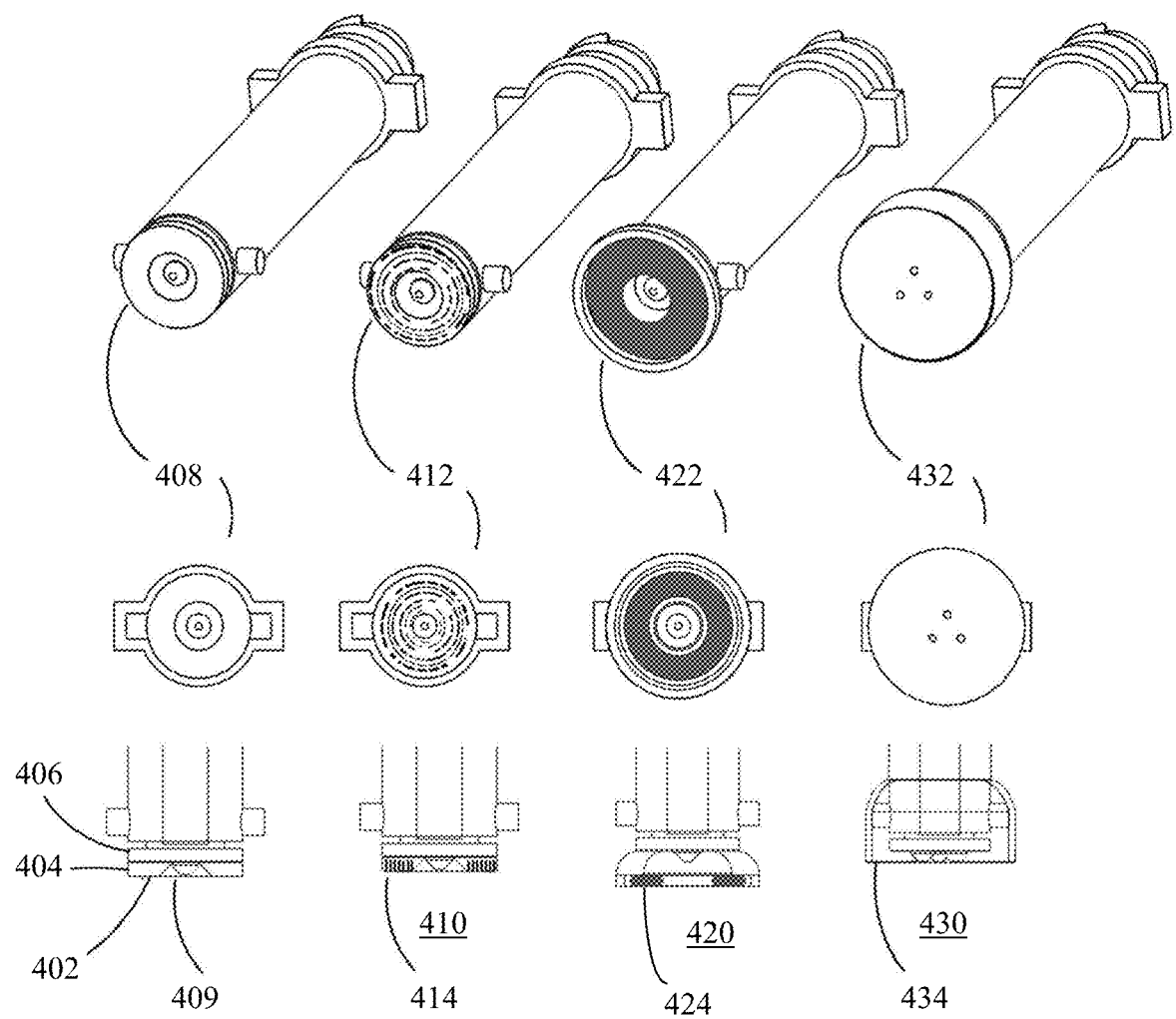

FIG. 4A shows combination perspective, top planar and side planar views 400, 410, 420, 430 of different embodiments of the front seal 204. The front seal 204 in accordance with the present embodiment has three shape surfaces: an internal surface 402, an external surface 404 and a support shape 406 to provide back support. In accordance with one aspect of the present embodiment, the front seal 408 has a flat countersunk inverted V chamfered hole 409 for the inner surface 402, a cylindrical outer shape 404, with a flat shaped support 406. Micro-texturing shapes can also be used, for instance micro grooves to mimic a lizard's padded feet 412, 414 as shown in the views 410. In accordance with another aspect of the present embodiment, an overextended shaped gel 422, 424 can be used for the front seal 204. In accordance with a further aspect of the present embodiment, an inverted bowl outer shape with no inner surface 432, 434 can be used for a multiple orifice ampoule. While not shown, another aspect of the present embodiment could use cylindrical cubic splines for all the surface shapes 402, 404, 406.

Although the front seal 204 is pliable, it can still affect the orifice to skin pressure if it extends beyond the orifice tip and produces a counter pressure before the tip touches the skin. In accordance with the present embodiment, the orifice 208 is calibrated to the skin pressure at the desired point of triggering with the shaped seal 204 by using Hooke's Law for stored force in a compressed spring of the needle-free injector and, for minor adjustments, using pressure adjusting shims as discussed hereinbelow with regards to FIG. 7. This calibration allows the predetermined injection pressure to remain primarily unchanged. However, if the orifice to surface pressure below the automatic triggering point 172 (FIG. 1B) is unimportant, the shape of the front seal can be extended above and beyond the edge of the orifice 208.

Figure 4B:
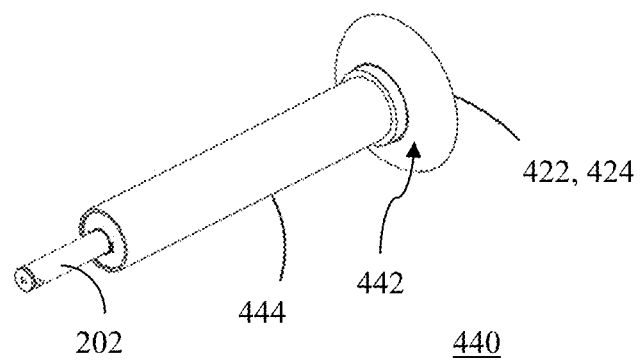

FIG. 4B depicts a perspective view 440 of an alternative use of the front seal 422, 424. The front seal 422, 424 can also be used at the rear 442 of the injector housing 444 extending above and beyond the rear edge of the housing 444.

While solitary front seals 408, 412, 422, 432 have been shown in FIGS. 4A and 4B, multiple orifices may each have their own seals and/or an orifice can have a combination of seals or types of seals in accordance with aspects of the present embodiment.

Different coating agents can be used singly or in combination where appropriate to coat the front seal 408, 412, 422, 432 at any surface or at the seal's entire multi-faceted surface. For example, adhesives, lubricating agents, antiseptic or other lyophilized pre-treatment medication may be used on surfaces of the front seal 408, 412, 422, 432. In the absence of a physical seal, these agents can be coated directly onto the ampoule surface. By using a semi-porous seal or a pre-filled bag in conjunction with the seal, liquid, solid or gel pre-treatment agents can also be pressure-dispensed prior to the injection triggering cycle.

In accordance with the present embodiment, the front seal 408, 412, 422, 432 uses shaped medical grade silicone. This provides an air and water tight seal with high kinetic friction between the orifice 208, the ampoule 202 and the skin 154 when used in conjunction with a continuous pressure on the skin 154. When the air and water tight seal is maintained for the entire duration of the injection cycle, leakage is effectively contained. Providing an air and water tight seal also means that the injectable has nowhere else to go but through the surface of the skin 154.

When an appropriate pressure is exerted orthogonal to the skin 154, the epidermal layer is locked in identical lateral movement with the seal 204. Using the natural flexibility of skin in a relaxed state and depending on the area, a ±15 mm to ±30 mm lateral movement can be achieved before a good seal is broken. With a properly shaped seal and pressure, orthogonal placement can be relaxed, typically up to twenty-five degrees off axis. The novel use of the front seal 204 alone or with the variable stroke length feature provides a solution to effectively deal with relative motion in all directions.

Detachable Seals

Numerous conventional needle-free injectors have shown that there are certain advantages in using an offset distance relative to the skin surface to allow, for instance, the injectable to gain kinetic energy prior to surface penetration.

Figure 4C:
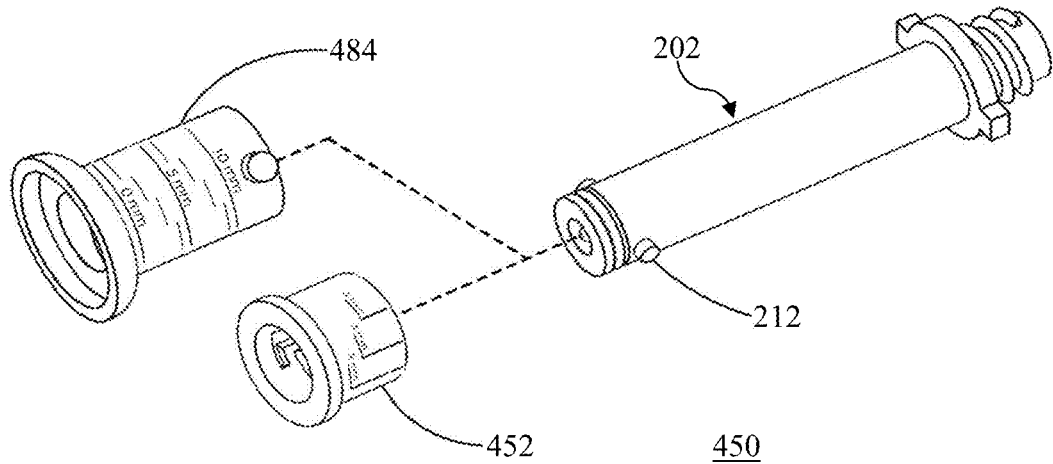

Referring to FIG. 4C, a perspective view 450 depicts an ampoule 202 with a first detachable front seal 452 and a second detachable front seal 454. The ampoule also contains sprockets 212.

Figure 4D:
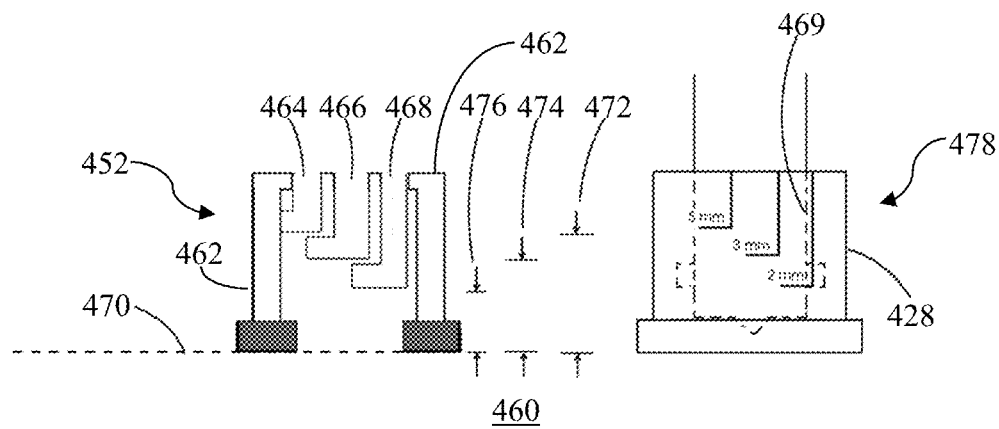

Referring to FIG. 4D, side planar views 460 depict the detachable front seal 452 of a front seal having one or more grooves which includes a hollow and transparent cylindrical hard support shape 462 containing one or more L-shaped grooves 464, 466, 468. The hollow cylinder is sized so as to allow the two front sprockets 212 of the ampoule 202 to slide into any one of the L-shaped grooves 464, 466, 468 as illustrated by the dotted outline 469 of the ampoule 202. The sprockets 212 lock themselves at different offset distances relative to the sealing surface 470 (e.g., the skin 154). For instance, the groove 464 provides an orifice-to-surface offset distance of five millimeters (distance 472), the groove 466 provides an orifice-to-surface offset distance of three millimeters (distance 474), and the groove 468 provides an orifice-to-surface offset distance of two millimeters (distance 476). The sealing surface can be fitted with different types of sealing and front coating as discussed hereinabove. An outer surface 478 of the multi-groove removable front seal 452 includes marks denoting the orifice-to-surface offset distances of 2 mm, 3 mm and 5 mm, corresponding to each of the L-shaped grooves 468, 466, 464, respectively. Any offset distance can be provided by alternative embodiments by modifying the groove pattern to different distances.

Figure 4E:
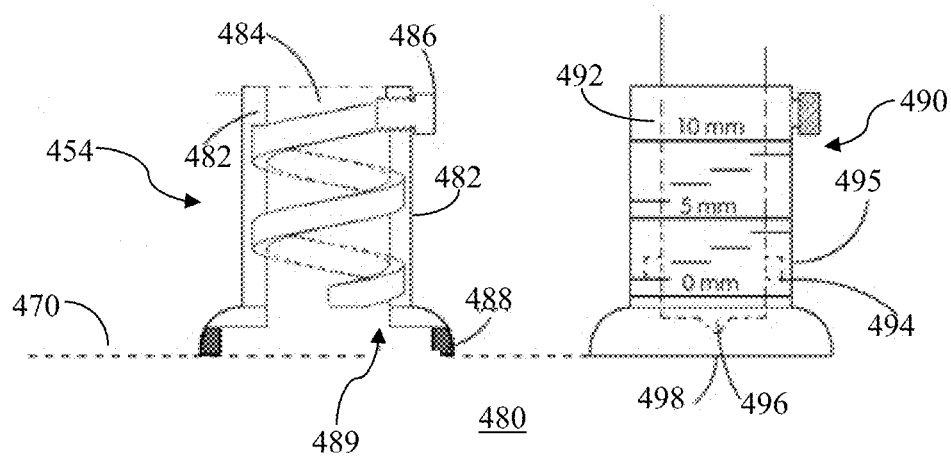

Referring to FIG. 4E, side planar views 480 depict the detachable front seal 454. The detachable front seal 454 is a screw-threaded front seal using a properly sized hollow and transparent cylindrical hard support shape 482. The two front sprockets 212 slide into a groove 484 and continue down the screw thread. A single helix is shown for simple illustrative purposes although a double helix is used in accordance with the present embodiment. When the ampoule 202 has moved into the seal 454, a knurled knob locking screw 486 can be tightened to lock the movement of the ampoule 202. Whereas the detachable front seal 452 only allows a selection of fixed distances, the detachable front seal 454 allows adjustment of distance in a continuous manner. A mixed stiff support and pliable ring seal 488 can be used for contact with the skin surface 470 to provide a shaped hollow inner surface 489. The seal 488 can be pre-coated, micro-textured or outfitted with gel as alternative embodiments as discussed in FIG. 4A.

An outer transparent surface 490 of the seal shows ampoule 202 (shown in dotted outline 492) sliding into a calibration scale position 494 of one millimeter. This scale denotes the sprocket positions 495 to inform the user of the orifice 496 to surface 498 offset distance of one millimeter. Rotating the ampoule 202 relative to the seal 454 will move the sprockets 212 up and down to give a continuous adjustment to the offset distance. This offset distance can be any distance and is not limited to ten millimeters.

The detachable front seals 452, 454 when used in combination with the programmable injector according to aspects of the present embodiment provide a wide permutation of injection effects and uses. This ability to mechanically adjust in the manner described is novel and differentiates the ampoules of the present embodiment from conventional ampoules. These two detachable front seals 452, 454 are also novel and can be used with other jet injector's sprocketed ampoules to provide adjustable orifice-to-surface offset distances or any other mechanical means to provide such attachment and adjustment.

The use of the front seal 204 is not limited to the front of the ampoule alone and can be any material, form or device that makes contact between the ampoule and another surface, or within close proximity to another surface.

Ampoule Safety Features

The front cover 308 (FIG. 3A) is constructed similar to those used for conventional needle syringes and for a pressure activated needle-free injector in accordance with the present embodiment, the front cover 308 is a safety cover and is the primary safety interlock for the needle-free injector system. With the cover 308 on, the injector is unable to operate. The cover 308 in accordance with the present embodiment has an outer diameter bigger than the inner diameter of the injector housing and encompasses the whole ampoule. The ampoule cannot be depressed into the injector with the cover on thus effectively disabling the injector from firing and making the use of the front cover 308 a safety interlock.

Conventional devices provide over pressure safety by intentionally weakening the barrel of the ampoule. If an excessively powered injector is accidentally used with the ampoule or if one or more multi-orifice holes are blocked by the medication, the excess pressure will cause the wall to distort from over pressurization and leak the injectable or cause dangerous fragmentation. In accordance with the present embodiment, the safety ring 214 (FIG. 2A) together with the safety wall 316 (FIGS. 3A and 3B) in concentric formation around the ampoule barrel 312 forms a safety feature to contain any leaking high pressure jet stream and to contain any fragmentation in the event of a barrel distortion.

Red Herring Plunger

Figure 5:
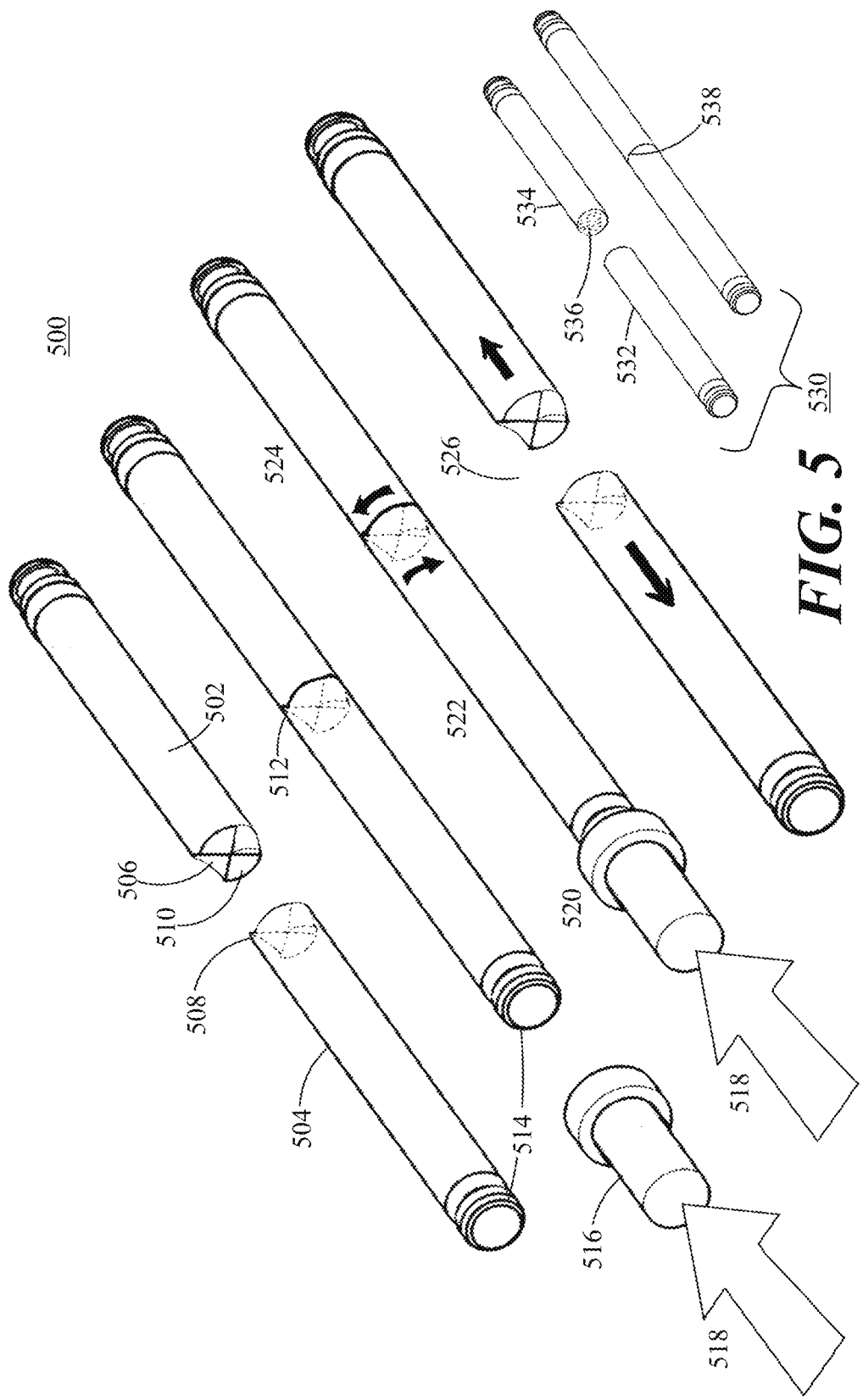
FIG. 5 depicts perspective views of fabrication and use of a plunger with an impact bridge for dislocation in accordance with the present embodiment.

This present embodiment also uses an impact bridge 222, 326 to dislocate the plunger 220, 306 during the impact cycle of the injection as a reminder not to reuse the ampoule for safety hygiene reasons. The present embodiment includes a head-to-head one-way clutch screw-head impact bridge 222, 326. Referring to FIG. 5, perspective views 500 depict fabrication of the plunger. First, the plunger is split into two interconnecting halves 502, 504, each half having a one-way clutch screw-head profile molded onto their connecting surfaces 506, 508. The two surfaces are then joined together with a small amount of adhesive 510. Putting the two halves head-on-head against each other allows a perfect fit 512 of the two surfaces 506, 508, the flat against the flat and the slant against the slant. The plunger will not dislocate with normal usage of the plunger with the ampoule. However, when the plunger end 514 suffers the impact from the pad 516 powered by force 518 from the highly compressed propulsion spring, the impact 520 will cause the slanted surfaces of both halves to produce a small amount of opposing torque or twisting action 522 and 524. This small torque is sufficient to break the thin adhesive bonding of the two halves, effectively dislocating the plunger 526. Both parts of the plunger continue their travel without interference, acting as if it is still a single plunger. In accordance with the present embodiment, there advantageously is no change to the plunger length throughout the injection cycle or the need to interlock to another part or the use of a frangible feature such as that proposed by prior art U.S. Pat. No. 8,617,099 to Williamson. There is also insignificant change to the injection pressure profile; in particular, there is no "double knocking" syndrome or jerky "step change" in the injection pressure profile experienced by conventional disablement methods.

The ease of manufacturing whereby the only change is to mold two halves instead of one single plunger and the simple application of adhesive makes this method highly scalable and suitable for automated manufacture and assembly. There is no need for plunger over-molding or to create a frangible region or a breech catchment feature, all of which adds to the cost of producing the ampoule. Another embodiment 530 of the plunger in accordance with the present embodiment uses two flat surfaces for the two parts 532, 534 of the plunger and securing them at the impact bridge 538 using a brittle adhesive 536. Even without torque, these plungers will dislocate.

Given that common sense can be applied by anyone to re-glue the two plunger halves together to bypass this safety feature, the more important reason for this feature is to provide a forensic audit trail when the plunger is reused with an adhesive different from the factory adhesive. A custom made adhesive is used in accordance with the present embodiment to leave a distinguishable audit trail. This audit trail is intended as an auditable reminder for professionals who should know better than to reuse needle-free ampoules. This forensic audit trail can also be used to provide physical evidence in procedural litigation. By adding selectable unique additives to intermix with the adhesive, the factory adhesive can be coded to differentiate plungers by manufacturing lots. These additives can range from a specific Pantone-colored or CMYK-coded dye for simple forensic differentiation to special forensic markers for more elaborate needs. This "red herring" forensic disablement feature for needle free hypodermic injection further distinguishes the present embodiment from conventional needle-free injectors.

Any action or motion exerting force above the adhesive bonding strength of the two halves of the plunger will dislocate the two halves. Tuning the adhesive strength to differentiate relative motion or relative forces on the two surfaces to separate between normal and excessive motion allows application of this "red herring" forensic disablement technique. For instance, this technique could be used for both needle and needle-free injection systems or for any needle or needle-free connector to transfer injectables from one container to another.

Another safety feature of the present embodiment is the use of a key code to prevent interconnection of inappropriate devices. A textured pattern can be placed on one or more surfaces of the ampoule so as to provide corresponding interaction with connected external devices. For illustration, these textured patterns can be mentally visualized as a cog key with teeth to fit into a corresponding keyhole: if the key does not fit into the keyhole, a connection cannot be made.

Figure 6A:
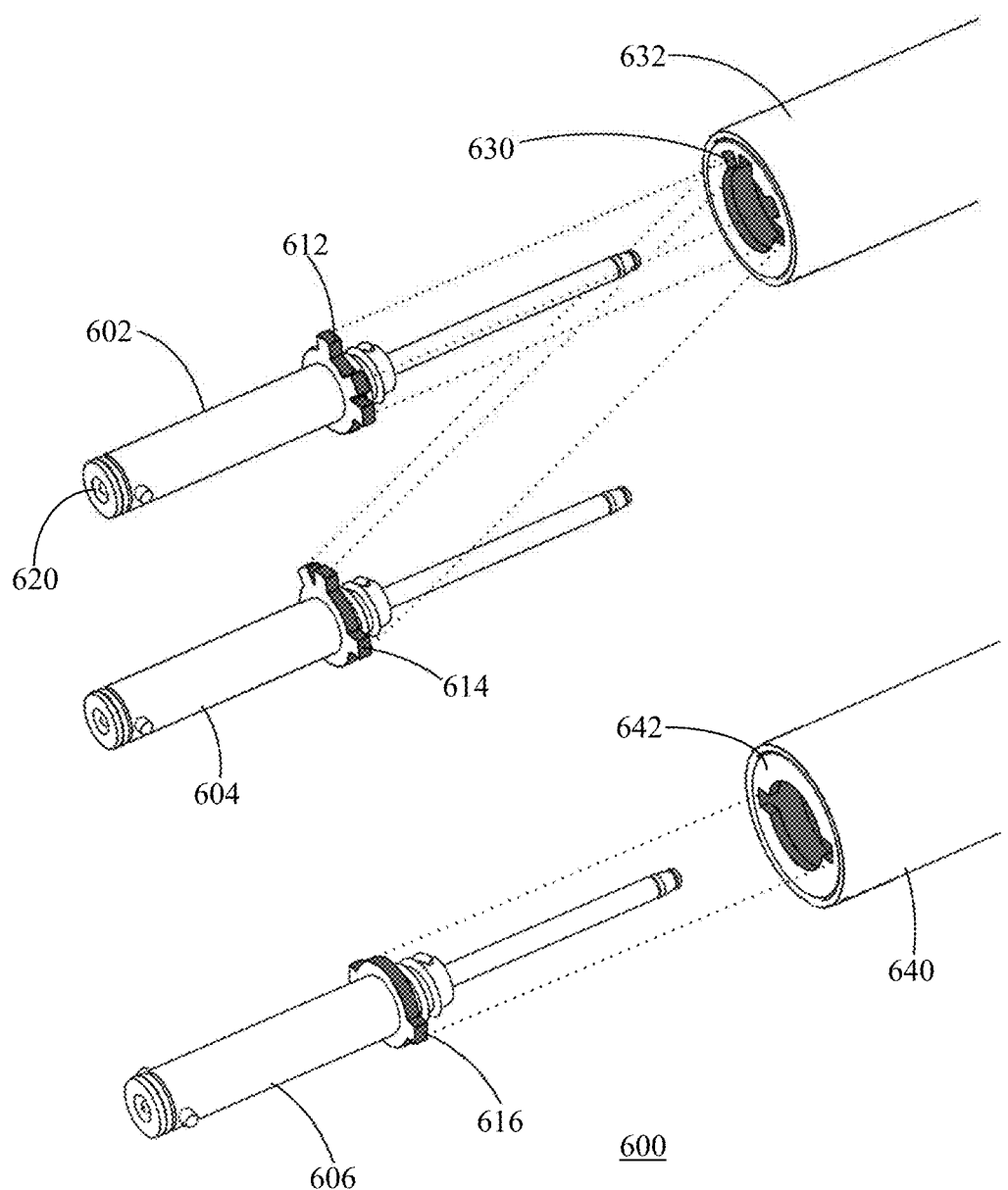

Referring to FIG. 6A, perspective views 600 depict ampoule 602, 604, 606 in accordance with the present embodiment which include rear base plates 612, 614, 616 at an end of the ampoule opposite an orifice 620, the rear base plates 612, 614, 616 including one or more sprockets. The sprockets can be slightly different in size, length, position, shape, indentations and so on to provide a large permutation of key codes. There is substantial conventional teaching on how to make a lock and a key, however there is no such physical coding usable for needle-free hypodermic injection applications which can be used without electricity. A bar code reader used to read a bar coded medication, ampoule or injector, for example, requires electricity to operate and does not inhibit interconnection, whereas electricity is not required to operate the key code and/or the reader and no electricity is required for the ampoule or the injector to physically inhibit an interconnection.

This key code can be used to match the medication to the ampoule and the injector. If the key code does not match, the ampoule is physically hindered from being inserted into the injector. Conventional identification systems may provide an alarm but they do not physically hinder the interconnection if the user chooses to ignore the alarm. Referring to FIG. 6A, the ampoule 602 includes a first medication and the ampoule 604 includes a second medication. The ampoule 602 and the ampoule 604 have the key codes formed with sprockets on their coded rear base plates 612, 614. A master key code 630 on a high powered injector 632 allows ampoule insertion therein and the high powered injector 632 is capable of accepting both types of medication (i.e., the master key code 630 is capable of accepting both key coded rear base plates 612, 614). The ampoule 606, however, has a key code 616 that inhibits insertion into the high powered injector 632 but is acceptable to be inserted into a lower powered injector 640 with a different master key code 642. The lower powered injector 640 is, therefore, key coded so as not to accept the ampoules 602, 604. This key code method also ensures that users do not confuse the different types of ampoules with the injector used and is suitable to prevent confusion during low visibility use and for the visually impaired. The present embodiment also makes a distinction between key codes on the standalone ampoule 230 (FIG. 2A) and the key code on the ampoule module 324 (FIGS. 3A and 3B). The ampoule module key code 324 is a superset of the ampoule key code 230; where additional information about the pre-filled medication is coded amongst other pieces of information if needed.

Figure 6B:
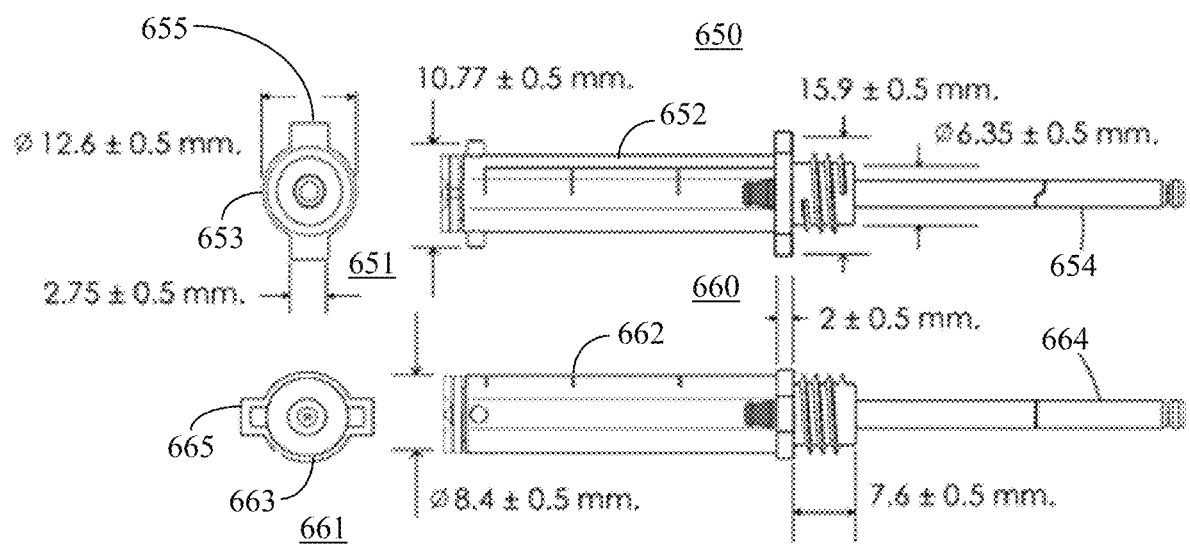
Figure 6B:
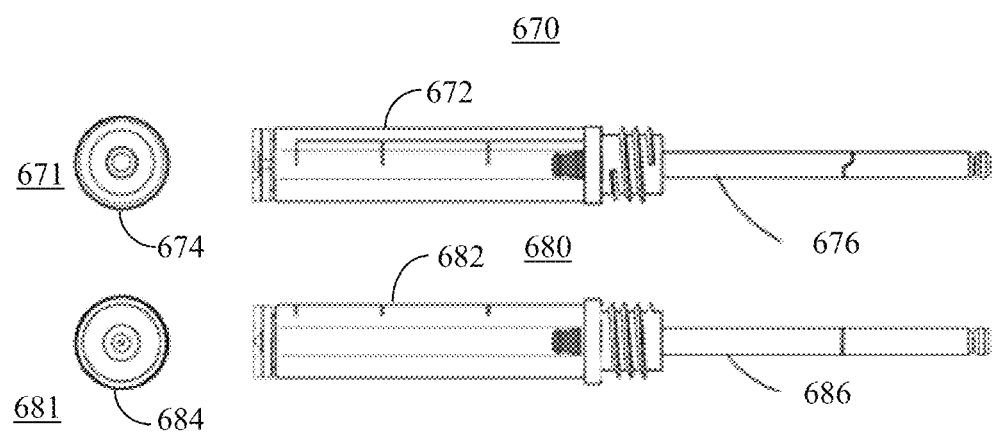

FIG. 6B depicts one embodiment of the side 650 and bottom 651 planar views of an ampoule 652 with seal and plunger 654 and with a notch ring 653 and key coded safety sprockets 655 with the dimensions shown. Another side 660 and top 661 planar views of the same ampoule 662 with seal and plunger 664 with the same notch ring 663 and safety sprockets 665 is shown from with additional dimensions. Another embodiment is an ampoule with seal and plunger without safety sprockets or a "null key code" safety sprocket. The side 670 and bottom 671 planar views of the ampoule 672 with seal and plunger 676 and with a notch ring 674 without safety sprockets is shown. The corresponding side 680 and top 681 planar view of the ampoule 682 with seal and plunger 686 is similarly shown with the notch ring 684 without sprockets. The ampoules with seal only equivalent have the same corresponding dimensions but without the plunger. These dimensions are but one set of dimensions and different ampoule products will have different sets of dimensions.

In accordance with the present embodiment, special key code patterns are used for master keys. Such special key code patterns have special significance to the present embodiment and include a) a null key code and b) a 3 and 9 key code. The null key code is a key code without any sprockets and therefore can be freely inserted into any key coded device associated with the present embodiment. The null key code is only used in special circumstances. The 3 and 9 key code includes sprockets at zero degree and one hundred and eighty degree positions (corresponding to an hour hand at the 3 o'clock and the 9 o'clock positions). These positions are the default position of the ampoules. The shape of the 3 and 9 key code sprockets 616 relative to the master key code 642 is depicted in the view 600 (FIG. 6A). The shape and size dimensions of the 3 and 9 key code sprockets 665, 675 is also depicted in FIG. 6B. The null key code ampoule 682, 692 is of the same dimensions as the 3 and 9 key code ampoules 662, 672 but without any sprockets, or with null sprockets.

The Injector

Figure 7:
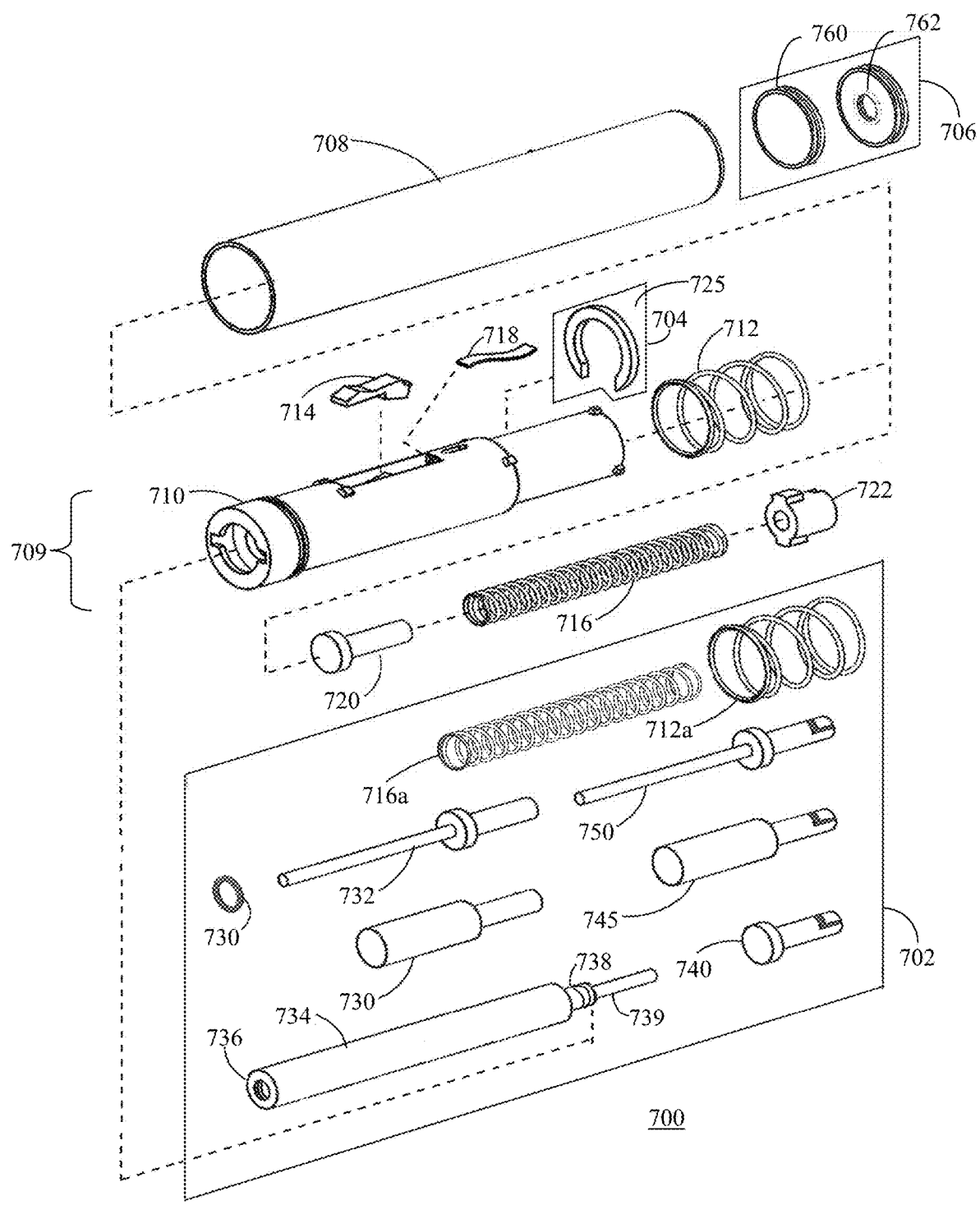
FIG. 7 depicts an exploded perspective view of the needle-free injector in accordance with the present embodiment.

Referring to FIG. 7, an exploded perspective view 700 depicts parts that make up the injector. Optional parts are shown in bounded boxes 702, 704, 706. At the open end of a hollow housing 708, a slightly smaller diameter cylindrical insert 709 is placed inside the housing 708, thus allowing the insert 709 to slide in and out coaxially within the inner tube of the housing 708. This inner insert is the bolt carrier 710.

The Bolt Carrier

The bolt carrier 710 includes three external parts, namely a pressure sensitive spring 712, a latch 714 to latch a propulsion spring 716 (discussed hereinbelow) after compression, and a leaf spring 718 used to return and hold the latch 714 in its proper place. The pressure sensitive spring 712 is used to detect the orifice on skin pressure or pressure from any contact surface. Three internal parts of the bolt carrier 710 include a pad 720 for impacting the rear seal on the ampoule (through the plunger if necessary), the propulsion spring 716 to provide propulsion energy for the injection by moving the pad 720, and a hollow end lug 722 to keep the internal components inside the bolt carrier 710. Optionally one or more pressure adjustment shims 725 can be used for pressure adjustments or to calibrate the pressure sensitive spring 712. An 'O' ring 730 is an optional part and need not be used if the injector is configured for use with low powered propulsion springs.

The Propulsion Spring

A general purpose propulsion spring 716 is included with the injector. It is possible to change and interchange all springs (the propulsion spring 716, 716a, the surface pressure spring 712, 712a and/or the leaf spring 718) in accordance with the present embodiment to achieve different effects. With access to the assembly and disassembly password or password key, the injector can be disassembled in the field and the propulsion spring 716 can be changed for a different propulsion pressure effect.

The exploded perspective view 700 also shows variations for the pad 720 such as an extended pad 730 or a plunger pad 732. The choice of pad to be used depends on the seal inside the ampoule. A standard pad 720 is used when the ampoule has a seal with a plunger as seen in the perspective view 200 (FIG. 2A) or an ampoule module seal with a plunger as seen in the perspective view 300 (FIG. 3A). A plunger pad 732 is used with the seal only ampoule module as seen in the perspective view 350 (FIG. 3B) and an extended pad 730 is used for customized applications.

Yet another variation of the pad is an extension tube 734. The extension tube 734 extends an interconnected distance between the ampoule and the injector without changing any functionality of the ampoule or injector. Both ends of the extension tube 734 mimics the corresponding ends at the injector and the ampoule. As a rigid body, any pressure felt by the ampoule is transferred to the bolt carrier and vice versa. The ampoule end 736 of the extension tube 734 includes the bolt carrier key code and the other extension tube end 738 mimics the ampoule key code to allow the extension tube 734 to be connected to the injector. A low kinetic friction cylindrical metal plunger 739 equal to the length of the extension tube 734 slides along the inside of the extension tube 734. When the ampoule, extension tube and injector are connected together, the only change is that the reach of the injector is increased.

Other variations of the pad 740, 745, 750 allow a rear reloading mechanism to be connected to the pad. The optional rear screw 760 and optional hollow rear screw 762 are only used in injector versions configured for rear through-hole reloading, discussed hereinbelow. Front loading injectors do not need these screws.

Figure 8:
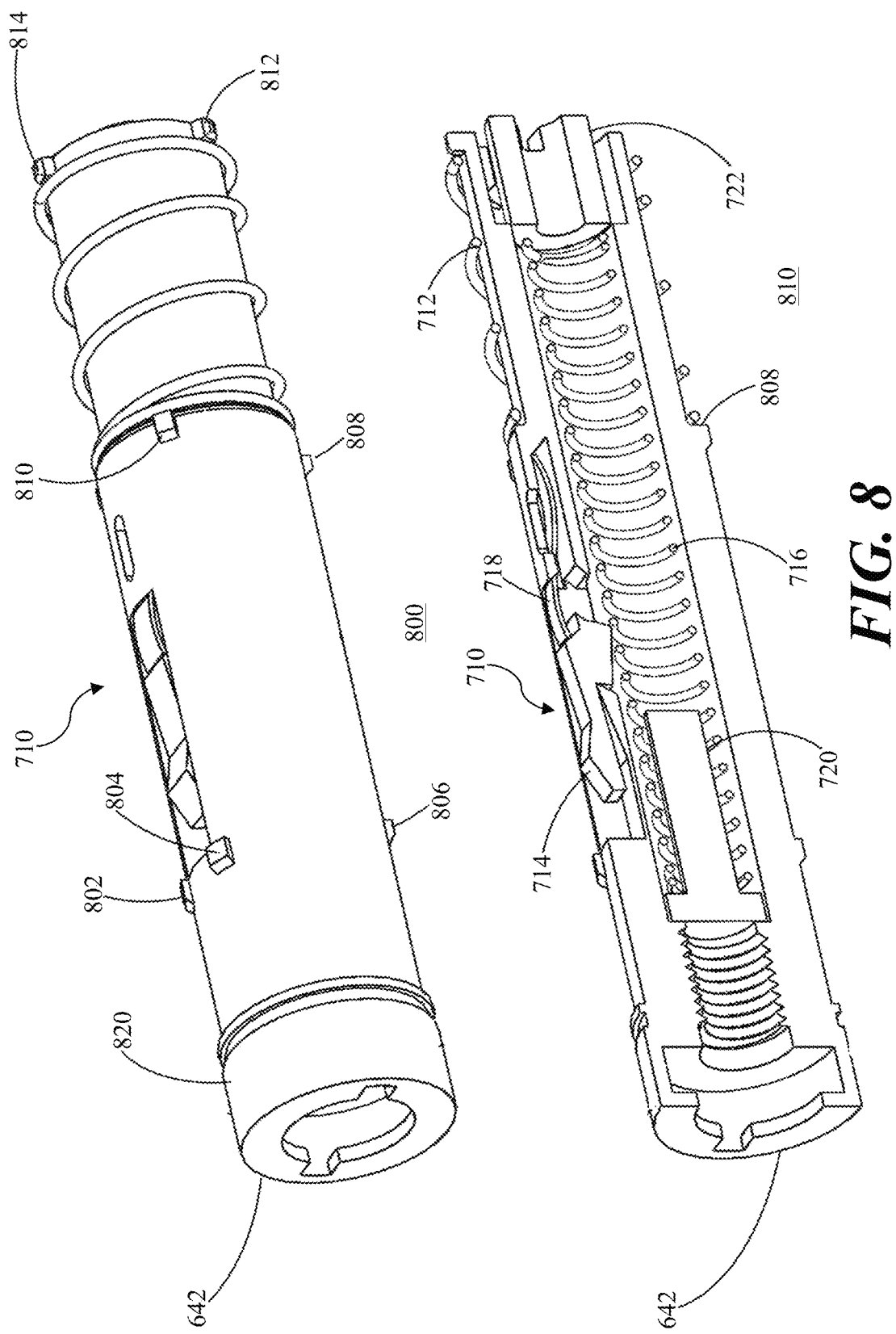
FIG. 8 depicts a perspective view and a cross-sectional perspective view of the assembled bolt carrier including sprockets and rings in accordance with the present embodiment.

The bolt carrier 710 is designed and shaped to hold all the parts in one rigid body; the other rigid body is the housing 708. To reduce kinetic friction when sliding in and out of the housing, the bolt carrier 710 has a smaller diameter than the housing 708 for a loose fit. FIG. 8 depicts a perspective view 800 and a cross-sectional perspective view 810 of the assembled bolt carrier 710. Various sprockets, including sprockets 802, 804, 806, 808, 810, 812, 814, are carefully placed along an outside surface of the bolt carrier 710 to minimize kinetic friction. These sprockets 802, 804, 806, 808, 810, 812, 814 are also used to provide structural reinforcement and a means to navigate through a finite system machine (FSM) maze which will be discussed later. A red colored ring 820 at the forward edge provides structural support as well as providing a visual cue of the armed status of the injector when it protrudes out of the housing 708. While the red ring 820 remains non-visible inside the housing 708, the injector is safe.

Automatic Triggering Using a Closed Loop Control System

An open-loop control system is fundamentally what all manually triggered jet injectors are: the orifice is pressed against the skin and the injection mechanism is hand activated. The human body provides close loop control by sensing whether the orifice pressure on the surface is sufficient. The human body adjusts this pressure automatically and learns by trial and error how to administer a needle-free injection with no leakages. Thus, a person must be taught the minimum skin pressure to prevent leakage, which usually results in a large safety margin to prevent a leaky injection.

To automatically trigger a jet injector at an optimal and predetermined pressure requires a close-loop control system within the jet injector to replace the human sensor. This is particularly useful if the tactile sensors on a person are dulled by wearing heavy gloves or numb from cold, or when the surface pressure is difficult to feel because of an unwieldy injector design. Some conventional injector designs overcome this by incorporating a close loop mechanical sensor at a single pre-determined surface pressure setting. However, human experience is needed to regulate this pressure setting as circumstances change. Whereas a skilled person knows what to do, a different person or different human sensor has to be taught this skill to differentiate the pressure settings for a cow, a grown chicken or a young chick so as not to injure or kill the subject. Thus, soft tissue on the face or sensitive tissue on the penis or vagina or delicate tissue of internal organs would require an extensive learning process to acquire these skills. Using mechanically pre-programmed user selectable settings on the injector, the user need simply select the type of injection to be performed. Thus, other than the need to hold the injector orthogonal to the tissue surface and exert a coaxial pressure on the housing towards the tissue surface, operation of the needle-free injector in accordance with the present embodiment advantageously requires no extra skill to exert the optimal injecting pressure.

U.S. Pat. No. 8,740,838 to Hemond of MIT describes an electrical close loop servo-controlled computerized device wherein the sensors primarily relate to the propulsion of the injectable fluid at the point of injection and during the course of an injection. The language of the description and the claims of the Hemond patent teach that the injector sensors are not configured to sense skin properties at a time prior to the injection, say t−n seconds, where t is the time of injection and n is the time prior to the injection and prior to deformation of an ampoule and prior to propulsion pressure (e.g., t−1 second or t−1 ms). While the propulsion pressure profile in accordance with the Hemond patent appears to be pre-computed, Hemond neither teaches nor suggests an automatic injection when a pre-determined injector on skin pressure is reached. In order to do such, the PI Controller FPGA of Hemond must have a voice coil position feedback that is used prior to the injection being carried out. This is evident from the design of their injector with a manual activation switch (disclosed in FIG. 4 at ACTIVATION SWITCH 440) and the other figures of Hemond which only indicate a time of t=0 and t>0 at the origin. This is also evident from the fact that the Hemond two position-based control components are only active during the injection phase and not before. While Hemond teaches a sensor for sensing deformation of the ampoule, these teachings do not apply to pre-injection sensing of injector on skin pressure as the pressure involved on the skin surface is insignificant and insufficient to deform the hard materials of the Injex-Equidyne ampoule or any ampoule used for jet injection. The Injex-Equidyne ampoule used in the disclosure of Hemond is a Makrolon® polycarbonate-based plastic designed to be impact resistant so as to contain the high pressures of a jet stream. According to Hemond FIGS. 7A and 7B, the forces required for ampoule deformation go up to two hundred and fifty Newtons, whereas skin pressure is differentiated in tens of grams force.

In accordance with an alternate embodiment, the mechanical pressure spring 712 used for skin pressure sensing is replaced with an electrical equivalent. An electrical sensor such as a piezoelectric strain gauge or a voice coil with dynamic sensitivity in gram force for skin pressure discrimination can be used. Whereas the Hemond device computes and adjusts the propulsion pressure in real time, this alternate embodiment advantageously pre-computes such propulsion pressure and delivers working pressure profiles for injectables with different viscosity without the need to continuously monitor the progress of the fluid during the whole injection cycle.

In accordance with the present embodiment, the pressure profiles are mechanically pre-computed by a PING Replicator System and the injector is subsequently programmed and configured for use using a finite state machine mechanical computer (FSMMC) and PING formal language (as introduced hereinbelow). The PING Replicator System in accordance with the present embodiment uses proprietary and novel software for use with a non-electrical mechanical computer with our equivalent of PING to replace the FPGA of Hemond and to have a separate but discrete pressure solution for a wide variety of injectable viscosities. Different propulsion pressure profiles are realized by the reconfigurable spring system wherein springs 716, 716a can be interchanged. The difference between the Hemond apparatus and the present embodiment is analogous to the difference between use of a dive computer to continuously compute real-time depth profile of a diver versus the use of a look-up table with pre-computed dive table profiles, where the Hemond apparatus is analogous to the dive computer and the present embodiment is analogous to the look-up table. In addition, the present embodiment does not require electricity and is, therefore, a very different device from the Hemond device.

The present embodiment advantageously removes the need for human intuition or learning by pre-programming skin pressure and propulsion settings so that a totally unschooled person can deliver more than one type of injection correctly during first time use by manipulating the settings switch (e.g., skin pressure settings of ID, SC or IM or additional settings of SC1, SC2, SC3, Custom 1 or Custom 2). The skin pressure settings are used in conjunction with a selection of propulsion springs (e.g. propulsion spring 716 or propulsion spring 716a) by the factory or customized by the practitioner.

Figure 9:
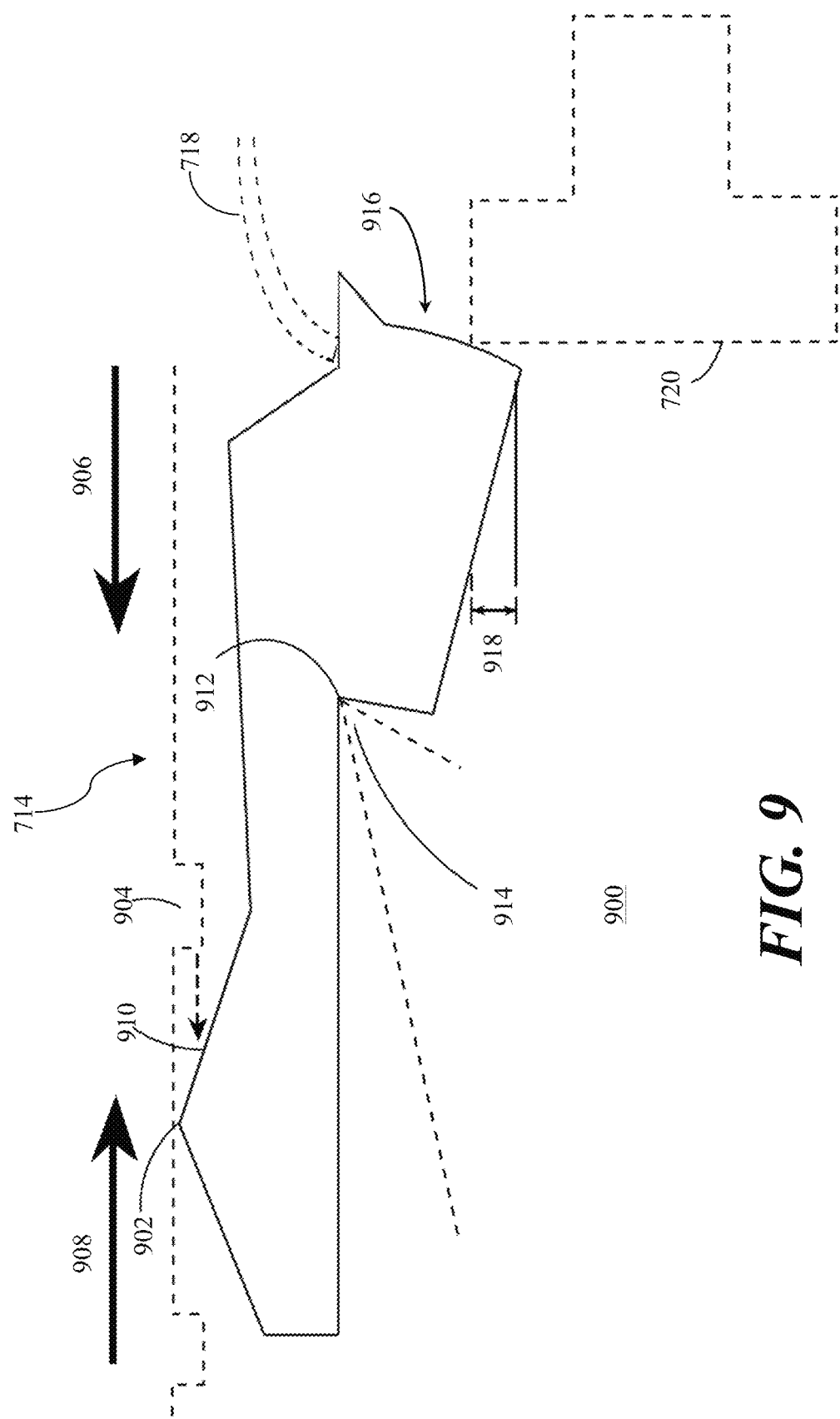
FIG. 9 depicts a side planar view of the bolt carrier latch in accordance with the preferred embodiment.

Referring to FIG. 9, a side planar view of the latch 714 in accordance with the present embodiment is depicted. A novel hump-shape 902 design allows bi-directional travel of the firing ring 904 over the latch, with a forward stroke 906 and a return stroke 908. Unlike conventional injection latches, after the latch 714 is depressed, the firing ring 904 does not stop when it strikes the latch 714 at point 910, but rides over the hump 902 in the forward stroke 906 until the stroke length is complete. While it is possible to have a short stroke to disengage the latch, the present embodiment utilizes a long stroke for motion compensation purposes and sensitive skin pressure discrimination. The latch 714 pinlessly pivots around a seesaw pivot point 912 to provide reduced friction for latch operation. Instead of a pivot pin, the pivot point 912 seesaw pivots on a knife-edge pivot 914. In this manner, the latch 714 is high in structural integrity due to no pin hole while advantageously reducing friction during pivoting to almost zero enabling the latch 714 to hold back the injection pad 720. In addition to reduced friction, a curved surface 916 exerts little to no force on the injection pad 720 during latch release. The reduced friction and the little force exerted against the injection pad provide a low latency latch with a "hair trigger" release requiring little sear distance 918 for the release of the pad 720.

Figure 10:
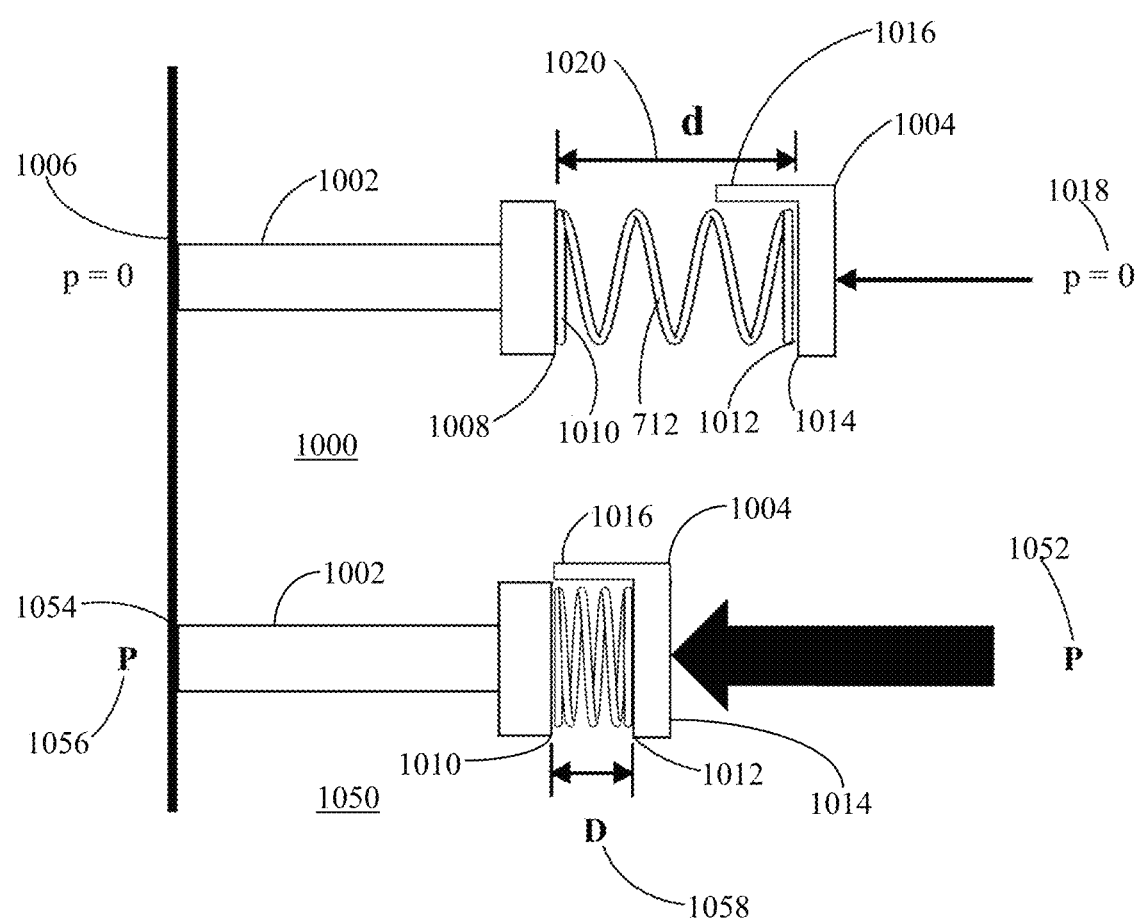
FIG. 10 illustrates side planar views of interaction of parts of the injector to perform an automatic injection in accordance with the present embodiment.

FIG. 10 uses two planar views 1000, 1050 to provide a simple illustration of the interaction of the parts in the present embodiment to perform an automatic injection. The design uses an optimal closed loop, low latency methodology. The present embodiment includes two rigid bodies, a) the ampoule and the bolt carrier 1002, and b) the housing 1004. Together they sandwich the pressure sensing spring 712.

As the ampoule and bolt carrier moves as one rigid body, the pressure on the skin 1006 is the same as the pressure on the retardation ring 1008 of the bolt carrier 709. The retardation ring 1008 is in contact with the left edge 1010 of the pressure sensing spring 712. The right edge 1012 of the spring 712 is in contact with the pressure sensing ring 1014 of the housing 1004. Thus, any pressure felt at the skin 1006 is transmitted to the pressure sensing ring 1014 from the retardation ring 1008 (which is in rigid contact with the skin 1006) via the spring 712.

The pressure sensing ring 1014 and the firing ring 1016 are conjoint on the housing 1004 which is the second rigid body. Pressing the housing 1004 against the skin 1006 moves the pressure sensing ring 1014 and the firing ring 1016 together as one. Any coaxial pressure felt at the pressure sensing ring 1014 is identical to the pressure at the firing ring 1016 and at the housing 1004. At zero pressure 1018, the spring 712 is at a relaxed position of distance d 1020.

When pressure 1052 is exerted on the housing 1004, this same pressure is also transmitted to the pressure sensing ring 1014 and the firing ring 1016. The same pressure is transmitted through the spring 712 to the bolt carrier 1002 and through the ampoule and onto the skin 1054. So the pressure 1056 on the skin 1054 in reverse is also the same pressure exerted on the housing 1004. At a pressure P 1052, 1056, the spring distance has now moved to D 1058. Careful selection of the spring 712 gives us the spring constant k. Using Hooke's Law $F=k \cdot X$, where F is the force and X is the distance travelled, the relationship between force and distance can be calculated. In accordance with the present embodiment, the term "spring" is used to describe a single spring or multiple springs used in series or in parallel or in concentricity with one another, or in any combination thereof. In the case where multiple springs are used, Hooke's Law for multiple springs k1, k2, . . . is used.

Figure 11:
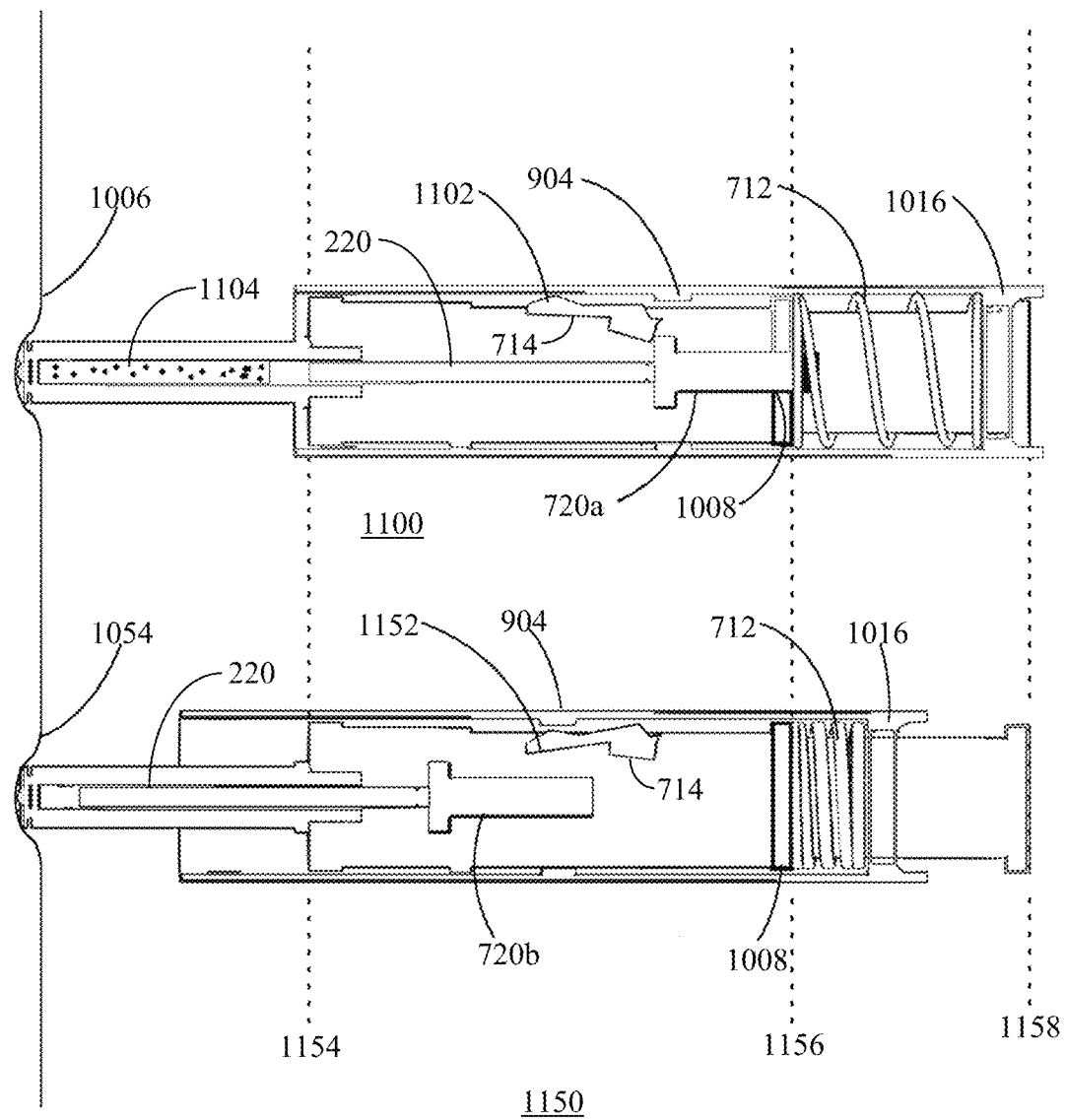
FIG. 11 illustrates side planar cutaway views of the injector to perform an automatic injection in accordance with the present embodiment.

Referring to FIG. 11, side planar cutaway views 1100, 1150 depict more accurate physical illustrations of FIG. 10 with the two rigid bodies drawn in appropriate shape for a clearer explanation of how the optimal close loop is achieved as compared to conventional injectors. The before 1006 and after 1054 pressure positions on the skin is shown respectively; the before release position 1102 and after release position 1152 of the latch 714 as the housing moves towards the skin is also shown. The movement of the firing ring 904 towards the latch 714 and the before compression and after compression of the pressure spring 712 are shown. It is important to note that the bolt carrier remains anchored in the same position 1154 but the housing moves ahead together with the pressure ring 1016. The retardation ring 1008 on the bolt carrier also remains unmoved at position 1156. The before location of the injection pad 720a and the after location of the injection pad 720b are also shown. In this illustration of an alternative embodiment of a shorter housing with an open rear end, note that the rear of the bolt carrier 709 juts out of the housing 708 at position 1158 when the ampoule is depressed against the skin.

In summary, when the ampoule 104, 113 is pressed against a surface such as skin 1006, 1054 or the surface move towards the ampoule or is pulled towards the ampoule, the firing ring 904 releases the latch 714 at a predetermined pressure and continues to travel to provide motion compensation ability. The latch 714 releases the injection pad 720a powered by the pre-compressed spring 716 before the end of an extended stroke. The injection pad 720b pushes a seal with a plunger 220 to force a volume of fluid 1104 in an ampoule barrel 216 through a tiny orifice 208 and subsequently through and under the skin. This pressure sensitive mechanism is equally effective on the skin of animals or any biological surfaces.

Advantage of a Long Stroke Length

The relationship between pressure and distance travelled by the housing before the automatic injection takes place can be predetermined by Hooke's Law. In accordance with the present embodiment, an injection stroke length of thirty millimeters and a trigger travel of fifteen millimeters are optimal in order to provide sufficient 'feel' during injection. A different stroke length or firing ring travel could be used without departing from the spirit of the present embodiment, including a firing ring travel distance of zero.

As demonstrated in FIG. 1B, a long stroke length allows the ampoule orifice 208 to maintain skin contact throughout the entire stroke cycle until the injector is removed from the skin. This is to allow sufficient time to deliver a large volume of injectable. Kinetic energy is accumulated by the pressure sensing spring 712 during the injecting motion. In the event that the skin starts to move away from the orifice 208 before the injection is complete, this kinetic energy is used to compensate for such movement. At the same time, the excess pressure stored in the spring 712 normalizes any negative pressure from skin movement to continue providing a good seal between the orifice 208 and the skin. In applications where relative motion is a concern, a more powerful pressure spring can be used with a follow through motion. A more powerful pressure spring 712 will store more kinetic energy to reduce any lateral slippage and maintain a stronger air tight and water tight seal. A longer stroke length provides a longer coaxial motion tolerance in distance and duration. Combining this with the use of the ampoule front seal 206 to tolerate lateral skin movement and a zero latency triggering mechanism, the only limiting factor is the amount of time taken to administer a volume of injectable. Reducing this time increases the tolerance to relative motion, with a full injection cycle time of fifteen milliseconds and keeping the coaxial and lateral movement tolerance to the same fifteen milliseconds means that the apparatus is tolerant to a relative motion of one meter per second in any direction.

A long stroke length also provides an ability to "look ahead" in motion compensation situations. The moment this apparatus touches skin, a "pressure memory" begins as the bolt carrier and the ampoule slide in and out of the housing, increasing and decreasing as the relative motion changes, or when the relative skin pressure changes. By relocating the position of the firing ring along the tube, we can adjust the firing by time or distance. For instance, we can program the injector to fire sooner or later in anticipation of the application. With a long stroke length having a thirty millimeter stroke and a mid-firing position of fifteen millimeters, a memory of the fifteen millimeters of travel prior to the point of firing is provided. Thus, the present embodiment provides a stroke length "look ahead" memory while conventional injectors do not have any memory before the ampoule surface touches the skin surface.

Zero Latency, Accuracy and Repeatability

Although Hooke's Law is universal to any spring, the present embodiment implementing Hooke's Law using only two rigid bodies means that the orifice-to-skin surface pressure is instantaneously conveyed to the firing ring. A low kinetic friction latch also means that the latch releases the pad quickly to impact the plunger and seal to begin delivery of the injectable through the skin using the propulsion force provided by the compression spring inside the bolt carrier. Comparing the reaction time of a high latency conventional injector, (e.g., 210 ms just for cam rotation for U.S. Pat. No. 5,480,381 to Weston), the present embodiment provides a far more efficient injector. An analogy is a group of people sitting in a ring around a camp fire to relay the same message from one person to another around the ring. It takes time for the message to circulate around the group of people and a larger group takes a longer time for the message to return to the origin—this is latency. The message may also be corrupted by the relay—this is accuracy. Providing the same message again may result in a different message returned—this is repeatability. The present embodiment advantageously provides a needle-free injector that has zero latency, is highly accurate and is highly repeatable because it comprises only two rigid bodies and a spring.

As there are only two solid bodies and a pressure spring before the latch is released, the present embodiment has an optimal close loop control system; as optimal as it can get. There is no hysteresis lag, no Analogue-to-Digital conversion, no Digital-to-Analogue conversion, no FPGA clocking, no differentiation logic gates, no quantization, and no program executing latency in operation in accordance with the present embodiment. The present embodiment uses a continuous analogue pressure sensing mechanism which is completely different than the Hemond digital injector described hereinabove.

Surface Pressure Discrimination

A long stroke length also allows a more sensitive determination of surface pressure. For instance, if the stroke length is ten millimeters and ten Newtons needs need to be differentiated, the resolution is one Newton per millimeter. If the stroke length is thirty millimeters, the resolution is 0.33 Newtons per millimeter, or three times more sensitive. In addition, using a two Newton pressure spring 712 will provide the equivalent of a sixty-six-gram force per millimeter travelled for a light touch application. Unlike digital systems, the pressure discrimination in accordance with the present embodiment is continuously analogue in nature. Such fine discrimination in pressure is possible during medical procedures because the injector weighs less than fifty grams in total and the rigid body design means any pressure variations on the surface is picked up by the injector before it is felt by the surgeon; an analogy to a car riding on a soft suspension. It is highly unlikely to have ampoule tip puncture or harm delicate tissue since the ampoule is on suspension springs, so to speak. At such sensitivities, the weight of the bolt carrier itself for an orthogonal injection accounts for almost one millimeter variation of spring movement. Using PING, minor repositioning of the firing ring can be reprogrammed at calibration as described hereinbelow.

Finer pressure discrimination is provided with the use of a restraining adaptor without a hook restraint (restraining adaptors and hook restraints are discussed hereinbelow in regards to FIGS. 20 and 21). The high maneuverability of a syringe-type handhold allows a plastic surgeon, a dental surgeon or a veterinarian to continue his practiced fine motor control skills with hand grip familiarity. For example, the success of a wrinkle removal treatment depends on injecting precisely on the wrinkle and not on an edge of the wrinkle as injecting on the edge of the wrinkle would accentuate the surface defect. As compared to conventional needle-free injectors, the present embodiment removes the need to manually trigger an injection. This capability can be better understood by using a firearm handling analogy: how to squeeze a trigger is no longer relevant because there is no trigger. Similarly, the use of a separate triggering mechanism to activate a low sear force latch 714 holding back a compression spring of one hundred Newtons is different from moving a lightweight firing pin on a firearm. Thus, as stated hereinabove, the reduced friction and small sear force provide a low latency latch with a "hair trigger" release.

A conventional needle-free injector described in US Patent Application Publication No. 2003/0163111 to Daellenbach utilizes a thin and long end effector. The high center of gravity, high mass and high angular momentum provided by the Daellenbach device provides obstacles similar to hitting a golf ball with long club shaft with a small club face versus hitting the same ball with a short handle broad face table tennis bat using a pen grip. The present embodiment, on the other hand, provides high maneuverability, has a low center of gravity, a low mass and a low angular momentum by design.

Daellenbach also made this abundantly clear when he stated: "Typically, end effector 14 is made of a material capable of being sterilized and able to withstand the pressure generated by injector 12. Moreover, in some laparoscopic and thoracoscopic surgical procedures, it may be desirable for end effector 14 to be rigid. In this case, suitable materials include stainless steel, titanium, composite structures of metal and plastic, and the like. If surgical procedures require a malleable and/or manipulatable end effector 14 to form around or within anatomical structures, such as contemplated with some laparoscopic, thoracoscopic, and arthoscopic procedures, plastic materials including polyurethane, high-density polyethylene, amorphous polyamide, poly etherimide, and polypropylene may be suitable." These materials recommended by Daellenbach are all very hard materials capable of damaging fragile tissue with a bad maneuver.

Although the means of propulsion is different, gas in Daellenbach and a compression spring 716 in the present embodiment, the need to contain the injectable during the high pressure jet streaming through the orifice or orifices remains the same. However, the present embodiment does not suffer from the same concerns for sterilization as Daellenbach. The materials used in the present embodiment are single use disposable ampoules and single use disposal end effectors utilizing sterilization by irradiation with gamma rays or any other established methods to meet all current medical standards in sterilization and biocompatibility. In addition, Daellenbach and the present embodiment utilize opposite end effector philosophies: whereas Daellenbach uses a rigid end effector capable of withstanding jet streaming, the present embodiment utilizes a soft medical grade silicone or silicone-gel front seal 204 thereby containing the high pressure jet streaming issues by the jet injecting ampoule 202 as seen in FIGS. 2A and 4A. Whereas Daellenbach adjusts the length of the end effector to accommodate reach, increasing it from four inches to six inches to ten inches, the present embodiment increases ampoule reach by using a low cost extension tube 734 (FIG. 7). And Daellenbach expresses concern over the fragility of internal organs by restricting his end effector size to between 0.1 to 0.3 inches with a preference for 0.2 inches. A prior art ampoule for use in accordance with the present embodiment is about 0.3-inch diameter. However, this 0.3-inch diameter is insufficient for pressure distribution on sensitive organs. The present embodiment provides end effectors by way of a front seal which distributes pressure over a large area of ten millimeter to twenty millimeter diameters so as not to damage sensitive organs by applying a spot pressure. Our soft seal (FIG. 4A) end effector advantageously distributes the surface pressure over a large area while providing a better seal and tactile grip on the surface of an organ. Using a shaped internal surface gel seal, the seal is able to accommodate to the curvature of small organs. When used in conjunction with a PING light touch program to administer an injection automatically at a predetermined light surface pressure, and configuring the injector for low powered propulsion using a lower powered spring 716a, the present embodiment provides a novel and advantageous needle-free injector which is less likely to damage fragile organs when performing an equivalent exercise to Daellenbach.

Furthermore, the way the Daellenbach injector and the present embodiment accommodate angular injections are different: Daellenbach angles the end effector and effects frontal surface pressure; the present embodiment uses a separate back pressure restraining device to push/pull the surface towards the orifice or orifices for a skewed or horizontal injection (see FIGS. 20 and 21 discussed hereinbelow). For these reasons and others, the apparatus of Daellenbach and apparatuses in accordance with the present embodiment are different. Furthermore, other features available in the present are neither taught nor disclosed in Daellenbach.

Figure 27:
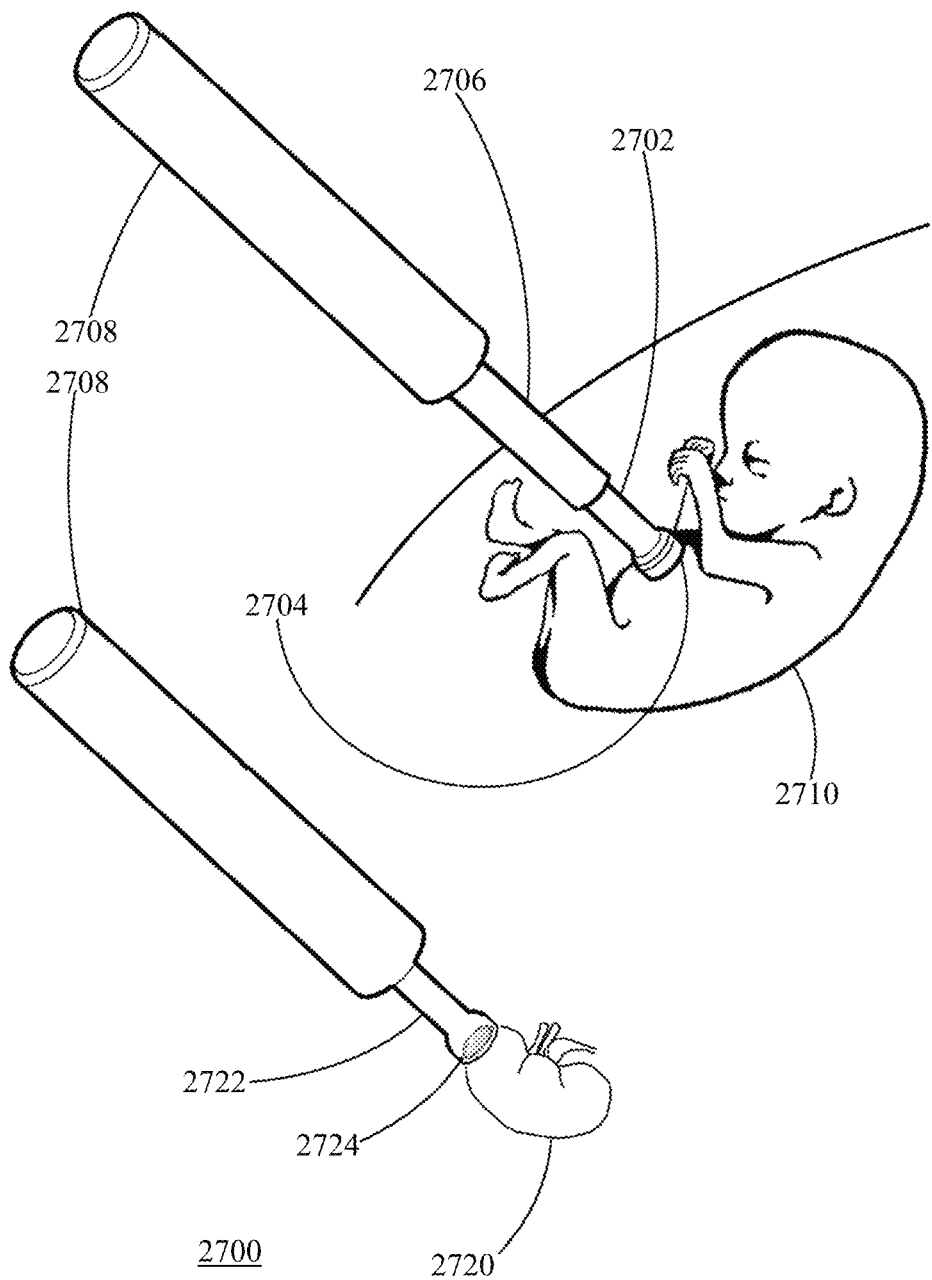
FIG. 27 depicts perspective views of internal organ injection on fetal tissue and organ tissue in accordance with the present embodiment.

Referring next to FIG. 27, perspective views 2700 depict internal organ injection on fetal tissue and organ tissue in accordance with the present embodiment. An ampoule 2702 with a wide surface area soft seal 2704 is connected to an extension tube 2706 to increase the reach of the pressure sensitive injector 2708. A surgeon maneuvers the ampoule orifice over the injection site and applies pressure on the housing. The injection is automatically administered to the fetal tissue 2710 or internal organ when the appropriate and predetermined surface pressure is reached. A light-touch surface pressure is used. The propulsion spring is configured to supply enough penetration power but not enough to damage the fragile organ 2710. The wide surface soft seal 2704 distributes the frontal pressure evenly throughout the contact surface area. For a smaller organ 2720 in a smaller body, the extension tube is not necessary. An ampoule 2722 with a more concave surface soft seal 2724 is used to fit the shape of the smaller organ and the injection is easily carried out in the same manner.

Finite State Machine (FSM)

The normal use of Finite State Machine logic is for the abstraction modal or modeling of computing systems and interfaces, with the use limited to virtual state diagrams, flow charts (FIG. 12), software proofing and so on. Conventional wisdom dictates that it is not possible to physically realize such a FSM abstraction. Computer scientists need to be gently reminded of the past where one of the earliest computing machines such as the Babbage Difference engine was a mechanical calculator designed to tabulate sophisticated polynomial functions. Another early computing machine was the Turing abstraction which eventually led to the von Neumann CPU. Numerous cam and cam followers, sprockets and grooves, as well as mechanical computers for artillery sighting have also existed for some time. However, these systems are fixed for a single use and difficult to program or reprogram. Further, they do not provide the capabilities of what is understood as Turing Complete computers today.

In accordance with the present embodiment, FSM logic is used to provide the injector with rudimentary and programmable computer behavior by integrating a mechanical computer into the injector. This FSM mechanical computer (FSMMC) and the Programs IN Grooves (PING) is a sui generis realization of FSM logic. The various parts of the present embodiment make up the FSMMC hardware and the textured patterns on the injector housing, ampoule and the airlock adaptor make up the software or PING program. The FSMMC and PING do not use any electricity and cost virtually zero to implement. Additional cost-saving can be realized by reducing the number of mechanical parts required to perform the functions of the present embodiment in the same manner. The PING Replicator System is also used to manufacture and reproduce in quantity and will be discussed later.

Figure 12:
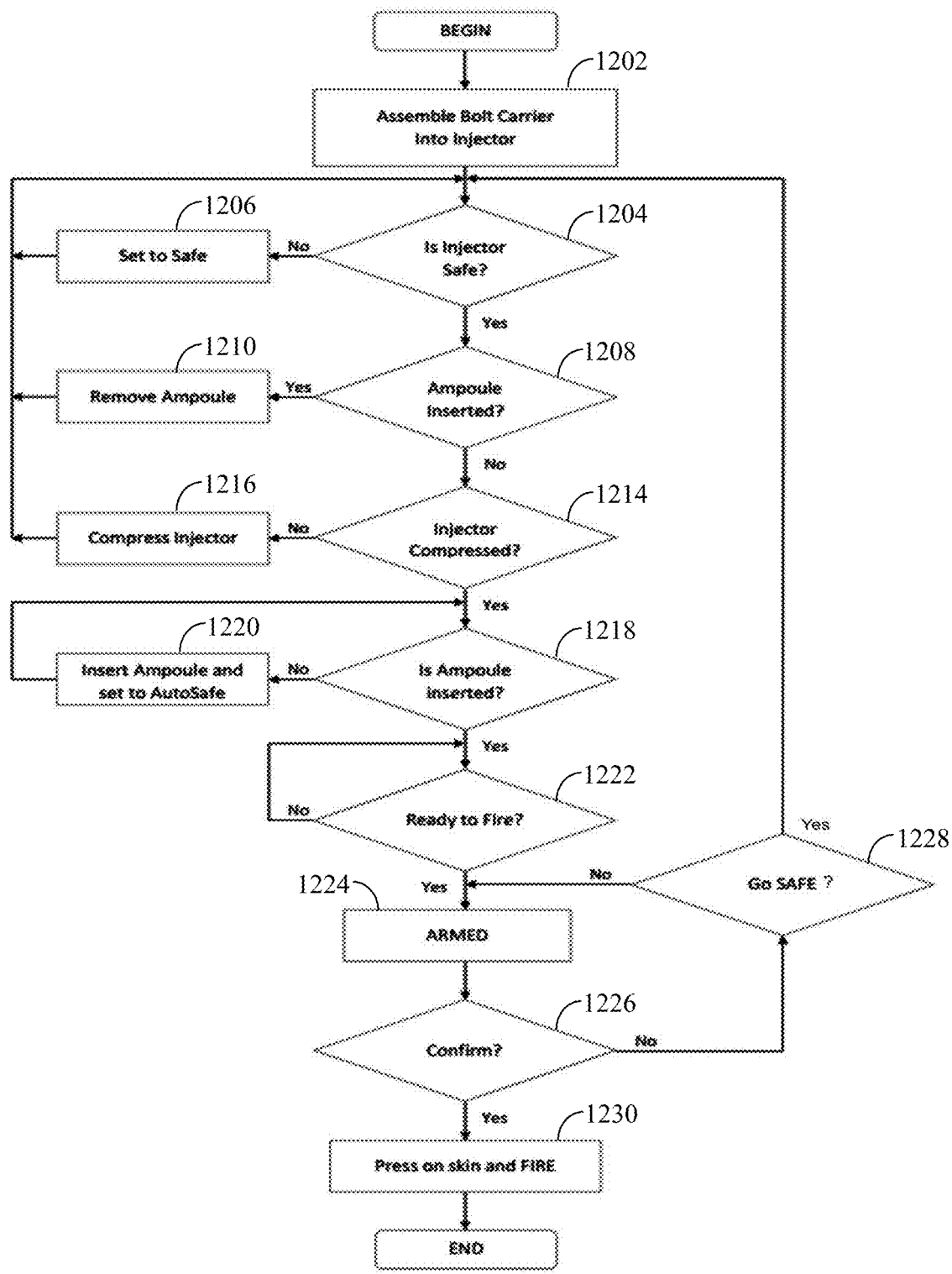
FIG. 12 depicts a flowchart of finite state machine logic operation in accordance with the present embodiment.

Referring to FIG. 12, a flowchart 1200 describes programmed operation of the present embodiment. At step 1202, the needle-free injector is assembled by putting the bolt carrier into the injector housing. If the injector is not safe 1204, it is set to safe 1206. If the ampoule is inserted 1208, it is removed 1210. And if the injector is not compressed 1214, it is compressed 1216. Thus, when the injector is set to safe 1204 and the ampoule is removed 1208, the injector is compressed 1216. If the compressed injector 1214 does not have an ampoule inserted 1218, the ampoule is inserted and set to Autosafe 1220. When the user is ready to fire 1222, the injector is ARMED 1224 and status of the injector is confirmed 1226. If the user decides to change the status to SAFE 1228, processing returns to determine whether the status of the injector is safe 1204. If, on the other hand, the user does not decide to change the status to SAFE 1228, then the status remains ARMED 1224 and, when confirmed 1226 and the user is ready to inject, the needle-free injector in accordance with the present embodiment is pressed on the skin and FIRED 1230. In this manner, the operation of the FSMMC in accordance with the present embodiment is realized.

Physical Realization of a Finite State Machine

Figure 13:
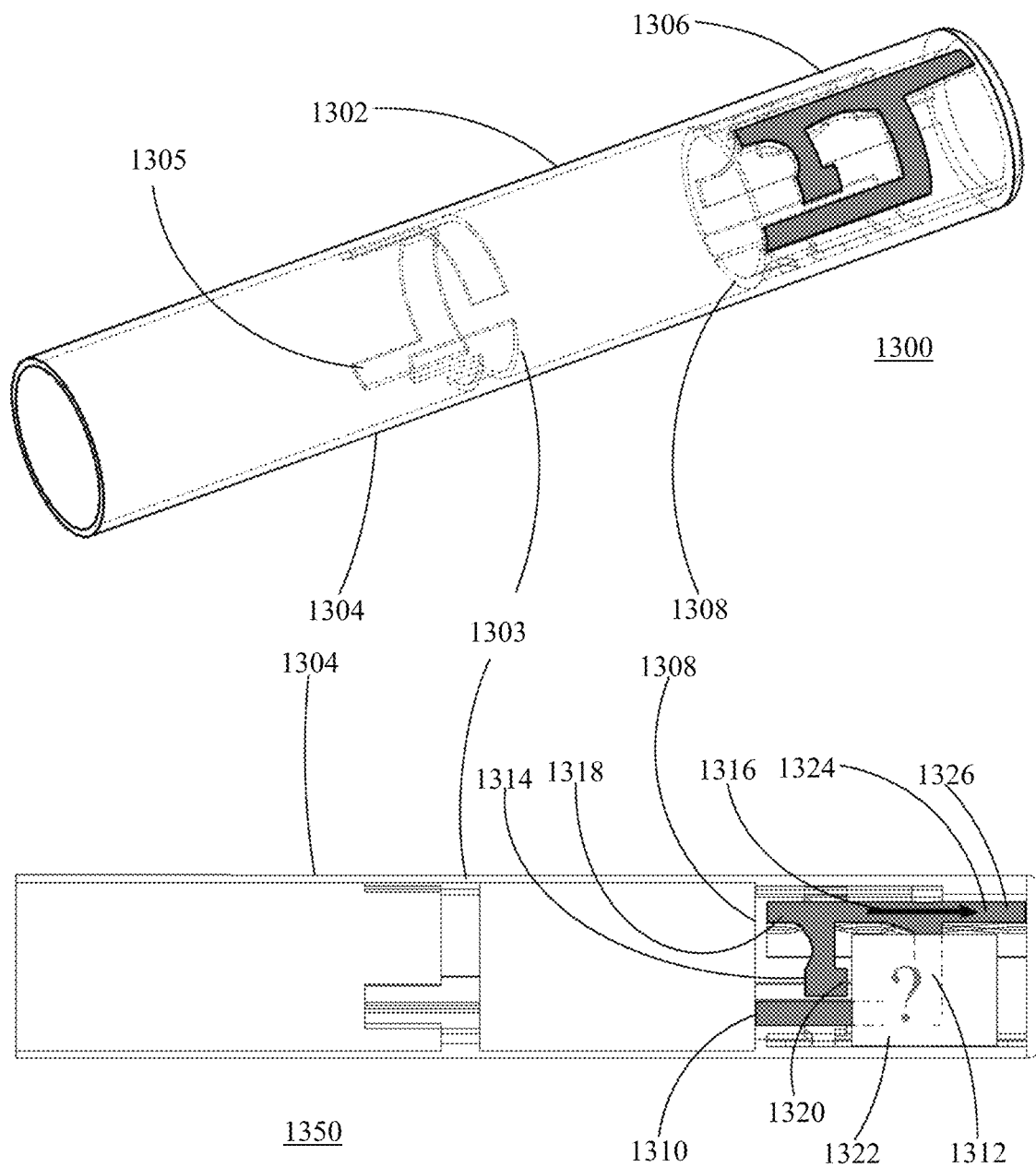
FIG. 13 depicts a perspective view and a planar view of the physical realization of a finite state machine in the injector in accordance with the present embodiment.

Referring to FIG. 13, a perspective view 1300 and a planar view 1350 depict the physical realization of a finite state machine in accordance with the present embodiment by illustrating textured patterns 1306 containing the PING programs and various pathways, a password area, a firing ring and a wall. Although the external surface 1302 of the cylindrical housing 1304 is featureless by design, the inner surface of the housing is filled with textured patterns 1306 and the surface of the bolt carrier is also patterned with the sprockets 802, 804, 806, 808, 810, 812, 814 (FIG. 8).

Sprockets are small shaped protrusions on any surface of the housing, the bolt carrier or the ampoule. Some of them are used to navigate through the inner surface of the housing (e.g., sprockets 812 and 814 are two navigational sprockets). Another purpose of these sprockets is to make physical connections, for instance to connect the bolt carrier to the housing the sprockets 812 and 814 prevent the bolt carrier from falling out of the housing. Another purpose of these sprockets is to provide structural reinforcement (such as in sprockets 802, 804 and 806) to the thin housing or to reduce kinetic friction when the bolt carrier slides in and out of the housing. A structural sprocket is exemplified by sprockets 808 and 810. A row of sprockets traversing coaxially into the housing is a wall, as compared to rings which traverse the housing in a radial manner. A wall is used to structurally reinforce the housing 1305 or bolt carrier (not shown). It can also be used for external device guides. The wall can also be used as a one-sided transition pathway. Another purpose of sprockets is to provide password and key coding capability. Yet another purpose is to communicate with another device. Sprockets can be used singly or in combination. Another purpose of sprockets is to form an impediment to an action or to perform an action. Yet another purpose is to provide FSMMC and PING functionality to be discussed hereinafter. The examples given in this document are not fully inclusive or the use limited to only such use as described.

Grooves 1306 can be extruded or intruded on any surface of an apparatus to provide transitional pathways 1310, 1312, 1314, 1316, 1318, 1320, 1322, 1324, 1326. Although grooves are preferred in accordance with the present embodiment, the physical implementation can be pipes, tubes or any convoluted shape or first predetermined structure to move a sprocket or second mechanically coupleable predetermined structure from one position to another. Similarly, the FSMMC sprocket or its equivalent can be any shape or size or inverse and used either singly or used as a plurality of sprockets to work with grooves or their equivalents.

These transitional pathways allow the sprockets to move from one FSM state to another so as to perform different injector functions. These sprocket or sprockets are controlled to move only within the grooves and moving from one groove to another as determined by the connected order of the grooves. It is not possible to jump out of the groove unless the sprocket and/or groove is programmed to do so, as in a multi-dimensional sprocket/groove program. Multiple concentric tubes can be used for the sprockets and grooves in different tubes to interact with one another between tubes. In the airlock adaptor described hereinbelow, three concentric tubes with sprockets and/or grooves are linked to the single tube of grooves on the injector by way of the ampoule and the bolt carrier. Different textured patterns can be programmed during manufacturing to adapt the injector to different applications as and when needed. For instance, mirroring the groove pathways can convert a right-handed injector for left-handed use. The FSM logic does not limit the number of virtual sequenced states or transitions but one can quickly run out of physical space to make more grooves on the injector.

Figure 17A:
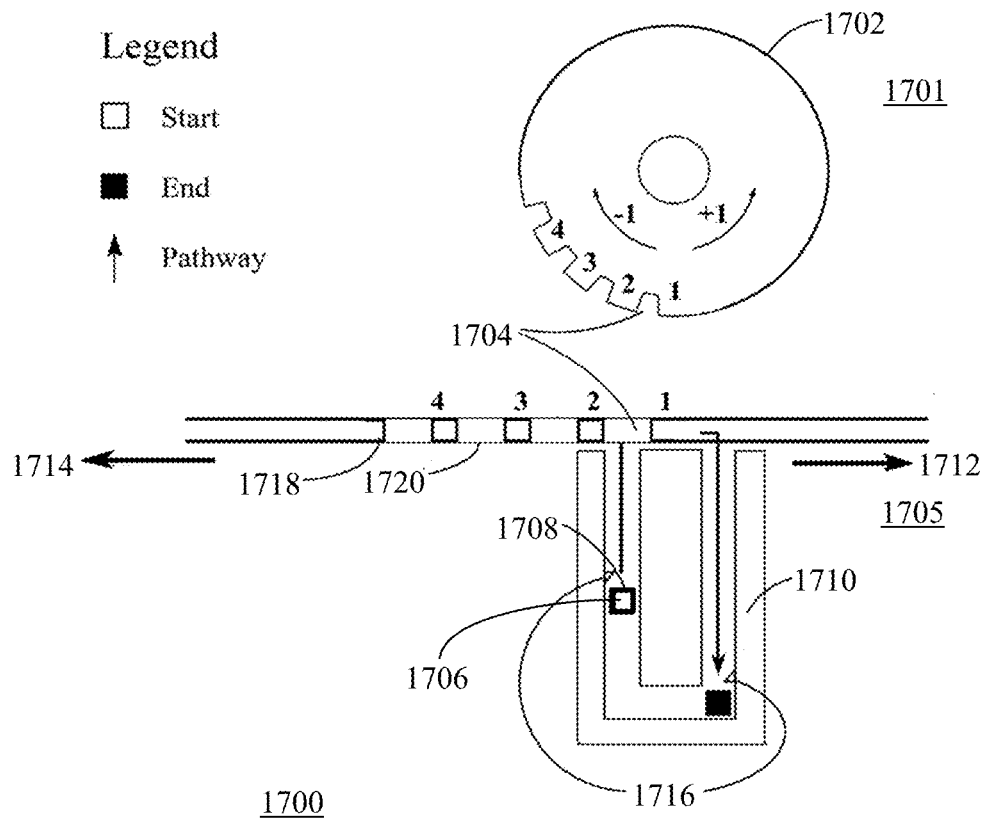
FIGS. 17A, 17B, 17C, 17D and 17E, illustrates views of an arithmetic ring in accordance with the present embodiment, wherein FIG. 17A comprises a top planar and a side planar view of the arithmetic ring with a stop at four count.
Figure 17B:
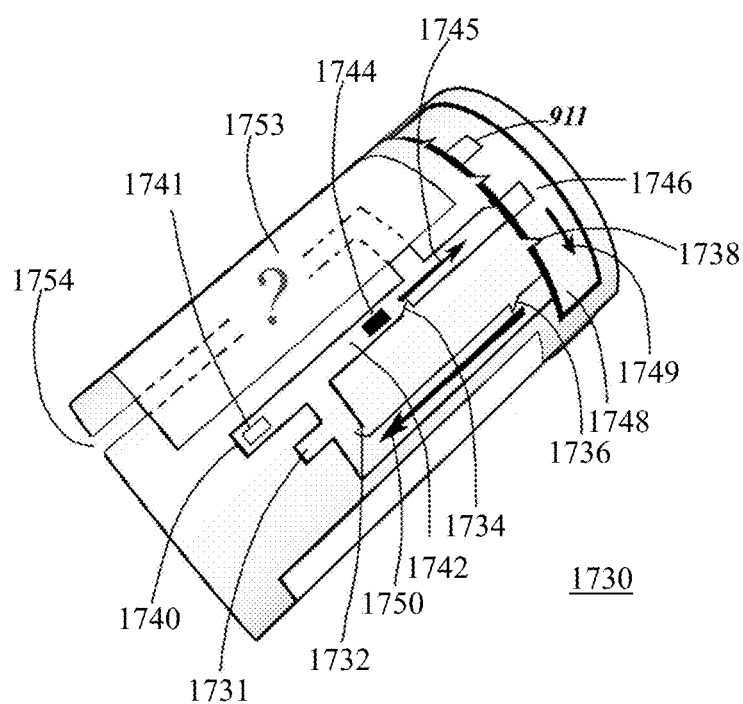
Figure 17C:
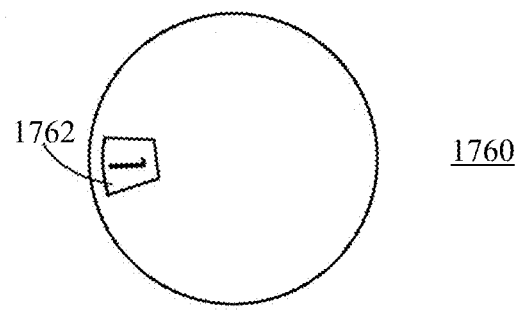
Figure 17D:
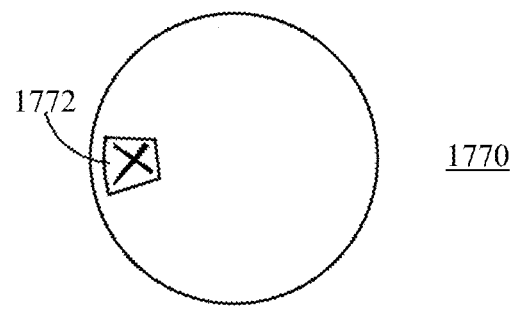
Figure 17E:
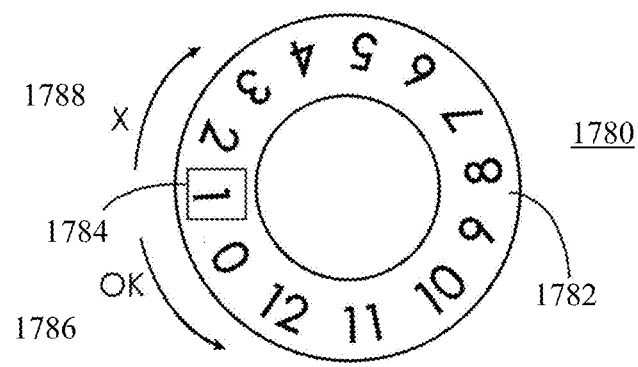

Rings are complete or partial arc shaped ring-like protrusions along any surface of the housing or bolt carrier to be used in conjunction with the grooves and sprockets and any part that form the FSMMC. They can be rotating rings like an arithmetic add-one ring, (see FIG. 17A) or a conditional ring (see FIG. 18A).

The difference between the embodiment of the arithmetic ring and the embodiment of the conditional ring, is the use of the "conditional" pathway (FIG. 18A) which allows the sprocket to "branch" away or "go to" another pathway if a condition is met, in this case the condition where the arithmetic ring counts to three and go to a stop pathway. In computer lingo, IF (COUNT==3) THEN GOTO STOP. The present embodiment provides for alternative embodiments of arithmetic and conditional operations to be performed. Using this method, those skilled in the art of computer science can design alternate implementation of pathways to perform other conditional pathways and logic operations.

Figure 18A:
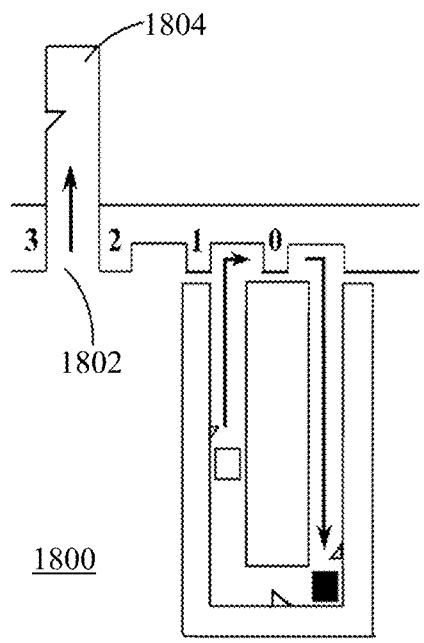

The ability to perform a conditional operation is important to differentiate present embodiment from conventional devices. The ability to perform a conditional operation makes a computer "Turing Complete" and, therefore, the PING Replicator System, the FSMMC mechanical computer and the PING software language is Turing Complete because conditional operations can be performed as shown in FIG. 18A and described hereinbelow.

These rings can be located at different positions along the housing to perform a function. Using the views 1100, 1150 in FIG. 11, the purpose of the firing ring 904 is to activate the latch 1102, 1152 when the proper skin pressure is detected by the pressuring sensing ring 1016. The purpose of the retardation ring 1008 is to provide a counter pressure for the pressure spring 712. Thus the pressure sensing ring 1016 and the retardation ring 1008 sandwich the pressure spring 712 between them.

Purpose of Sprockets, Grooves and Rings

The housing, sprockets, grooves and rings form the hardware of the FSMMC. By sliding the bolt carrier in and out of the housing while simultaneously twisting clockwise or anticlockwise to move along one or more combined pathways, multiple functions can be performed by the injector. These sequential transitional pathways are akin to a three dimensional maze on the inside surface of the housing. Sprockets, grooves and rings can be on any surface of the ampoule and injector, as well as on any interconnecting device, such as the airlock adaptor.

Broadly speaking, a FSMMC in accordance with the present embodiment includes a first device such as the bolt carrier which has one or more first predefined structures (e.g., sprockets) formed at a surface thereof and a second device such as the housing having one or more second predefined structures (e.g., grooves or rings) formed at a surface thereof (e.g., the inner surface of the housing). The first predefined structures mechanically interactively couple with the second predefined structures such that a predetermined series of movements of the first device in relation to the second device defines one of a plurality of functions of the FSMMC. The predetermined series of movements corresponds to one of a plurality of predefined constrained sequence of movements defined by the mechanically interactive coupling of the first predefined structures with the second predefined structures to change from a first finite state of the FSMMC to a second finite state of the FSMMC.

Figure 14:
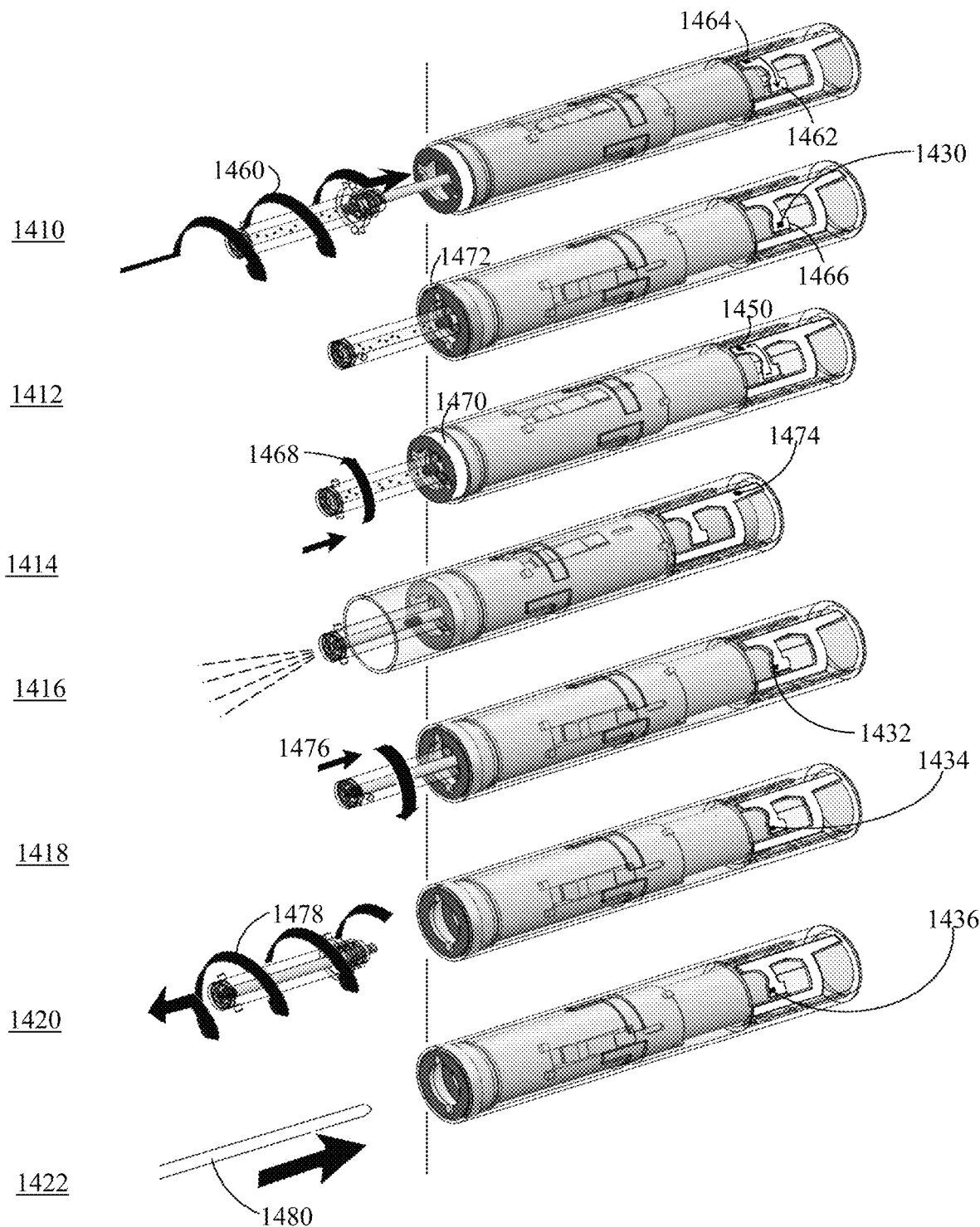
FIG. 14 depicts multiple semi-transparent perspective views depicting operation of the ampoule and the injector and auto safe interlock features in accordance with the present embodiment.

There is a distinction between pathways and positions. A pathway is a path travelled by the sprocket to move from one position to another. In FSM logic, the pathways are used for transitions and the positions are finite states of the FSMMC. FIG. 14 depicts semitransparent perspective views 1410, 1412, 1414, 1416, 1418, 1420, 1422 of the injector to illustrate various positions on the inside surface of the housing relative to the external action taken. Safe positions are 1430, 1432, 1434 and 1436 and armed position 1464. Moving from a safe to armed position is a transition along a pathway 1450.

Referring back to FIG. 13 shows a selection of the pathways. The assemble/disassemble pathway 1310 is used by the bolt carrier sprocket for assembling and disassembling in and out of the housing. This pathway also prevents the bolt carrier from falling out of the housing without the use of extra parts to secure the bolt carrier. Reversing through the same pathway allows the bolt carrier to be disassembled and removed.

The transfer pathway 1312 is used by the injector to laterally transfer from one pathway to another. For instance, to transfer the sprocket from the assembly pathway 1310 onto the firing pathway 1316. Another example is the transfer from the armed position 1318 to the safe position 1314 using an armed to safe transfer pathway.

To administer an injection, and still referring to FIG. 13, the user moves the sprocket from the safe position 1314 to the armed position 1318. This cannot be done without an ampoule as there is no hand hold to push or pull or twist the bolt carrier. When the ampoule connected to the injector moves the injector from the safe position 1314 to the armed position 1318, the injection is ready to be administered. When the housing is pushed into the skin, the bolt carrier sprocket travels along this firing pathway 1316, the sprocket continues along until the injector automatically injects and the sprocket continues further into the over reach pathway 1324 and arrives at the end position 1326 where the sprocket cannot travel any further. Releasing the injector allows the pressure spring to return the sprocket back to the armed position 1318. A small notch is set into the rear of the safe position 1314; this small notch is the safe lock position 1320 which prevents any bolt carrier twisting movement while in this position. The dotted [?] area 1322 is a special area which will be explained later.

Referring back to FIG. 14 use of the pathways combined with physical actions and safety cues is depicted. The perspective view 1410 shows a filled ampoule being screw inserted into the injector with a clockwise motion 1460. Assuming the injector spring is already compressed, the view 1410 depicts the injector in a wrong safety position for illustrative purposes. With the firing spring compressed, the injector should be in the safe state 1462 and not in the armed position 1464 because the compressed spring can be accidentally discharged, for instance when you intentionally insert your finger into the housing.

Using a normal screwing motion to insert the ampoule, this screwing motion will simultaneously twist the bolt carrier inside the housing and move the injector into the safe position 1462. This is the auto safe ampoule interlock. If the injector is previously already in the correct safe position, the injector will continue to remain in the safe position.

The perspective view 1412 shows the injector in safe position 1430 with an ampoule inserted. If the ampoule is placed on the skin and the housing is pushed to perform an injection, the sprocket will remain in the safe position 1430 and the injector will not inject. With skin pressure, the sprocket will now be against the rear of the safe position 1430 where it is depressed against a notch 1466. The notch 1466 is a safe lock and prevents the bolt carrier from twisting and remains in the safe position even if there is a forced injection with a twisting motion. It can be seen that the various pathways are shaped and the grooves are not straight lines. The detail in contouring grooves in the perspective views is purposeful. A small notch for instance translates to a safety feature that may require an additional part using conventional design methodology. The detail contouring forms part of the programming methodology. Unlike conventional software programming where everything is virtual, the FSMMC and PING are inherently non-virtual and the program itself becomes the actuator or is actuated upon. The programs written in PING are very action oriented where each start position transiting to an end position is associated with a physical action, not just at the start or end positions alone, but also how the pathway transition is executed. For instance, a screw driving pathway depicted in FIG. 18G produces a screw driving action.

The perspective view 1414 shows the hand motion of simultaneously pushing and twisting the ampoule with an anticlockwise twist motion 1468. This moves the bolt carrier into the armed position 1450. At the same time, the bolt carrier 1470 protrudes slightly out of the housing 1472. Compare this with the housing 1472 in the view 1412 where the housing 1472 is flush with the bolt carrier in the safe position 1430. In the armed position, the protruding bolt carrier 1470 provides a visual cue by way of a red ring visible from both the distal and proximal end. This allows the armed warning to be visible whether you are injecting others or self-injecting. Also as the injector can be used in a variety of grip holds (e.g., pen, stab, push, pull, thumb press), the safety ring is visible to the holder's field of view as well as the recipient's field of view.

It should be noted that in the event the ampoule is not sufficiently tightened into the bolt carrier, the pushing and anticlockwise twisting motion 1468 will twist the ampoule off the bolt carrier instead of arming the injector. Although the bolt carrier is friction free, the pushing action engages a back pressure from the pressure spring so that the ampoule twists off. This provides an ampoule improperly fastened safety interlock. In addition, for zero visibility situations, the protruding safety ring 1470 can be slightly depressed to provide a springy tactile cue to signify that the injector is armed.

The perspective view 1416 shows the motion of injecting with the housing sliding over the ampoule. The sprocket is seen to ride higher up the firing channel and continues until it reaches the end 1474. By this time, the latch has already been intentionally released about halfway up the firing pathway and the injection is completed even before the sprocket arrives at the end if a slow stroke motion is used. By continuing to push and move the bolt carrier into the housing, kinetic energy is stored in the skin pressure detecting spring 712. Releasing pressure on the ampoule tip on the skin reverses the direction of bolt carrier which continues to remain connected to the surface of the skin due to the back pressure from the stored kinetic energy. At this moment, the ampoule tip is still making skin contact until such time as there is no more pressure on the skin and the ampoule tip leaves the skin surface.

The perspective view 1418 shows the hand motion of push and clockwise twist 1476 to return the injector to safe after injecting. Note that the red ring is retracted back into the housing giving a visual cue that the injector is now in safe mode. Note also that if the injector is not returned to safe, the compression spring cannot be latched by a forward reloading box. This is another safety interlock provided by the injector.

The perspective view 1420 shows the hand motion of removing the empty ampoule with an anticlockwise twist 1478. Note that the shape of the safe position 1434 prevents the bolt carrier from moving away from its safe position during a pull and unscrew motion. In the unlikely event that it did move to the armed position, the compression spring cannot be latched. The ramrod in the reloading box is of fixed length. Without the back pressure of the safety position to lock the bolt carrier, the bolt carrier will retract further into the housing when the ramrod is inserted so that the latching mechanism cannot latch.

The perspective view 1422 shows the use of a front loading ramrod device 1480 to compress the spring to prepare for the next injection. Note that the injector has to be in the safe position 1436 for reloading to take place as explained earlier. To repeat the injection, fill another ampoule or use another pre-filled ampoule module and begin the sequence from the perspective view 1410.

Although sequenced operations are used in other needle free injectors to sequence the same order of Safe, Armed and Fire operation, they are limited in their functionality if sophisticated electronics are not used (for instance, password protection). Also, they are not able to synchronize their safety interlocks beyond the basic function of performing an injection. The method of using FSMMC in accordance with the present embodiment allows the injector to sequence itself as well as sequence an external device when connected to the injector. The safety interlocks of both devices are also simultaneously synchronized to each other while each device carries out its own safety interlocking precautions. This is explained in greater detail hereinbelow.

Figure 15:
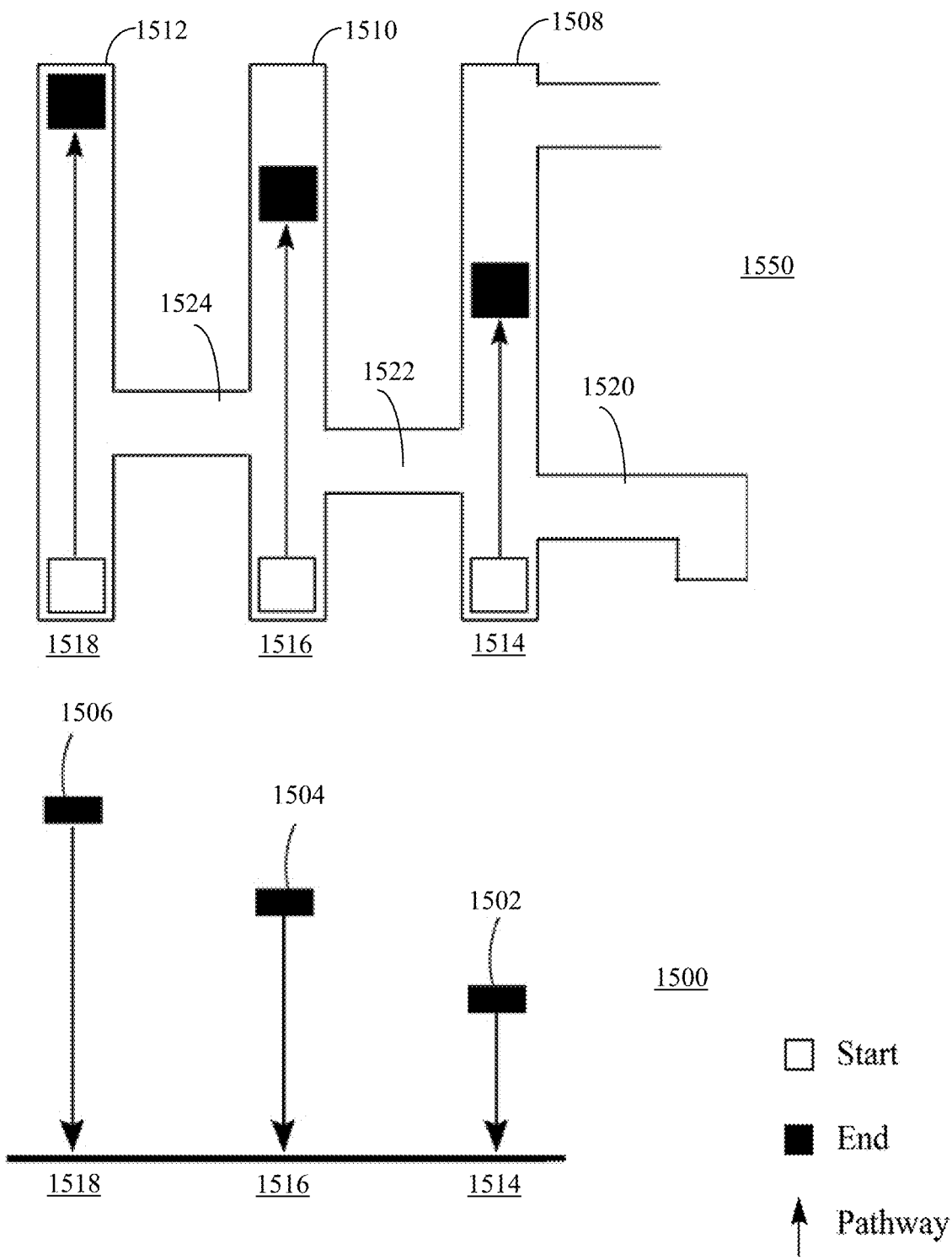
FIG. 15 depicts diagrams of operation of selectable firing channels in accordance with the present embodiment.

In accordance with the present embodiment, a change setting pathway feature is provided to allow multiple pressure sensitive settings of the injector to be selectable in a single injector. In this manner, the orifice to skin pressure required for administering the injection can be selectably increased or decreased. Referring to FIG. 15, diagrams 1500, 1550 illustrate how the three firing rings (arcs) 1502, 1504, 1506 are aligned to three corresponding pathways 1508, 1510, 1512 to provide a different ring to latch distance 1514, 1516, 1518. The different settings allow the same injector to perform Intradermal (1502, 1508, 1514), Subcutaneous (1504, 1510, 1516) or Intramuscular (1506, 1512, 1518) injections. A fourth or fifth pathway or more can similarly be programmed on the housing.

Using Hooke's Law, $F=k \cdot X$, and a proper selection of the spring, the selectable settings can be predetermined. Using transfer pathways 1520, 1522, 1524, a user is allowed to move between each of the injection types. A staggered transfer pathway provides a tactile feedback of more resistance as you move from ID to SC to IM.

In accordance with the embodiment as shown in view 100 of FIG. 1, with a single injection type configuration, there are three rings as shown in FIG. 10: the firing ring 1016, the pressure sensitive ring 1014 and the retardation ring 1008 on the bolt carrier. In the embodiment as shown in the view 120 of FIG. 1, with three selectable injection types ID, SC, IM, there are five rings: three firing rings 1502, 1504, 1506 (FIG. 15) and the pressure sensitive ring 1014 and the retardation ring 1008 on the bolt carrier 710 as before.

Password

A feature of particular note is the implementation of a password or anti tamper pathway to discourage use or to discourage disassembly in accordance with the present embodiment. This feature is also useful as an anti-counterfeiting method by matching the password to the manufacturing lot number. These pathways can be combined with others to cause the bolt carrier to lock up or go into a dead end or go into an endless loop. In accordance with the present embodiment, these pathways are placed in the [?] zone 1322 (FIG. 13) because these pathways are unknown to anyone else besides the programmer (unless, of course, you destroy the housing).

Figure 16A:
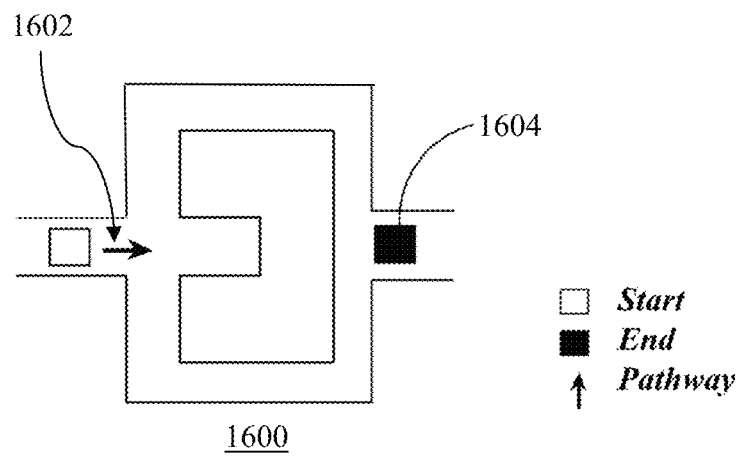
Figures 16B, 16C:
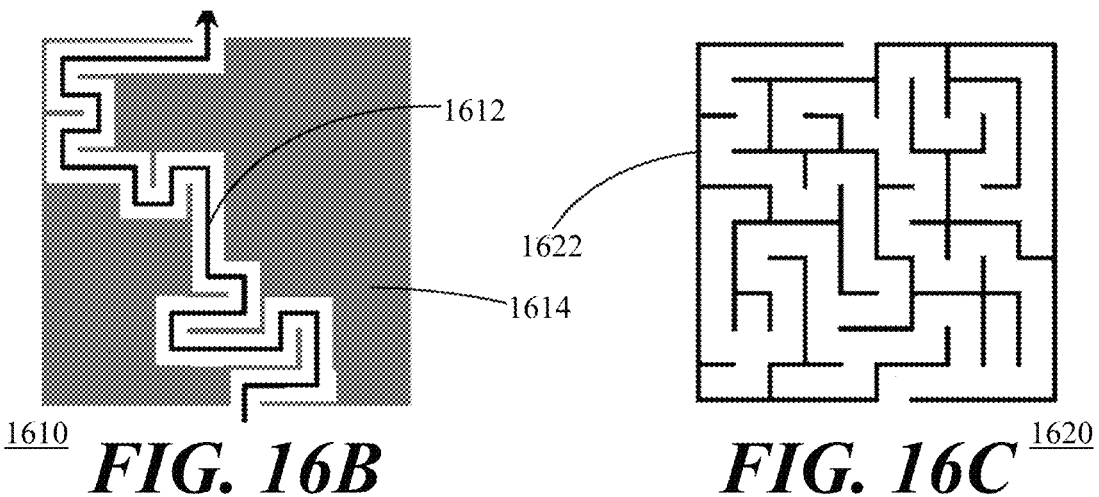
Figure 16D:
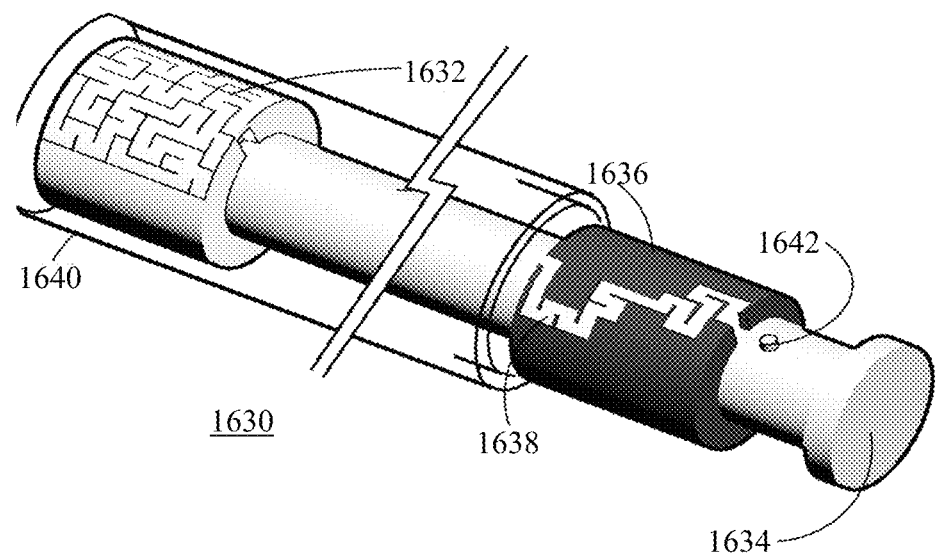

Referring to FIG. 16, comprising FIGS. 16A, 16B, 16C and 16D, two examples of the password pathway feature in accordance with the present embodiment is illustrated with diagrams 1600, 1610, 1620 and a perspective view 1630. A pathway 1602 can be navigated to the exit with relative ease by someone who knows the pattern or password. One of the passwords for the pathway 1602 is twist right while pulling, twist right until stop, twist right while pushing and exit 1604. If one does not know the password, it is considerably more difficult as you can be caught in an endless loop.

Pathway 1612 represents a maze 1622 of pathways and is considerably more difficult to navigate, and the password can easily be forgotten over time. It is also easy to get lost in the maze 1622. Complex passwords can be used to prevent unauthorized use by children, teenagers and thieves, or for tactical situations where the injector cannot be used by the opposition against you without knowledge of the password. The password can be made as simple or as complex as the situation demands and a one-time password can be easily user programmed using a PC or mobile software application for a 3D printer build. The bolt carrier can be disassembled from the old housing and placed in the new housing build with a new password. A wrong password pathway can also be programmed to misfire the injector or lock the injector down a dead end one way.

An example password key is shown in the perspective view 1630. To make the maze 1632 easy to navigate, a novel password key 1634 is provided in accordance with the present embodiment to allow simple navigation through the complex maze. The password key 1634 is a hollow tube key with a sleeve 1636 attached. The key 1634 goes over the ampoule with cylindrical sleeve 1636 over the key 1634. On the sleeve 1636 is a one for one copy of the password map 1614, except that it is visible from the exterior. The solution through the maze 1632 is imprinted as a series of connecting slots on the sleeve 1636 to match a solution path 1638 through the maze. This is much like a car gear shift with a cut out template through which one can move the gear stick around. Using the outer sleeve slots on the key 1636 as a guide, align the sleeve 1636 and the key 1634 to the injector 1640. While holding the sleeve 1636, manipulate a pin 1642 through the slotted sleeve 1638 to reproduce the same one to one motion to navigate (unlock) the maze 1632 inside the injector 1640. This solution also allows for ease of operator assembly and disassembly during manufacture and recycling. Password key sleeve information can also be sent through the computer network to be remotely 3D printed, or reprinted if the key or key sleeve is lost. Alternatively, the password map 1614 can give visual clues for manual manipulation. This password protection and password key method and embodiment can be used with any mechanical device, and is not limited to needle-free injectors.

FSMMC Arithmetic, Logic and Memory

A preprogrammed disable after a predetermined number of injections can be done by incorporating an arithmetic ring pathway as shown in FIG. 17. FIG. 17 includes FIGS. 17A, 17B, 17C, 17D and 17E and illustrates in planar views 1700, 1760, 1770, 1780 and perspective view 1730 an apparatus and operation of the preprogrammed disable after a predetermined number of injections in accordance with the present embodiment. An arithmetic ring 1702 is a rotating ring in a top planar view 1701 and a side planar view 1705 with notches 1704 to match a sprocket 1706 at a position 1708. Each time the sprocket 1706 makes a clockwise rotation from 1708 to 1710, the sprocket 1706 rotates the notch 1704 on the arithmetic ring 1702 once to the right 1712, rotating the arithmetic ring 1702 counterclockwise. The notch symbolized by the numeral "1" is moved to the right and a new notch symbolized by the numeral "2" now takes over the position. This is an add-one operation in accordance with the present embodiment. If the sprocket 1706 is moved another time from 1708 to 1710 clockwise, the numeral 3 now takes over the notch position and we have performed another add-one operation. Rotating the sprocket transition in an anti-clockwise direction from 1710 to 1708 will move the arithmetic ring in an opposite clockwise rotation to perform a minus-one operation 1714. To prevent an infinite, add-one, minus-one situation, one-way gates 1716 are used to allow movement of the sprocket 1706 in only clockwise movements. A one-way gate is provided by a narrowing of the channel 1732, 1734, 1736, 1738 (exaggerated in the perspective view 1730) to allow the sprocket 1706 to be hindered in moving in a reverse direction. The arithmetic ring 1702 is depicted with blocked notches from number four onwards 1718 so that it is unable to count further—that is it stops after four 1720. This arithmetic ability can be combined with other pathways so that the injector is forced to stop injection after a number of counts.

The perspective view 1730 illustrates an embodiment of a sector-gear-type arithmetic ring programmed into the injector. A position 1740 shows the position of a sprocket 1741 at the armed position. When the sprocket travels into the firing channel 1742, the sprocket now at position 1744 will pass a one-way gate at 1734 and at the same time cause the firing ring to depress the latch (not shown). From this point onwards, the sprocket, having passed the one-way gate, must continue down the firing channel 1745 to complete the injection stroke. When the sprocket arrives at the arithmetic ring and goes into the notch 1746, another one-way gate locks the sprocket inside the ring 1748 so that the only direction the sprocket can move is to rotate the arithmetic ring in an add-one direction 1749. The back pressure from the spring will cause the sprocket to go back down the return pathway the moment the sprocket arrives at the pathway 1750. Numerous one-way gates can be placed through the pathways to restrict the sprocket and the ring from travelling in reverse (e.g., the one-way gates 1732, 1736, 1738). The sprocket can now be returned to the safe position 1731 to be prepared for the next injection sequence. After a predetermined number of cycles allowed by the arithmetic ring, the sprocket is caught in the firing path zone 1745 and prevented to move into the arithmetic ring which now has a blocked notch, nor can it return back to the armed 1740 or safe 1731 positions due to the one-way gate at 1734. The only exit is through the question marked password pathways 1753. Knowing the password key allows easy disassembly of the bolt carrier out through pathway 1754. Rear end planar views 1760, 1770 of the housing show a window 1762, 1772 cut out at the rear of the housing to display the number of injection cycles already performed by the injector. The window 1762 shows the numeral "1" and the window 1772 shows "X" indicating no further injections are allowed. A rear end planar view 1780 depicts an arithmetic ring 1782 with a total of 12 counts individually viewable through a window is shown as a further example of use. The arithmetic ring 1782 has gated rotation which allows incremental counts in a direction 1786 but not in a direction 1788. Attempts to tamper with the device by continuing with the arithmetic rotation at 1749 can be countered by a pathway to prematurely lock the injector or to frustrate the tampering by entering into a game mode maze, the prize being a free multiple use injector. The FSMMC and PING is a programmable system which allows great flexibility, limited only by the amount of memory space on the computer. In other words, the system is limited by the area to make grooves.

The difference between the embodiment of the arithmetic ring and the embodiment of the conditional ring, is the use of a "conditional" pathway 1802 shown in FIG. 18A. Referring to FIG. 18, various pathways for FSMMC operation in accordance with the present embodiment are shown in views 1800, 1810, 1840, 1850, 1860, 1870, 1880, 1890. A conditional branch is shown in FIG. 18A and is similar to the arithmetic ring except for a pathway 1802 for the sprocket to "branch" away or "go to" the next pathway if a count of three is reached by the arithmetic ring. In computer language, this is equivalent to an IF (COUNT==3) THEN GO TO NEXT. To physically stop at the count of three, the NEXT pathway includes a one-way gated dead end 1804 which allows the sprocket to "branch" away or "go to" the pathway 1802 if a condition is met, in this case the condition where the arithmetic ring counts to three, and go to a stop pathway 1804. In computer lingo, IF (COUNT==3) THEN GOTO STOP, where '==' is the C language equal logic operator used here for illustration. Thus, in accordance with the present embodiment, embodiments of arithmetic and conditional operations are advantageously built upon these basic building blocks for more elaborate computation. Using this method, those skilled in the art of computer science can design alternate implementation of pathways to perform a variety of simple to complicated conditional pathways and logic operations.

The ability to perform a conditional operation is important to differentiate the FSMMC in accordance with the present embodiments from prior art mechanical computers. The ability to perform a conditional operation makes this mechanical computer "Turing Complete" and therefore the PING Replicator System, the FSMMC mechanical computer and the PING software language are also Turing Complete.

Figure 18B:
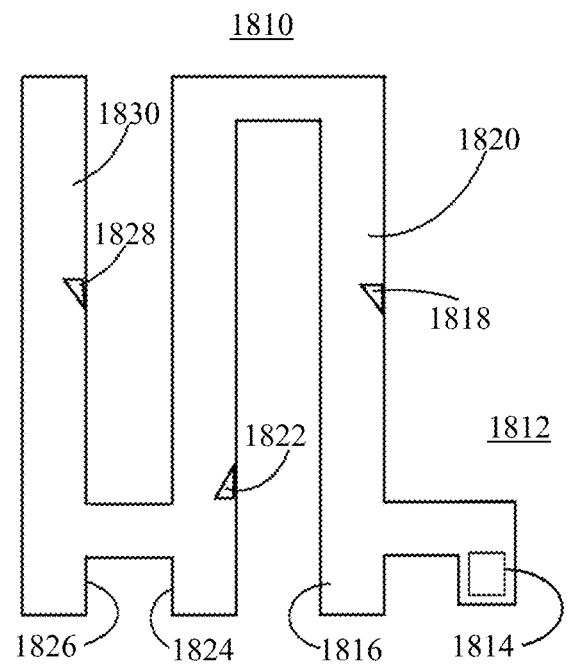
Figure 18C:
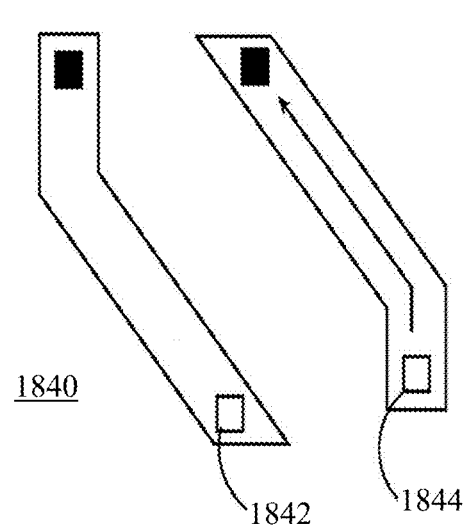

Referring to FIG. 18B, the view 1810 depicts a pathway 1812 showing a simple way to stop at two injections by using a series of safe 1814, armed 1816, one way 1818, fire 1820, one way 1822, safe 1824, armed 1826, one way 1828 and fire 1830 pathways. Repetitive pathways can be grouped together to form a subroutine with a transfer channel to call a subroutine.

As shown in the views 1840, 1850, 1860, and 1870, the present embodiment also provides angular pathways 1842, 1844, 1872, curve pathway 1862 or screw pathway 1882 features so that the bolt carrier can move in angular, non-straight and screwing motions as it travels in and out of the housing tube. This is useful to force the bolt carrier to make twisting motions, thereby indirectly causing the ampoule tip with sprockets to twist by the same amount. In accordance with the present embodiment, this small twisting motion can be used to interlock the ampoule tip to an external device when pushed. Conversely, a pull motion unlocks the ampoule tip by an opposite twist. Another example for use of this advantageous aspect of the present embodiment is to allow a twisting movement to activate a switch or to interconnect a device to an external device or to a robot.

Figure 18D:
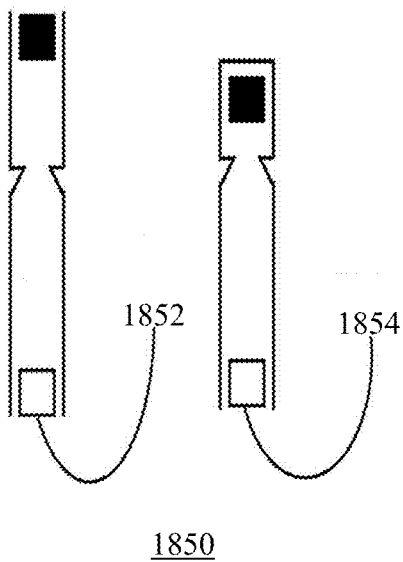
Figure 18E:
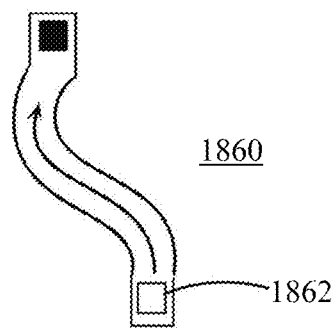
Figure 18F:
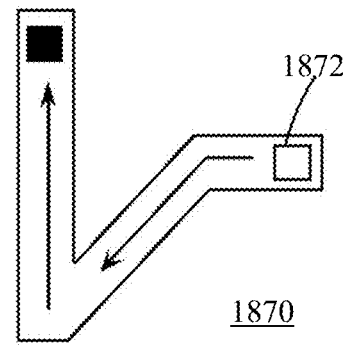

An example of a one-way pathway 1852 and a stop pathway 1854 in accordance with the present embodiment are shown in the view 1850 (FIG. 18D). In the view 1890 (FIG. 18H), a combinatory pathway 1892 is shown which combines the angular pathway 1872, the screw pathway 1882 and the angular pathway 1842. Using the PING Replicator System 2620 depicted in FIG. 26 and discussed hereinbelow, PING software can be designed and written as one would write software on a personal computer in C or C++ code, these programs and program instructions being the mechanical equivalent of FSM logic to CREATE, ADD, DELETE, and EDIT pathways. In accordance with the present embodiment, the software program is in the predefined structures (i.e., in the grooves).

Figure 19A:
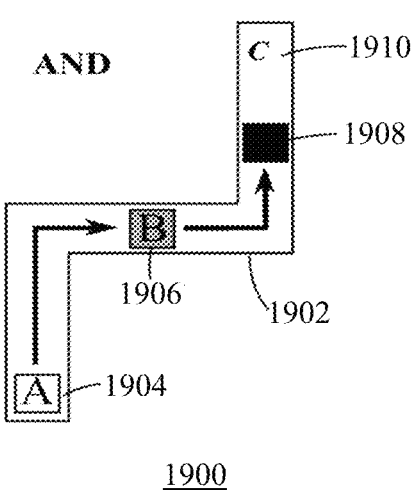
Figure 19B:
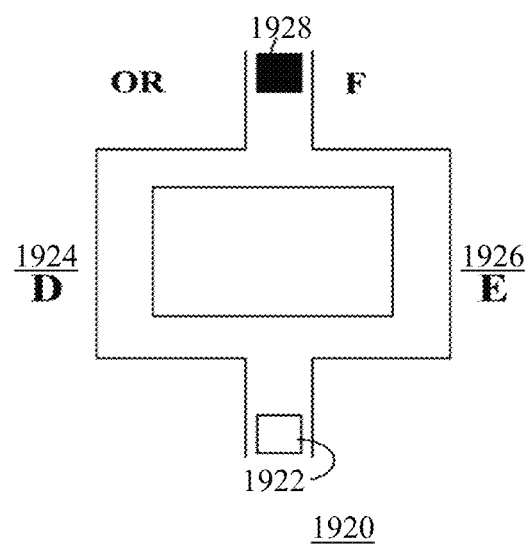

Hereinabove, we have described the use of key codes as a safety feature to match medication, ampoules and injectors. Referring back to FIG. 6A, the master key codes works like an OR gate allowing medication in the ampoule 602 OR medication in the ampoule 604 to pass through. Another example is shown in FIG. 19A, where a view 1900 depicts a pathway 1902 for an AND operation where a sprocket must travel through a pathway A 1904, 1906 AND a pathway B 1906, 1908 before arriving at C 1910. Referring to FIG. 19B, a view 1920 depicts pathways for an OR operation where a sprocket 1922 can arrive at F 1928 using either a pathway D 1924 OR a pathway E 1926. Conventional FSM abstraction does not allow a NOT operation. In accordance with the present embodiment, however, the bolt carrier is retarded by the pressure spring. The default is a NOT fire state because of the back pressure from the pressure sensitive spring 712. Transitioning from the armed position through the fire pathway and stopping the sprocket before the latch is released allows the sprocket to relax back into the armed position, therefore reversing the transition in the opposite direction from fire to NOT fire.

Figure 23:
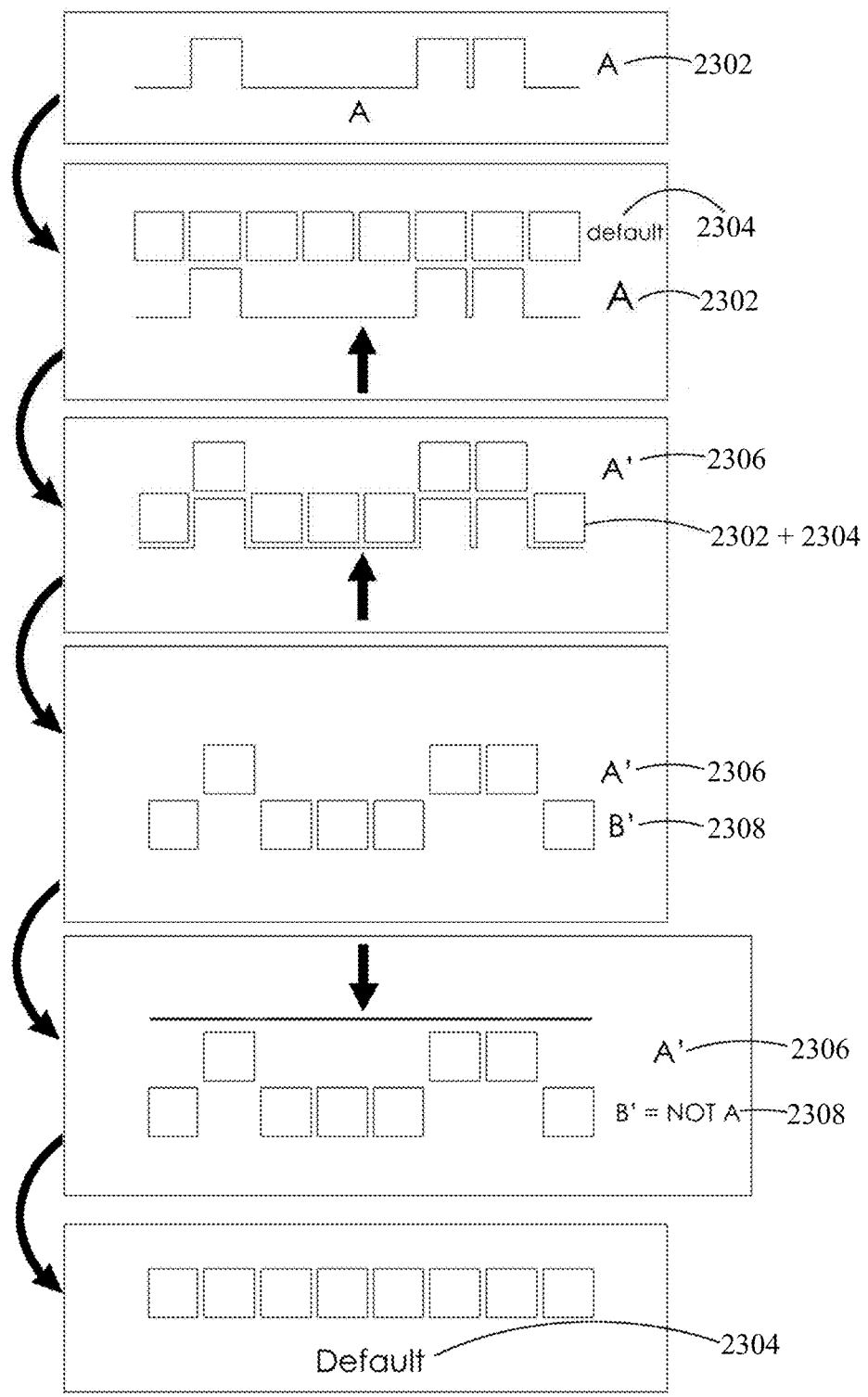
FIG. 23 illustrates a stack of diagrams depicting a byte register NOT logic operation in accordance with the present embodiment.

Another embodiment of a NOT operation is to use a multiple sprocket example as shown in the diagram 2300 of FIG. 23. From the top of the diagram 2300, the sprocket pattern in the sequence from left to right 01000110 represents A 2302, where 0 means no sprocket present and 1 means a sprocket is present. A row full of sprockets 11111111 representing a default 2304 is placed above the A row, i.e., directly above the previous sequence of A 2302. At the next step, the bottom row 2302 is pushed into the top row 2304 to displace the sprockets above thereby generating a displaced row 2306. The displaced row A' 2306 will follow the same row pattern of the original row of sprocketed pattern of A 2302, that is, A=A'. However, what remains behind when the original row of sprockets is removed is the opposite pattern of 10111001 or a NOT A 2308. Thus, the FSMMC in accordance with the present embodiment embodies and performs a memory copy or a memory storage operation as well as a memory inversion operation for the FSMMC. At a later time, all the sprockets of both A' 2306 and B' 2308 can be pushed back together to reset all the sprockets back to their original default position 2304 to CLEAR or RESET the memory. Computer scientists will note that this NOT operation is a physical implementation of BitBitJump and Toga abstraction. From the description of the NOT operation 2300 in FIG. 23, it is also possible to produce a logical EQUAL operation. Taking the A' pattern 2306 and pushing downwards into the B' or NOT A' pattern 2308; if and only if A' 2306 is EQUAL to A 2302, a default pattern 2304 is obtained. If A is NOT EQUAL to A', one or more sprockets will stick out or the default pattern does not result. Thus, logical EQUAL and NOT EQUAL operations can be realized in accordance with the present embodiment.

Conventional terminology calls these single sprockets "bits" of sprockets, and calls a collection of eight "bits" of sprockets a "byte". Therefore, the FSMMC in accordance with the present embodiment presents a byte wide memory location which can be used as a register to sequence further instructions or simply used as memory to contain data. Repeating many of these sprockets and grooves provide more program registers and more memory. An alternative embodiment is to "stack" these memories or registers using physical sprockets and grooves to, using computing terminology, "push" and "pop" the stack. By doing so, the left parenthesis "(" and the right parenthesis ")" operators are embodied as well as a "list" for list processing.

This NOT logic operation is pinnacle in differentiating a mechanical computer and a mechanical calculator. The logic operators AND, OR and NOT that form the basis for Boolean Algebra, proposition logic and De Morgan's Law applies equally to the FSMMC and PING of the present embodiment. The ability of the injector to perform the AND operation "insert ampoule AND put the injector to auto safe" exemplifies this. Another example is "open the airlock portal" AND "set the injector to Auto Arm" to "fire". De Morgan's Law would invert the meaning of the second example to "close the airlock portal" OR "set the injector to Auto Safe" to NOT "fire". It must be appreciated that without Boolean logic, it is possible to arrive at a state where the injector is fired with the airlock portal closed. Using Boolean algebra allows assurance that both the injector and the airlock adaptor have synchronized safety interlocks. The ability to perform Boolean logic sets the needle free injector in accordance with the present embodiment apart from all conventional needle free injectors. In addition, the ability to perform Boolean logic sets the FSMMC in accordance with the present embodiment apart from all prior art mechanical calculators and "mechanical computers".

Figure 19C:
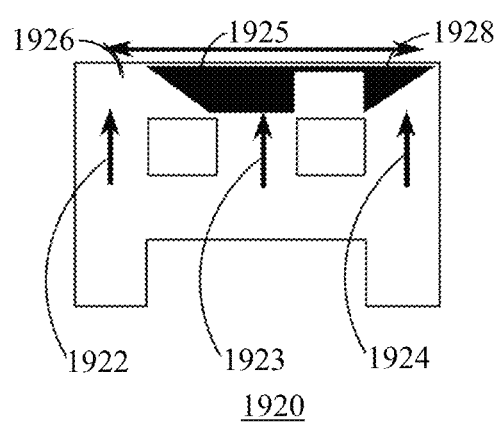
Figure 19D:
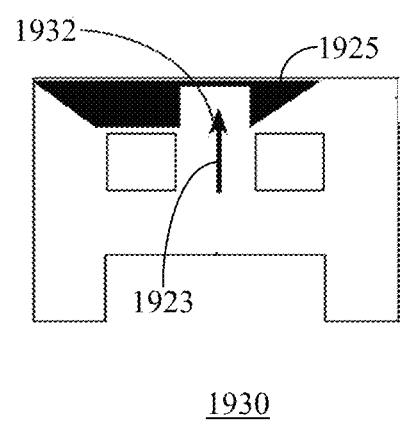

Views 1920, 1930 in FIGS. 19C and 19D depict pathways 1922, 1923, 1924 and a trapezium sprocket 1925 sliding right and left on a transfer pathway to move the sprocket 1925 into positions 1926 and 1928. Alternating a pathway from 1926 to 1928 and back will slide the trapezium sprocket 1925 left and right and left and right and so on. This embodies a flip-flop. However, the data cannot be read without interfering with the state of the trapezium sprocket 1925. Using the pathway 1932 allows movement to position 1932 (FIG. 19D) in the trapezoid pathway if the flip-flop is set one way and unable to move into the pathway if the flip-flop is set the other way, without interfering with the state of the trapezium sprocket 1925. In computing lingo, the sprocket 1925 in the pathway has now performed a "non-destructive Read" after a Flip-Flop Write operation. In this manner, the present embodiment provides a mechanical SRAM of one bit.

Figure 19E:
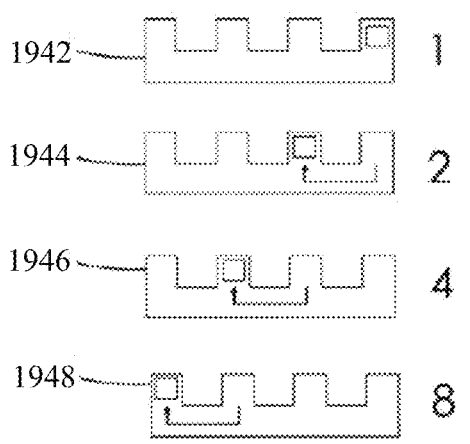
Figure 19F:
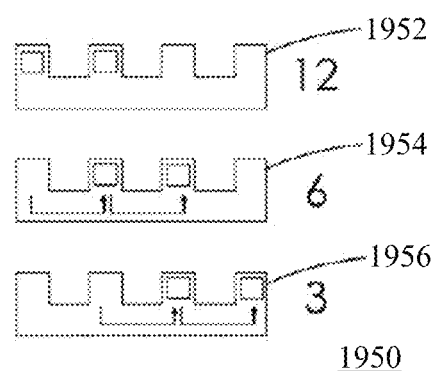
FIG. 19F depicts RIGHT SHIFT DIVIDE operation.

Views 1940, 1950 in FIGS. 19E and 19F depict sprocket operation in a four slotted pathways. The operation 1542 shows the sprocket in the rightmost pathway of the four slotted pathways for the binary representation of "1". Moving the sprocket to the adjacent pathway to the left (operation 1944) produces a binary representation of "2" and is the equivalent of performing a left shift operation. Performing the left shift operation again (operation 1946) results in a binary representation of "4" and again (operation 1948) for a value of "8". In this manner, a multiply operation in accordance with the present embodiment performs a "times 2" multiplication with each left shift operation.

Using two sprockets in the four slotted pathways as shown in operation 1952 of the diagram 1950 defines a binary representation of "12", right shifting both sprockets (operation 1954) results in a binary representation of "6", right shifting again (operation 1956) results in a binary representation of "3". In this manner, a divide operation in accordance with the present embodiment performs "divide by 2" using a right shift operation. Thus, in accordance with the present embodiment, four operators for arithmetic and logic functions MULTIPLY, DIVIDE, LEFT SHIFT and RIGHT SHIFT are provided. By right shifting further, a value of 3 divided by 2 or 1.5 and so on can be conceptually provided. Using prior art computing methodology, the FSMMC and PING can be programmed with a mantissa and exponent and obtain a Floating Point Unit (FPU).

Those skilled in the art of computer science can appreciate the use of prior art methods to program a half adder, a full adder and so on, to emulate not just an ALU or a CPU but a complete computer. Whereas it may not be immediately obvious why a needle free injector would require such intelligence, a needle-free injector in accordance with the present embodiment could be interfaced to a robot for robotic surgery using a rear connector and the safe, armed and fire states could be communicated to the robot using such intelligence. Ampoule states and surface contact states could also be communicated using the intelligence in accordance with the present embodiment. States of a biological surface, an ampoule, an injector and an adaptor programmed with FSMMC and PING in accordance with the present embodiment can be transferred mechanically and not electrically to external devices and throughout the injection system. More importantly, intelligent handshaking and communication between the injection system and the robot or any other interconnected device is made possible in accordance with the present embodiment. No conventional needle free injection technology, mechanical engineering or robotics provides this capability for the simple reason that no fully functional mechanical computer existed before the present embodiment. Conventional mechanical computers are typically single-purpose and do not perform Boolean logic; in fact their operation uses very different principles.

Combining the textured patterns of predefined structures in accordance with the present embodiment using laser cutting to produce micro-grooves and push and pull sprockets pattern can provide two dimensional FSMMC memories. With a creative PING, a pattern similar to QR code with textures of 128 columns and 128 rows of sprockets can provide 16 kbits of SRAM. As taught by conventional electronic technologies, more memory can be obtained with more columns and rows. Whereas all this may require a football field to groove a FSMMC or PING previously, advances in the fields of nanotechnology, laser, plasma and chemical etching today means that micro grooving can be perform; even on the surface of the ampoule's front seal 412, 414 (FIG. 4). Thus, those skilled in the art will realize that FSMMC and PING can be implemented on a micro-scale and nano-scale, such as providing nanoscale grooves, sprockets and rings to provide intelligence to nanobots, or on a macro-scale such as canal locks and corresponding support structures or systems on space stations and spacecrafts.

PING Replicator System

Figure 26A:
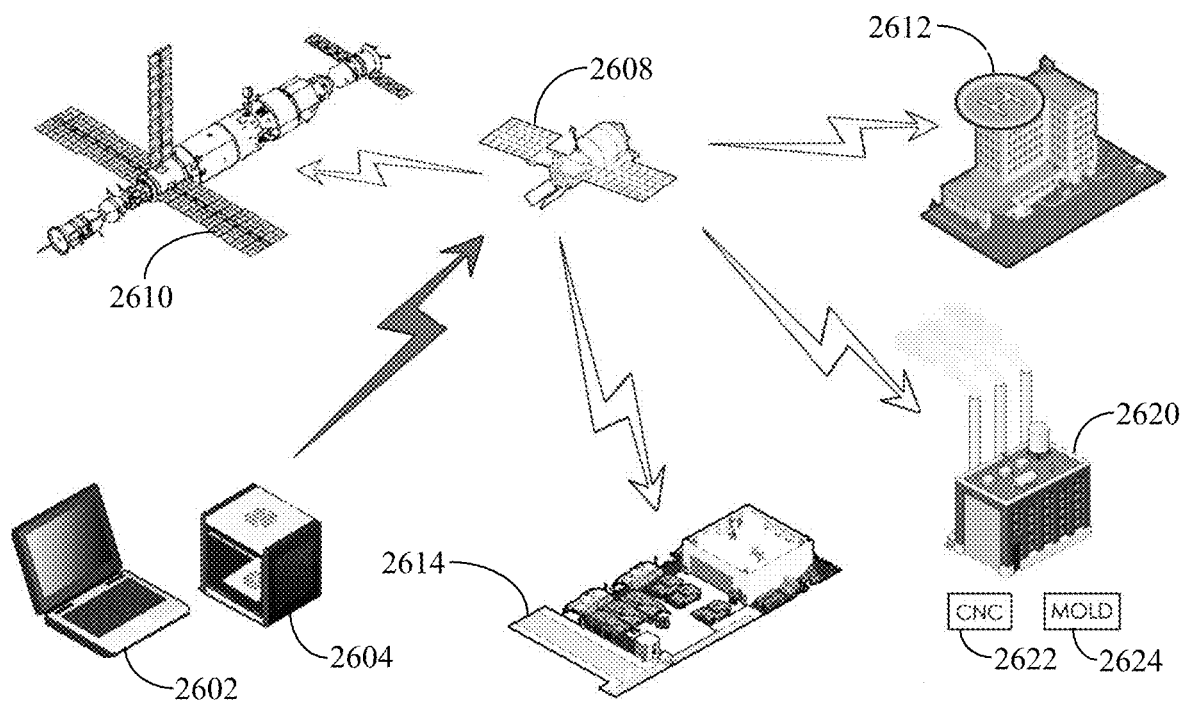

Referring to FIG. 26A, a diagram 2600 depicts an embodiment of the PING Replicator System which includes a programmable device capable of high level programming functions, and that function can include the ability to build or manufacture or communicate the information for such building or manufacture to be carried out. In accordance with the present embodiment, the PING Replicator System is a personal computer 2602 but it may also be a tablet computer, a communication device running applications, a CNC or FMS machine or any device capable of intelligent computing or capable of replicating the FSMMC, PING and PING software. In accordance with the present embodiment, the PING Replicator 2602 is used amongst other things, for all aspects relating to the present embodiment, including design, maze programming, simulation, optimization and so on. The PING Replicator 2602 can be coupled to devices for designing and manufacture of the ampoules and ampoule modules, the injector, the FSMMC, PING programs, including a rapid prototyping 3D printer 2604, mass production facilities in a factory 2620 with Computer Numeric Control (CNC) 2622 and molding machines 2624, suppliers, customers, medical facilities 2612, tactical facilities 2614, outer space facilities 2610 and associates around the world.

Each of the human associates, customers and suppliers providing problems and pathway solutions to be shared so that solutions can be designed and embodied into a hardware, a software and a product. In addition, each of these sites have their own PING Replicator System in a full version or reduced version, to reproduce and share information, design, software, passwords, build files, manufacturing details and so on. For instance, the hospitals 2612 are given the capability to program individual passwords for patients or key code groups of medicine or recycle injectors.

Practitioners are given the capabilities to order parts 2640 (FIG. 26C), to customize their spring parameters and build a "frequently used" program in their housing or to order a custom spring from the spring making machine via the factory PING Replicator 2620.

Pharmaceutical companies with the PING Replicator System can be given free access to key codes for their own use and full capability to customize the injector and ampoule, the FSMMC and PING programs to their medicine. Home users can also benefit by communicating with the PING Replicator. For example, a home user who has lost his password key can be given the capability to print a new key with information provided by the factory 2620. Accordingly, the PING Replicator System 2602 is a product by itself.

Figure 26B:
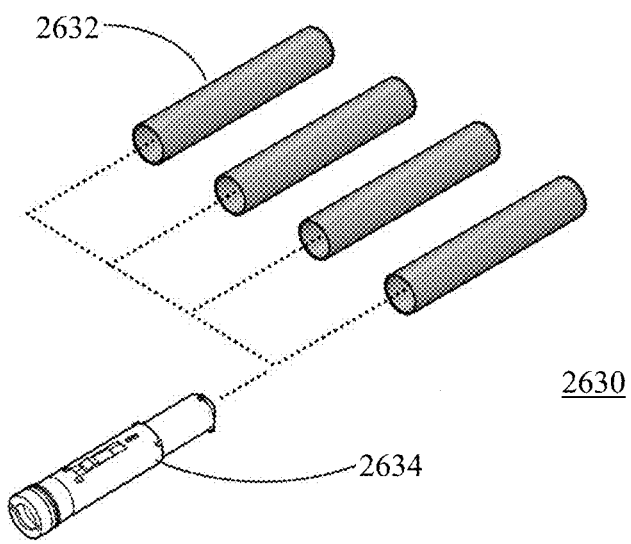
Figure 26C:
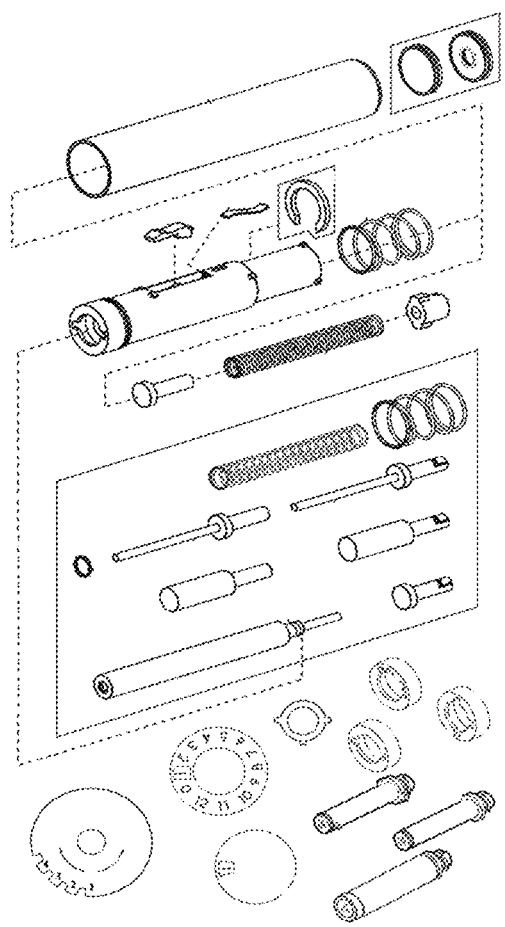
Figure 26D:
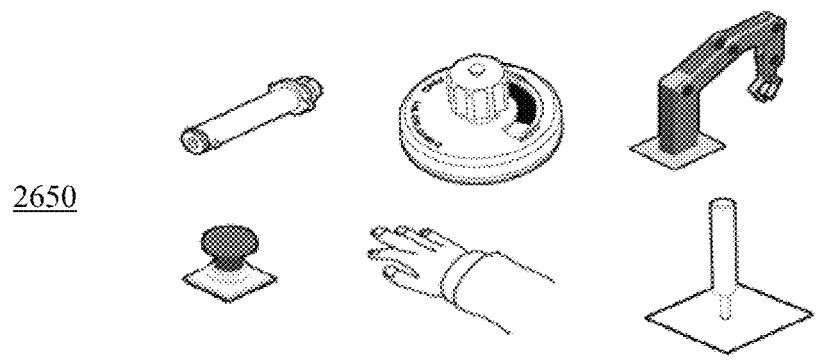

The PING Replicator System is used to a) produce hardware, and b) to write software. Referring to FIG. 26B, software is written by building various injector housings 2632 to hold the software using a 3-D printer 2604 (FIG. 26A) for rapid prototyping or customizing. The hardware is the injector and the software is the textured patterns in the injector housing 2632. The hardware and software perform real world functions using data provided by the positions, the input and output states and actions it receives 2650. Without the PING Replicator System 2602, it is not possible to produce the hardware or the software or the product. Just as the FSMMC and PING are novel embodiments, the PING Replicator System that manufactures the FSMMC and builds the housing containing PING is also novel.

The PING Replicator System is able to build the injector and parts depicted in the illustration 700 (FIG. 7). The PING Replicator System designs and brings together the parts that makes up the injector 2640 and then designs and brings together the various parts that makes up the ampoule 202 (FIG. 2) and the ampoule module 302, 352 (FIG. 3).

However, the collection of parts 2640 are like bricks, sand, door and glass windows which by themselves do not make a house. The parts have to be put together to build a house. The PING Replicator System takes the parts and adds sprockets, rings, walls, and grooves as shown in the perspective view 810 (FIG. 8) and integrates a mechanical computer into various portions of the parts. The PING Replicator System also integrates the sprocketed key code system into the injector 632, 642 and the ampoules 612, 614, 616 (FIG. 6A). The PING Replicator System then writes a software program of grooves 1310, 1312, 1314, 1316, 1318, 1320, 1322, 1324, 1326 (FIG. 13) on the inner surface of the housing and any other relevant surface to connect all the parts together to provide the functionality of a basic injector. The PING program provides the ability to twist and turn the bolt carrier inside the housing and the first function the PING program does is to assemble the bolt carrier into the housing without the bolt carrier falling out 1202 (FIG. 12), 1310 (FIG. 13). Then all the necessary safety features are added like arm, safe, safe lock, auto safe, fire (FIG. 14). Then more features like multi-channel firing (FIG. 15) and a password (FIG. 16D). Add an arithmetic unit (+ and −) (FIG. 17B), Multiply and Divide (FIGS. 19E, 19F)), a logic unit (FIG. 18A and FIGS. 19A, 19B, 19E, 19F and FIG. 23), some memory (FIGS. 19C, 19D and FIG. 23) and the needle-free injector system in accordance with the present embodiment comprises an injector with a Turing Complete built-in mechanical computer; a computer with an ability to follow a written program built by the PING Replicator System. Any computing system capable of doing one or more of these functions in accordance with the manner described herein to produce a FSMMC or PING or a PING program belongs to a PING Replicator System.

Programs IN Grooves or PING

The needle-free injector system in accordance with the present embodiment uses programmed patterned grooves as transitional pathways and positions as finite states using combinatory sequential FSM logic to perform different and separate physical functions. This software is called Programs in Grooves or PING and is stored primarily in the inner surface of the housing of the injector where one housing 2632 (FIG. 26) stores one PING program. The PING Replicator System, the FSMMC or PING is not limited to this embodiment, using one housing to store one program is presented for simple illustration purposes. In accordance with the present embodiment, the textured patterns are not limited to the insides of an injector housing—any surface can be used. Also the location of the maze is not limited to the rear of the housing. Relocating the maze to the forward end of the housing does not change the functionality of the maze though, of course, the bolt carrier shape and sprocket locations would need to be modified accordingly.

PING allows program instructions to be designed, written, coded, amended, added, removed, edited, sequenced in another order, go to, go subroutine and so on, just like conventional C code. The instructions, however, are not in C instructions, but written as mechanical pathway instructions or other textured surfaces of predefined structures. Whereas C codes are virtual codes which need to be transformed into electrical signals to perform an actuating action, the developed PING program comprises actuating codes and every code is a transitional pathway movement from one position to another. Besides, C cannot work without electricity.

Figure 18G:
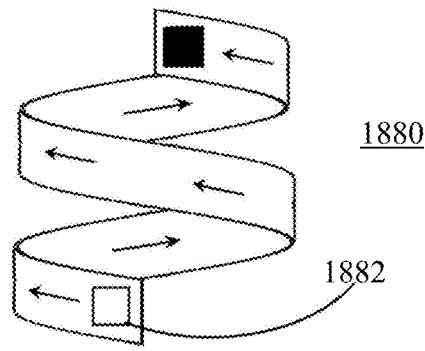
Figure 18H:
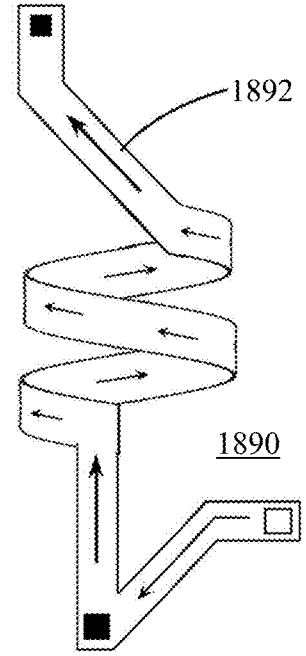

FIGS. 18C, 18E, 18F, 18G, 18H depict physical illustrations of PING coding. Pathway 1842 (FIG. 18C) moves a sprocket from right to left at a 45-degree angle followed by a small vertical movement. Pathway 1862 (FIG. 18E) moves a sprocket in a curvy motion, pathway 1882 (FIG. 18G) moves the sprocket in a screw driving motion and pathway 1872 (FIG. 18F) combines a few pathways to move left, 45-degrees down followed by a vertical motion. Combining the paths 1872, 1882 and 1842 produces the pathway 1892 (FIG. 18H). Using PING, the length of the pathways, the direction, and the pitch of the screw driving pathway can be changed. Also, the scale, the thickness of the pathway or the edge profile of the pathway, replacing one pathway with another (e.g., pathway 1842 with pathway 1844), or change the order of the sequencing of pathways. Every line of "code" will create an actuating movement in the real world, or an actuating movement in the real world will caused the state of the "code" to change.

PING Formal Language

PING programming can be embodied and expressed using a formal language. For instance, "A→B" can be used to define moving a sprocket from A with a "→" as a transition operator, to arrive at a position B. The use of other notations can be used, such as "B→C", "(A→B)+→(B→C)" where a "+→" operator means "pathway connect to pathway" or JOIN operation and an UN-JOIN operation to remove the pathway can be expressed "−→". "(A→B) OR (A→C)" can also be notated, where OR is a logical OR operation. In addition, the following operators can be notated: "∧" AND, "∨" OR, "~" NOT, "<<" for left shift, ">>" for right shift, "*" for multiply, "\" for divide, "(" left parenthesis and ")" right parenthesis and so on. A "==" can be used to denote a logical equal operator, whereas a "=" is an arithmetic equal operation for copying or storing data. The PING formal language can also be notated to include operators "A f(t)→B" or "A f(x)→B" or "A f(p)→B" and so on, to denote that the transition of the sprocket from A to B as a function of time, t defined by the function f(t) or a function of distance x, defined by f(x) or a function of a trajectory or an actuating pathway p, defined by f(p). An example is the screw driving pathway 1882 (FIG. 18G). Those skilled in computer science will readily realize that these few examples above can be expanded upon in the spirit of the present embodiment. By incorporating a time related parameter, the FSM logic can be modified to physically realize modal Linear Temporal Logic (LTL) or Spatial Temporal Logic (STL) or Spatial Temporal Reasoning for nano-robotic Artificial Intelligence and similar general or specific logic and reasoning. This feature is a novel innovation applied to mechanical computers and is unique compared to other mechanical computers. This formal language of PING as described is more than conventional FSM logic and forms a formal language by itself.

FSMMC

In FIG. 26B, the FSMMC is made up of the injector housing 2632, a bolt carrier, sprockets, rings, adaptors and any physical part or parts 2640 that affect the state of the FSMMC. Just like a keyboard and a monitor are input and output devices of a modern day computer, any device that interacts with the FSMMC and PING form part of input and output devices 2650. The ampoule, the airlock adaptor, a robot, an on/off switch, a hand, the surface of the skin for instance can be used to change the various states of the injector and are but one of many FSMMC input and output devices 2650. Interconnected devices can also be FSMMC enabled with their own PING program for synchronization.

So long as any device that uses a FSMMC similar to the way described or uses programs in grooves to perform more than just simple automaton functions such as those programs described herein, the novel methods and devices in accordance with the present embodiment are being used. In particular, if any of the features like arithmetic and logic, a subroutine, a form of memory are used, the novel methods and devices in accordance with the present embodiment are being used. In addition, if the devices use a mechanical password and a mechanical password key, or a communicative means to synchronize the actions between devices or to perform handshaking using mechanical means involving sprockets and grooves, or to perform sequencing and control of needle free injecting technology using a single or combinatory pathway, or selection of multiple pathways or convoluted pathways, the novel methods and devices in accordance with the present embodiment are being used.

The hardware with the software having thus been made capable of being programmed with computer behavior of sequenced control is able to perform functions including, but not limited to, the various arithmetic and logic operations, input/output actions and memory features as previously described. Input actions are user actions and external device actions, while output actions include injecting and interaction with external devices. Compare this to a sample of the FSM flow chart shown in FIG. 12 which states the logical sequences and decisions to be made to perform an injection but by itself does nothing in the real world.

In addition to the novel ability of injecting, the ability to stop after a number of injections and the use of a mechanical password or key code sets this injector and ampoule apart from conventional injectors. This mechanical computer and its associated groove programming are built into and form an integral part of the needle free hypodermic injector in accordance with the present embodiment. Although the needle free injector in accordance with the present embodiment can perform without the FSMMC and PING, it performs with less flexibility, less functionality, less safety interlocks and uses many more parts.

A new set of textured patterns can be manufactured to reprogram the housing to suit different applications while the same bolt carrier 2634 (FIG. 26) is used. The programming can be for a standalone injector or for the injector to be connected with external devices. Using the PING Replicator, hardware and software can be programmed and reprogrammed, added, deleted, edited, joined and so on to behave fundamentally like a computer. Subroutines and previously stored library functions can be added or removed. Using the PING Replicator, pathways can also be contoured or micro-contoured to correlate to the physical actions.

Programming and reprogramming the housing on the PING Replicator using a workstation 2602 may seem to be a mass manufacturing task and a hurdle for most home users. However, any home or office computer or smartphone today can be installed with an application to reprogram the injector housing and to build new programs (the housing) using a high quality 3D printer 2604. Customized housings can be ordered from the factory 2620 using computer networking means 2608. With this application, new programs can be printed at home 2604, at the hospital 2612, in-the-field 2614 or on the space station 2610 using appropriate PING Replicator software in a PING Replicator workstation 2602. The PING Replicator workstation 2602 can be a computer, notebook, mobile phone or any computing or communicating device with program intelligence. Although the housing program can be changed for different housings 2632, the same bolt carrier 2634 is usually reinserted into a new housing without the need for any assembly or disassembling tools. Bolt carrier specification and design can be changed on the PING Replicator but the build is usually factory made due to high tolerance and high impact materials used. Build machinery can be a 3D printer 2604, laser machinery, flexible CNC machinery 2622 and molding machinery 2624, a spring maker, an assembly machine, a labeling machine, a warehousing machine or any machinery with information communicated with the PING Replicator System and cooperating therewith. Thus, customized and application-specific solutions can be easily configured and built with little human intervention. This forms a novel solution whereby needle free injectors, ampoules, adaptors and accessories related to needle free injection are given a flexibility that conventional injectors do not have.

The PING Replicator system can be used on its own or used in combination with other CADCAM programs to perform textured pattern design, optimization, simulation and build amongst other functions to form a total system apparatus. It can also be used for any other matters relating to the injector, ampoule, medication and their associative parts. This software can be used either standalone or used with any associative software programs relating to needle free hypodermic injection or associated external devices. Build and part procurement can also be communicated via the PING Replicator workstation 2602, for instance to order or build new springs or a different propulsion module, to select appropriate multi-orifice ampoules or injector types once the design criteria, optimization or simulation is done.

Information relating to parts assembly of the ampoule and injector can also be communicated to intelligent automated factory assembly machines. Parts 2640 for the FSMMC can be ordered or used to extend the FSMMC logic, including but not limited to parts for an arithmetic ring, a conditional if logic gate, AND, OR, NOT gates, sprocket memory, display pathways, program pathway or any programs associated to PING. Such parts can be physical or virtual or both.

The patterned programs can be written to work with authored patterned programs by others, or combined with a library of patterned programs in the computer or obtained on-line to be used in conjunction with hypodermic injection or other fields of technology, for instance substituting the injector with a laser scalpel. Program patterns are also not limited to being imprinted on a cylinder or flat surface. Any maze modeling or FSM modeling software and parts can be used to provide more PING Replication System functions.

This information allows parameters of the needle free injection system in accordance with the present embodiment to be altered, for instance to program or reprogram the textured patterns or predefined structures. Such information stored on a CAMCAM station can be communicated and used for large scale manufacturing or single build home use. A software SDK for mass production, field build or home use including interfaces to 3D printer technology forms part of this system.

Combining the textured patterns in accordance with the present embodiment with micro-grooving manufacturing technology allows more functionality or programming to be added. For instance, a two-dimensional array of push and pull sprockets as a register and a static memory can be used to store and communicate more information in the future. Using QR code technology, for instance, allows the push and pull 2D sprockets to store memory limited only by the space you have for micro-grooving.

To bring completeness to all this, the physical realization in accordance with the present embodiment is compared to the von Neumann computer architecture in the Electronic Discrete Variable Automatic Computer (EDVAC) report. Von Neumann describes a design architecture for an electronic digital computer with parts consisting of a processing unit containing an arithmetic logic unit and processor registers, a control unit containing an instruction register and program counter, a memory to store both data and instructions, external mass storage, and input and output mechanisms. Using von Neumann's description of a CPU, apparatus adopting the technology in accordance with the present embodiment qualifies as a CPU thereby making a FSMMC operating in accordance with the present embodiment a computer. Some may argue that a Harvard architecture is a better description of the FSMMC because the program memory is kept separate from the data memory.

The use of the PING Replicator System, FSMMC and PING is not limited to needle free injection technology but can be applied to all computational fields and technology using FSM abstractions as well as any computer abstractions that do not use FSM logic, for instance formal verification or formal proof of temporal logic such as linear temporal logic (LTL) or any such abstractions. In LTL, future states of the abstraction of "something" is required to undergo formal verification of whether the software, logic, concept or virtual design is workable. To physically realize this formal verification or formal proof means that other types of logic modal or modelling besides FSM can now be ascertained by physical means. For instance, BitBitJump and Toga can thus be realized.

Virtual logic paths can be realized by emulating them using physical multi-dimensional pathways. Instead of sprockets or grooves, we can use a ball in hand to simulate transitional pathways required to move from one end of a room to the other. However, what is stopping this from happening is all the virtual logic between where your ball is and where your ball wishes to be. The ball can only move within these pathways defined by the virtual logic and to physically realize this, we can create numerous interconnected hollow tubes to define these virtual logic states or positions. For instance, a convoluted connection of tubes constrained by the same virtual equivalent to limit the movement of the ball provides a predefined constrained sequence of movements to get your ball form the start position to the end position. Multi-dimensional formal verification and temporal proofing just means moving the ball from one room to another room filled with another set of convoluted pathways.

A physical formal verification can now be reached (to reinforce a virtual formal verification), if and only if, we can move this ball from the start position to the end position. Naturally, more than one ball and more than one room can be used and more convoluted and shaped pipes or boxes or gizmos can be used to represent the virtual situation. A string or curved bits of wire (the PING program) can be used to restrict the movement of a finger ring or flag or sprocket or any moving device can be used for navigation (the FSMMC). The string becoming the "software" and the finger ring becoming the "hardware". The "data" is a hand or hands or any actuator used to perform a transitional motion along the string. This is an alternative embodiment of a physical realization of the FSMMC, and PING as well. Examples of other mathematical and logic modal systems besides finite state machines include labelled transition systems, Petri nets, vector addition systems, timed automata, hybrid automata, process algebra and formal semantics of programming languages.

It is not the intention of this detailed description to list all possibilities of hardware or programming capabilities but to provide sufficient methods and embodiments to show how FSM logic, or any other logic modal, is not just a virtual abstraction and that a reduction to practice of a Turing Complete mechanical computer and Turing Complete mechanical software program can be so embodied, and means to produce such embodiments are so described.

Finally, such physical embodiments consist of the PING Replicator System, the FSMMC, the PING components in accordance with the present embodiment, and the end result of a needle free injection system consisting of ampoules, injectors, adaptors and accessories using novel features described herein in accordance with the present embodiment.

Multiple Use and Programmable Use Injector

Conventional needle-free injection systems differentiate between single use injectors and multiple use injectors. However, as discussed herein an injector can be mechanically programmable in accordance with the present embodiment. For instance, the injector can be programmed to be used three times and then locked by a mechanical password. However, if the password is known, the injector can be "Reset" for subsequent use or reset by authorized personnel for recycling. Factory passwords and recycling passwords are designed to be very complicated and difficult to break without a password key. Other than factory passwords, user passwords and application specific passwords can be created in accordance with the present embodiment.

As discussed hereinabove, using the integrated FSMMC allows the injector to be programmed at manufacture to be disabled after a second or a third use. This feature is useful to match an injector to a number of dosage treatments (e.g., three or twelve dosages). This differentiates the present embodiment from conventional injector systems.

In a multiple dose treatment, for instance in a hydroporation treatment of facial Marionette lines, two doses could be used for each of the left and right Marionette lines or four doses in total. A treatment kit consisting of four Hyaluronic Acid ampoule modules and a four-time use injector and accessories could be configured for such treatment and after the fourth treatment, the injector is disabled and the whole kit can be disposed of, or the injector can be returned for recycling.

Safety Interlocks

In accordance with the present embodiment, a safety-enhanced needle-free injector system is provided. This safety-enhanced needle-free injector system provides multiple safety interlocks to make the apparatus safe and yet easy to use.

A) Cover

The safety-enhanced needle-free injector system in accordance with the present embodiment uses the cover as a primary safety interlock. With the cover on, the ampoule cannot make contact with skin and the skin pressure sensitive mechanism cannot be activated.

B) Safe to Armed, then Armed to Fire

After taking the cover off, the safety-enhanced needle-free injector system in accordance with the present embodiment uses a further "push and twist left" motion to arm the injector (see 1414, FIG. 14). When the injector is armed, the red ring 1470 protrudes out of the housing. Using a "push and twist right" returns the injector to safe and the red ring 1470 retracts back into the housing.

C) No Ampoule Present Interlock

A no-ampoule detected interlock required by conventional manual triggering injectors is not necessary in a skin pressure automatic triggering injector. In the safety-enhanced needle-free injector system in accordance with the present embodiment, if there is no ampoule connected to the injector, there is no skin pressure and the automatic injection mechanism will not operate. In the Safe mode, an inquisitive finger pushing against the bolt carrier will meet with resistance and the injector will not fire if there is no ampoule connected. Without an ampoule connected, it is extremely difficult to simultaneously push and twist the bolt carrier from a safe to an armed position and then fire without purposeful intent to circumvent the safety.

D) Ampoule Improperly Fastened Interlock

In the safety-enhanced needle-free injector system in accordance with the present embodiment, it is difficult to move the injector from safe to armed if the ampoule is loosely or improperly fastened.

E) Second Safety Interlock

Using PING, the safety-enhanced needle-free injector system in accordance with the present embodiment can be programmed with a second safety interlock coded to a password. No conventional non-electrical needle free injector has this capability.

F) Pressure on Skin Safety Interlock

If there is insufficient skin pressure, the automatic injecting mechanism of the safety-enhanced needle-free injector system in accordance with the present embodiment will not activate.

G) Motion Safety Interlock

If there is insufficient motion to exert pressure on the ampoule to move the ampoule into the housing, the automatic injecting mechanism of the safety-enhanced needle-free injector system in accordance with the present embodiment will not activate.

H) Password Protection Interlock

In the safety-enhanced needle-free injector system in accordance with the present embodiment, the injector can be programmed using PING with a password to be entered correctly before the injector can be activated. A second password can be programmed to re-enable the resetting of the injector after a disabling action. A third password can also be used to enable assembly and disassembly. Detection of a false password can lock the injector. All this is done by PING.

I) Front Reloading in Safe Interlock

If the injector is not in a Safe position, it is not possible for the safety-enhanced needle-free injector system in accordance with the present embodiment to perform a front reloading. If the injector is armed, the bolt carrier will slide into the housing thus preventing the propulsion spring from being latched by a front reloading box. The Safe position provides a back pressure for the propulsion spring to be latched properly. Rear reloading mechanisms provide additional safety eyelets to provide a visual cue of the safety status of the injector. Nevertheless, whenever an ampoule is inserted, the auto safe feature will automatically set the injector to Safe.

J) Application Specific Safety Interlock

Application specific handshaking safety interlocks can be programmed with PING. An example of which is the safety interlocks between the injector and the airlock device as described hereinbelow, or between the ampoule and the injector earlier described using key codes.

K) External Device Synchronization Interlocks

Simultaneous handshaking between two devices is possible with PING. Using the airlock example, the injector is set to auto safe when the injector is locked to the airlock adaptor. This prevents accidental firing when the airlock is closed. When the airlock is open, the injector goes into an auto armed position. This interlock synchronization is described in the section on the airlock adaptor hereinbelow.

L) Key Code Safety Interlock

The key code safety interlock prevents an ampoule to be used with a wrong injector or prevents an injector to be used with a wrong ampoule. The key code safety interlock can also be coded such that a single medication is personalized to the proper injector or a group of medication is linked to a particular injector.

Safety Cues

A) Visual Safety Cue

The red protruding ring 1470 (FIG. 14) near the ampoule end of the injector provides a visual cue allowing the user to see that the injector is armed. When the injector is safe, the red protruding ring is retracted 1472. This safety cue is visible from both the distal and proximal ends of the housing.

B) Tactile Safety Cue

In zero visibility, the protruding ring 1470 of the bolt carrier can be pushed into the housing. The back pressure from the pressure spring on the protruding bolt carrier can be felt indicating that the injector is armed. In the safe position, the bolt carrier is not protruding and is flush with the housing.

C) Pressure Safety Cues

Two pressure safety cues are provided. The skin pressure is coupled with the injecting motion to provide a pressure cue during the injecting stroke. Increasing pressure of the ampoule on skin during the injection stroke also provides a tactile feedback of the injection process. During the setting change process, staggered transfer pathways 1520, 1522, 1524 (FIG. 15) provide a tactile feedback of more resistance as you move from IS, SC to IM settings while still providing some safety distance between the transfer pathway and the latch. An alternative embodiment is to provide individual safeties for each type of injection or to use more or less than three types of settings.

D) Motion Safety Cues

The skin pressure is coupled with the injecting motion to provide both motion and pressure cues during the injecting stroke. Pressure on the injector must be exerted on the skin surface to move the injector by a predetermined distance, for example fifteen millimeters, before the triggering event can occur. This provides a motion cue as well as a pressure cue.

Adaptors and Accessories

Some adaptors are defined and used in accordance with the present embodiment to extend the functionality of the needle-free injector when used together therewith. Numerous conventional adaptors and accessories are available, some of these devices are for users to fill the ampoule with their own medication and to cock the injector after each use. For example, to compress the injection spring, one conventional device uses the edge of a table, another uses a levered box, and yet another uses a simple ramrod.

Restraining Adaptor

A restraining adaptor is a mechanical restraining device to be used in conjunction with needle free pressure sensitive injection in accordance with the present embodiment. The restraining adaptor uses a combination of push, pull, twist and angular retardation effects to bring and maintain the injection orifice to surface contact by using mechanical means for the entire duration of the injection or injections. The use of all these restraints are not limited to automatic triggering jet injectors but can be used by any type of needle free jet injector and even adapted for use with syringes with needles. And although the described embodiment utilizes a hand grip with top and bottom ring handles, any shaped hand grip can be used.

Hydroporation Procedure

Hydroporation is a procedure for using a high pressure injectable jet for penetration through the skin surface pores for aesthetic treatments. Although this is primarily what all jet injectors can do, hydroporation involves the combined use of appropriate injectable, process, method, equipment and time intervals for optimal treatment. Various hydroporation procedures have been developed by Sascha Mörl and Ping Derg Chuang to be used in conjunction with the needle-free injector in accordance with the present embodiment. Some of these procedures are only effective when used in accordance with the present embodiment, or less effective when used with other jet injectors. The use of such procedures, methods or devices is not limited to aesthetic applications alone and can be applied to any type of needle free injection application.

Figure 20A:
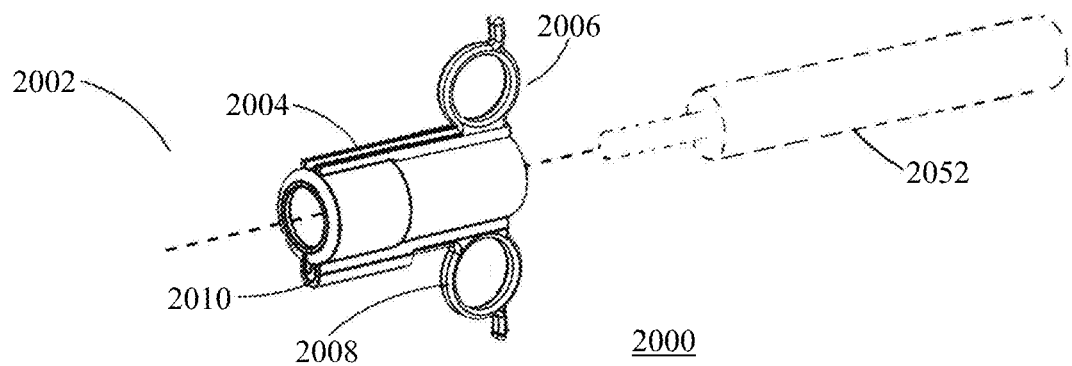
Figure 20B:
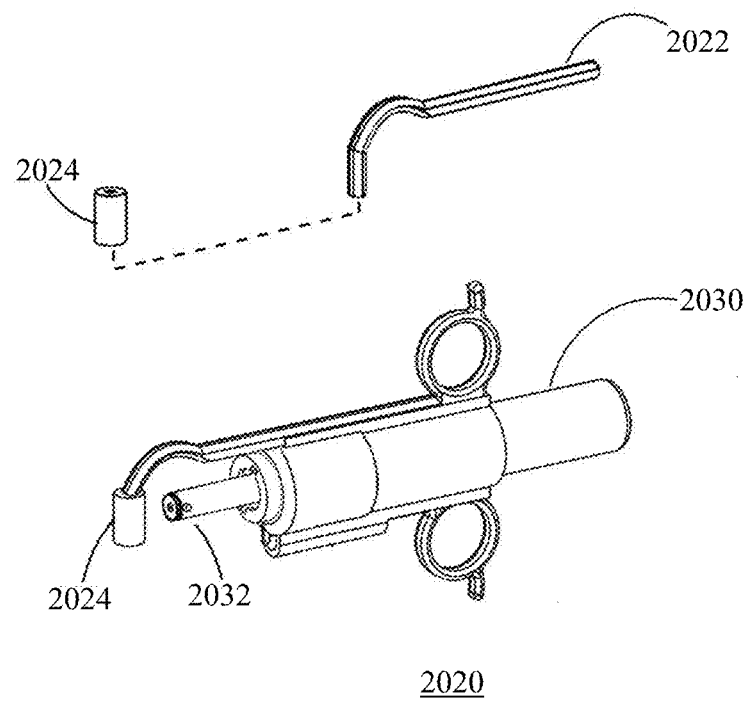
Figure 20C:
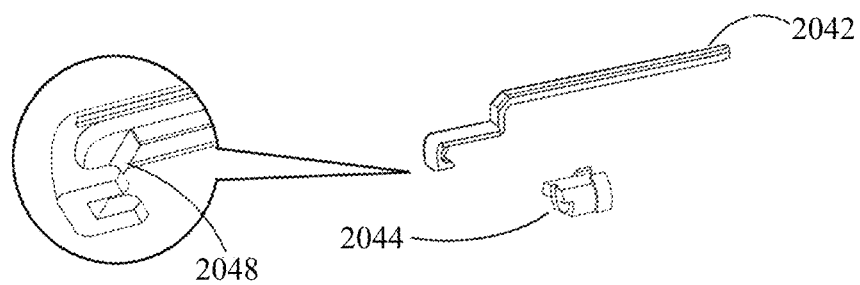
Figure 20C:
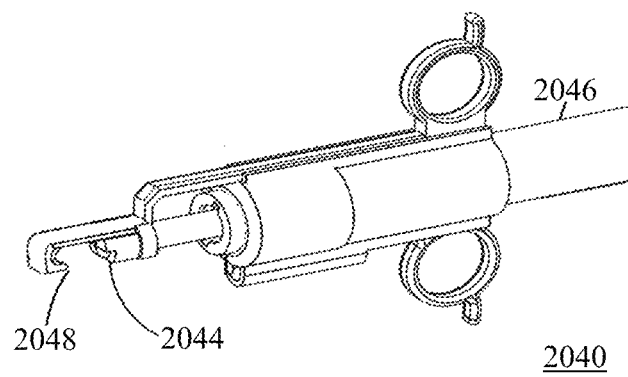
Figure 20D:
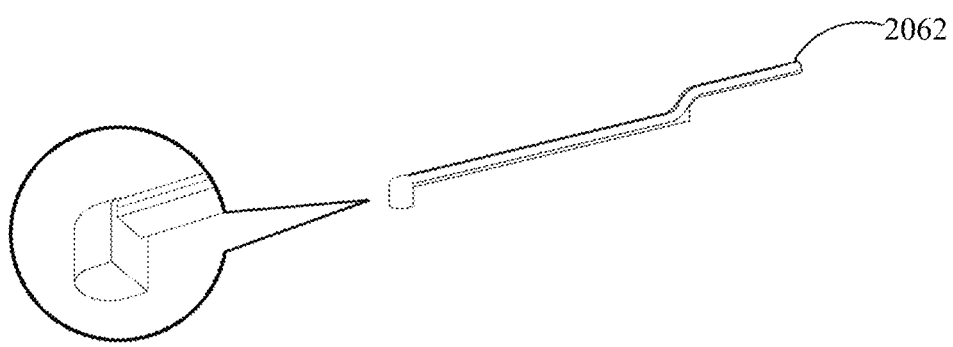
Figure 20D:
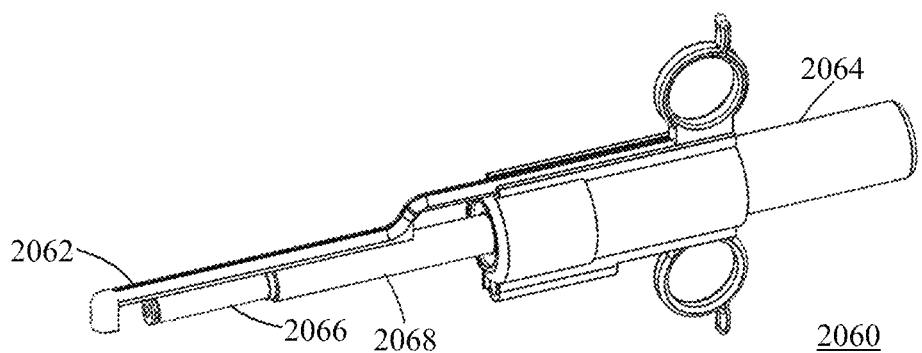

Referring to FIG. 20A, a perspective view 2000 depicts a restraining adaptor 2002 consisting of a holder body 2004, a top handle 2006, a bottom handle 2008 and an integrated return spring assembly 2010 with a dotted outline of the injector 2012 coupled with the restraining adaptor 2002 for use therewith. FIGS. 20B, 20C, 20D depict perspective views 2020, 2040, 2060 illustrating a selection of restraints for use with the restraining adaptor 2002 including a hook 2022 with a hook cushion 2024 (FIG. 20B), a pincher 2042 with a step edge aid 2044 (FIG. 20C), and a long flat restraint 2062 (FIG. 20D).

The perspective view 2020 (FIG. 20B) shows the fully assembled ready to use restraining hook adaptor with ampoule and injector assembly 2030. The ampoule 2032 is filled with a dose of Hyaluronic Acid. The integrated return spring assembly 2010 prevents the injector from falling out of the front of the holder body 2004. The hook cushion 2024 is inserted onto the hook restraint 2022 to provide a back-pressure cushioning effect during injection.

Figure 21A:
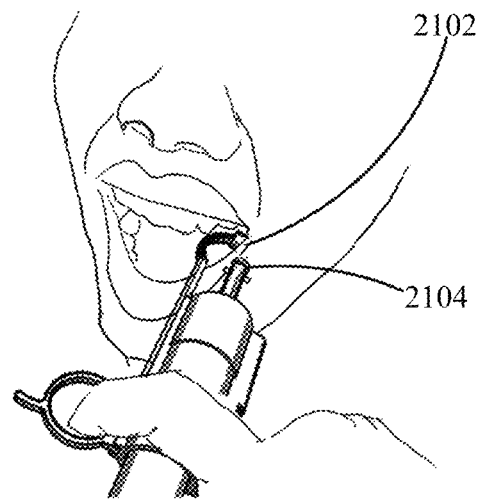

Referring to FIG. 21A an illustration 2100 shows the fully assembled hook restraining adaptor and injector being used for hydroporation treatment of Marionette wrinkle lines. The assembly is positioned with the cushioned hook restraint 2102 inserted into the mouth to provide a back support for the injection. The injection is performed at an orthogonal angle to the skin 2104 which is sandwiched between the ampoule and the hook restraint. The administering of the Hyaluronic Acid (HA) is done automatically when the optimal skin pressure is reached. This is done when the practitioner exerts pressure on the housing with his thumb with a combination of push and pull actions to move and pull the skin surface towards the orifice of the ampoule. The return spring assembly allows the practitioner to make any repositioning adjustments easily. An ampoule with a standard front seal 408 (FIG. 4A) provides all the necessary tactile skin interface and the restraining cushion 2024 provides the rear hook support within the oral cavity. At this juncture, the uncompressed wall to wall skin dimension is six millimeters or less and the area around the lips are sensitive to excess pressure. A light-touch skin pressure profile is pre-programmed into the injector and a low propulsion force spring is configured for use. Too high a propulsion force will cause the HA to penetrate through the wall of skin and enter into the oral cavity. In accordance with the present embodiment, an optimal Mörl-Chuang skin pressure and propulsion pressure profile can be configured for a range of cocktail injectables with different viscosity and injection depth requirements.

It can be appreciated that the skin of a 65-year-old male and that of a female in her late 20s has very different skin texture and wrinkle issues. A treatment plan is typically prescribed by the practitioner upon examining the skin. Providing the practitioner with a selection of propulsion springs for in-the-field configuration to suit his purposes provides a distinct advantage over conventional injectors. In addition, conventional mechanical injectors do not allow fine tuning of a depth profile for the injectors. In accordance with the present embodiment, the skin density can be manually manipulated by compression of the skin tissues. A tightly compressed column of skin provides higher resistance and a tighter cross sectional profile to the jet stream as compared to a lightly compressed column of skin. With the ability to manipulate this skin compression, procedures can be optimized in accordance with the present embodiment to direct the depth resolution of the jet stream by programming different skin compression pressures using the FSMMC and PING. Conventional devices are incapable of doing this. U.S. Pat. No. 8,066,662 to Azar refers to a user defined parameter of pressure applied to the skin surface, however Azar refers to the jet stream pressure applied to the skin surface, rather than the skin compression pressure—two entirely different parameters. Azar does not have a skin pressure sensitive sensor in its apparatus and the apparatus is primarily for non-contact orifice jet streaming.

Figure 21B:
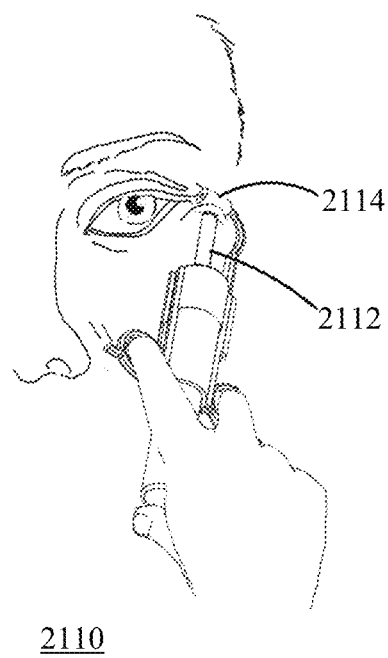
Figure 21C:
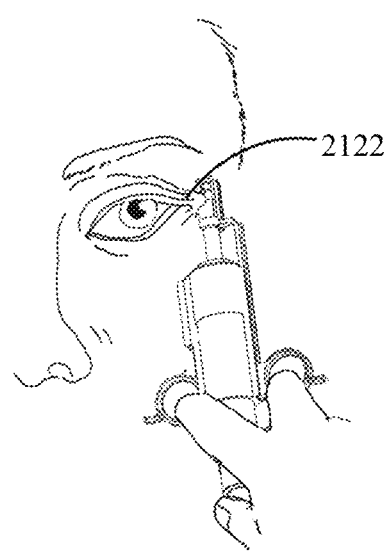

FIG. 21B depicts an illustration 2110 showing the fully assembled hook restraining adaptor and injector being used for the hydroporation of crow's feet wrinkle lines. The assembly is positioned with the cushioned hook restraint 2112 gripping the side of the face to administer a horizontal delivery 2114 of a HA cocktail. As the depth resolution of the hook restraint is insufficient to differentiate an intradermal depth and subcutaneous depth, the hook restraint is used only for orthogonal or horizontal injections where depth resolution is not important.

Referring to FIG. 20C, the perspective view 2040 depicts a fully assembled injector 2046 with the pincher restraint 2042 having the pincher 2048 at one end and a step-edge aid 2044. The pincher 2048 uses multiple gripping adhesive surfaces arranged in a 3-dimensional manner to improve gripping or pinching on one side. The step-edge aid 2044, also with adhesive surfaces, is attached over the ampoule and pinches the skin on the opposing side of the pincher 2048. Different versions of the step edge aid provide a different step edge depth to correspond to different depth injection. With a cross-sectional step-edge skin surface presented to the ampoule orifice, the injection is delivered horizontally into the skin rather than orthogonally. Unlike the hook restraint 2022, the two opposing edges of the pincher 2048 and the step-edge aid 2044 flexes the skin into a more precise step-edge for the ampoule orifice to deliver a jet stream into the shallower intradermal layer.

Figure 22A:
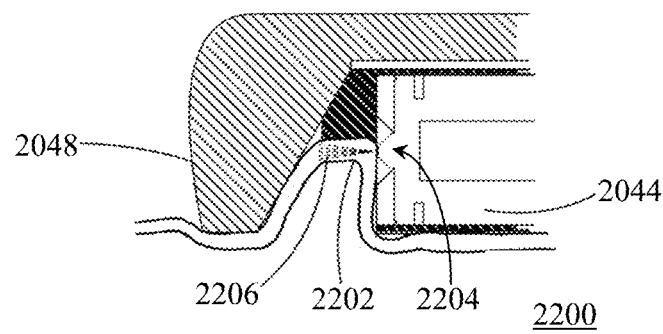
Figure 22B:
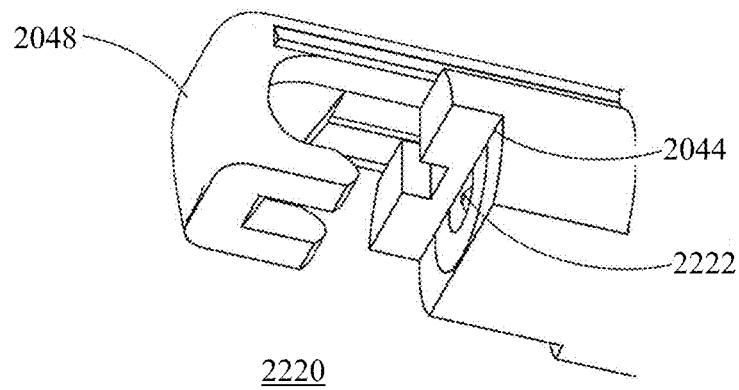
Figure 22C:
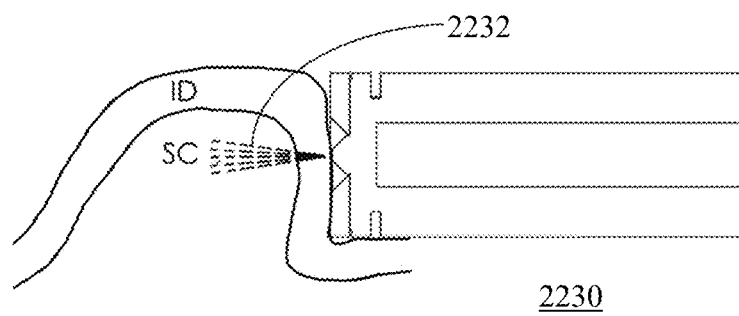
Figure 22D:
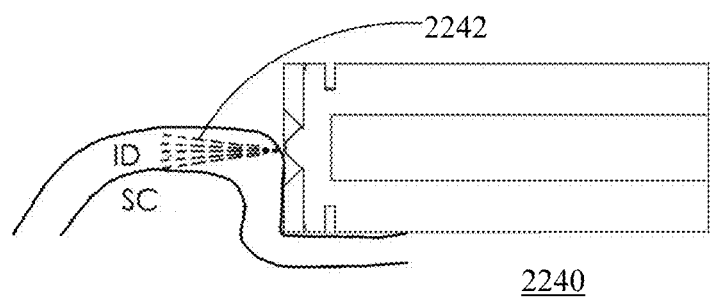

FIG. 22, comprising FIGS. 22A, 22B, 22C and 22D, depicts magnified views of the injector with the pincher 2048 and the step-edge aid 2044 during operation where FIG. 22A is a cross-sectional planar view of the pincher 2048 and the step-edge aid 2044 pinching the skin 2202 to present a vertical edge to the orifice 2204 for a jet stream injection 2206. FIG. 22B illustrates a bottom left front perspective view from below of the three-dimensional pinching surfaces is shown in the view 2200 showing the pincher 2048 and the ampoule orifice 2222 relative to the step edge aid 2044. FIGS. 22C and 22D illustrate adjusting the depth, using different depth step edge aids in planar views 2230, 2240 for subcutaneous tissue 2232 or intradermal tissue 2242 to allow the jet stream to be delivered accordingly.

An illustration 2120 (FIG. 21C) depicts an intradermal procedure being performed for crow's feet using the injector with the pincher 2048 and the step-edge aid 2044. The skin is pinched and the injection delivery is made horizontally 2122. The purpose of hydroporation is not to produce the signature wheals of intradermal vaccination delivery but for aesthetic beauty. As such, the skin pressure, propulsion pressure, skin depth and injectable volume are adjusted and programmed differently.

Figure 21D:
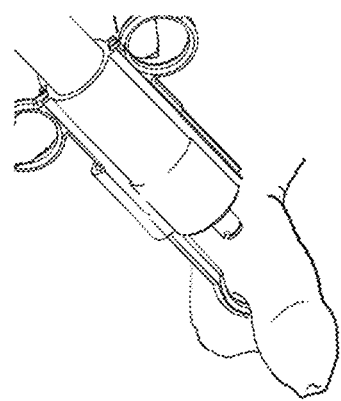

Nevertheless, the pincher restraint is also suitable for intradermal vaccination wheal-type delivery by adjusting the horizontal delivery depth to an even shallower intradermal layer and programming the injector to function differently. FIG. 21G is an illustration 2160 depicting a horizontal intradermal delivery 2162 targeted at Langerhans cells within the upper spinosum layer of the skin.

Referring back to FIG. 20D, an illustration 2060 shows a fully assembled injector 2064 with the long flat restraint 2062 with an ampoule 2066 with an extension tube attached 2068 to increase the reach of the ampoule. Other than a longer reach, the functionality of the ampoule, injector and the restraining adaptor remain the same.

The restraining adaptor can be of any shape or form or size, for instance the shape and size of a small cylindrical back paddle for Marionette line aesthetic treatment or a forked pincher to present a step-edged skin surface to the orifice so that the jet stream can be delivered to the skin at a horizontal angle or skew angle. Both intradermal and subcutaneous injections can be performed at the horizontal angle with a shallow horizontal depth used for intradermal injection and a deeper horizontal depth used for subcutaneous injection. The restraining adaptor can be sized to be large like a shepherd's crook to ensnare livestock or any shape to achieve a restraining effect. To be able to ensnare the target surface increases the success of an injection considerably in relative motion situations as the ensnaring action prevents relative motion.

U.S. Pat. No. 3,167,071 to Venditty describes a gripping adaptor for a needle free injector. Whereas the Venditty gripper is intended for two handed use with a manually triggered jet injector, the adaptor with injector assembly 2040 in accordance with the present embodiment can be used single handedly. The shape of the gripping surfaces is also different as Venditty's grip uses flat 2-dimensional opposing surfaces, while the present pinching restraint and step edge aid uses 3-dimensional pinching surfaces to simultaneously grip and press the skin against the orifice tip for superior step-edge effect. Also, Venditty requires an overhead hand position to manipulate the grip, while the hand positions of the restraints as shown in the illustration 2120 allows for concave intra-cavity injections 2150 as well as convex surface injections 2160. For intra-cavity step edge injection, the long flat can also be substituted with a longer pincher with a step edge aid and an extension tube to extend the reach.

Conventional hydroporation procedures are usually a two-handed affair with the surgeon inserting a finger into the patient's mouth to stretch the skin away from the teeth and with the other hand holding a conventional needle free injector. The orifice tip of a needle free ampoule has to be exactly aligned with the Marionette line for optimal hydroporation. This is done with great difficulty in conventional procedures because of the simultaneous movement of pushing the injector into the skin while the finger in the mouth is pulling the skin towards the ampoule orifice. Too much pressure by the ampoule on the skin can cause hurt or bruising to the sensitive injection site. Too little pressure can cause leakage. Too much finger pressure usually means the injection site is randomly distorted by the unpracticed finger and may have shifted in position. A required biting action from the patient is needed as part of procedure and the surgeon may be accidentally bitten. It requires considerable patience, skill and practice to properly perform this procedure.

The Mörl-Chuang procedure uses the hydroporation adaptor with the pressure sensitive injector and ampoule inserted 2020 (FIG. 20B). With only one hand in a familiar syringe style handhold 2100 (FIG. 21A), the cushioned hook of the hydroporation adaptor 2102 is quickly anchored inside the mouth to provide a back-pressure support for an automatic injection. The injector is configured to provide optimal skin pressure triggering for the hydroporation procedure using a thumb push. The surgeon can focus on not losing sight of the Marionette line until the moment the orifice touches the skin and the injection is automatically administered a short moment later. A return spring assembly 2010 (FIG. 20A) allows the surgeon to adjust and control the placement of the orifice tip with ease.

The use of a mechanical skin pressure sensitive mechanism whereby the pressure spring is specially tuned only for the small dynamic range of intradermal (ID) tissue depth alone or subcutaneous (SC) tissue depth alone is advantageously provided in accordance with the present embodiment. This allows the total travel length of thirty millimeters (or higher) to be tuned to the slight variation of ID or SC depth injections only. By programming the housing in this manner to administer an injection at a slightly different depth using an orthogonal delivery method but within the same tissue group allows a cascaded fibroblast effect at the same injection position but at slightly different depths. This Mörl-Chuang procedure when used in conjunction with the present embodiments provides for such a cascaded fibroblast effect using simple settings on the injector. Instead of ID, SC and IM settings, a custom injection with SC1, SC2 and SC3 or ID1, ID2 and ID3 can be preprogrammed into the housing with a carefully selected propulsion spring and pressure sensing spring. Custom propulsion springs in single or multiple spring configurations can be factory ordered to suit the application.

The systems and methods in accordance with the present embodiment advantageously provide flexibility in part replacement, interchange and configuration to match the procedure. Arrangements can be made with the factory to make available password keys to the practitioner to make in-the-field adaptations to the injector. Using a laser sintering 3D printer, an injector housing can be made locally at a low cost to match the skin type of the patient and prescribed to the patient for home care. That such injectable, ampoules and injector can be password coded and key coded for only the patient's use has an added advantage to deter the patient from sharing his personalized injector or personalized injectable. Any unauthorized use by another is deterred by the password protection feature provided.

Achieving the fibroblast effect with the combination of injectable, injector, ampoule and/or adaptors is an advantageous result of the systems and methods in accordance with the present embodiment. Such a hydroporation kit can be configured for home use or professional use with different permutations of injectables, ampoules, injector, adaptors and accessories.

There are no conventional needle free injectors designed for in-field self-maintenance, adaptation or calibration. Also, there is no conventional needle free injector that can be field disassembled and assembled with nothing more than an ampoule as a tool. There is also no conventional jet injector that can be mechanical password protected to hinder unauthorized disassembly and assembly, or allow such jet injectors to be recycled with appropriate passwords.

Azar does not have a multiple vial interface; it accepts a single fluid capsule at one time and the fluid capsule has to be changed to administer a different injectable from a different fluid capsule each time. Unlike Azar and other conventional procedures, the Mörl-Chuang hydroporation procedure in accordance with the present embodiment allows a pre-mix cocktail of chemically compatible injectable to be administered simultaneously, thus reducing the number of injections needed. The viscosity of this cocktail can be predetermined and the appropriate pressure settings programmed in the housing with the appropriate propulsion spring and pressure spring. Having a different cocktail with a different viscosity only requires a second injector with a different mechanical pressure program. Alternatively, multiple mechanical pressure programs can be used together in the same injector. Azar uses a single heavy-weight electrically and pneumatically programmed injector nozzle to provide an infinite permutation of possibilities of which most permutations are not practical.

The present embodiment advantageously allows the process of cocktail mixing to be keyed to the programmed injector, for instance a cocktail with one part of injectable A and two parts of injectable B when mixed together is to be used with an injector with a SC1 setting, while a cocktail with one part of injectable C and two parts of injectable A is to be used with an injector with a SC2 setting.

Mörl-Chuang hydroporation procedure also uses the sequencing of more than one injectable to be delivered one after the other in the same injection, increasing the efficacy of the procedure many folds. This present embodiment is able to provide a multiple spring configuration with the combined effect of two or more spring constants, k1, k2, k3 and so on or simply take the larger of the spring configurations. An example of a sequenced injection is to use a filler followed by Hyaluronic Acid or a HA followed by a filler. The HA is loaded in the ampoule first and the filler is loaded last so that the injection sequence is in the reverse order, that is the injection will place the filler first to pad the deeper section of the skin and HA to make the upper section of the skin supple. The reverse sequence can also be applied for a different effect. If this injection is not done together, the treatment would be ineffective because the padding and the softening effect is at different positions because of skin movement. There is no conventional mechanical jet injector capable of different skin pressure settings or in-field propulsion spring configurations. There is also no conventional programmable jet injector that uses skin compression as a parameter for their programming.

Besides Marionette line treatment at an orthogonal angle, the Mörl-Chuang procedure allows for one-handed orthogonal, horizontal or skew angle injections using just the restraining adaptor or together with any of the hook, pincher or long flat restraints. The pincher with the step-edge aid allows for horizontal delivery of the injectable to the intradermal level 2242 (FIG. 22C) and/or the subcutaneous level 2232 (FIG. 22D). There is a general contradictory effect using needle free injection for aesthetic treatment. High kinetic energy is used for fibro blasting but using the injector vertically means that the same high kinetic energy leads to the injectable penetrating to deeper depths. If treatment is to be delivered to the superficial tissue layers using an orthogonal angle of the injection orifice to surface, high kinetic energy cannot be used as the jet steam will just pass through that tissue layer and the effect of fibro blasting is minimal at that layer. By applying the injection at a horizontal angle allows the injectable to traverse across the same tissue layer with high kinetic energy without the need to sacrifice shallow depth penetration. This also allows for more precise and broader horizontal area treatment of intradermal and subcutaneous tissue. Such precision would not be possible without the use of the pincher adaptor 2048 that allows for precise horizontal delivery provided in accordance with the present embodiment. A wide permutation of treatment methods and precision to cater for the natural variations in skin aging is made possible with these selections of restraints. These novel adaptors when used in conjunction with the present embodiments allow these novel aesthetic treatments to be carried out.

In accordance with the present embodiment, the ampoule, injectable and injector have the ability to be personalized to the patient or personalized to the practitioners or personalized to an organization. Any of the parts that make up the injector can be custom specified and kitted accordingly. The injector can be self-assembled with the appropriate password. Parts can be exchanged or customized for in-field applications. Passwords can be reset and new ones created. This provides systems and methods not available with conventional devices.

In addition, the practitioner is allowed to use separate injectors with a number of "frequently used favorite" programs to achieve the same end functionality of an all-purpose machine. That these PING programs are copyrightable and in some cases may be patentable provides economic value to the practitioner. In the aesthetic industry, where the art of the practitioner is usually kept secret and medical procedures are the keys to the art means that such art is not shared, not even with the manufacturer. Giving the practitioner the ability to write his own PING software and to configure his own pressure parameters and adaptor use tailored to his art, makes systems and methods of the present embodiment unique. By providing the medical practitioner a means to intimately correlate the medical procedure to computer hardware and software, albeit a mechanical one, allows the practitioner the ability to protect his "IP", where in normal circumstances, he has no IP protection. This ability makes the hypodermic injector systems and methods for use in accordance with the present embodiment unique.

"First-time-success" is a particularly advantageous feature of the systems and methods in accordance with the present embodiment. By preconfiguring the propulsion spring force, pre-programming the moment of injection and simplifying the maneuvering motion of the injection process, the skill set of the expert practitioner is transferred into a set of tools for a user to perform a first time success in an otherwise complicated procedure of needle free injection.

Hutt and Erectile Dysfunction Procedures

Figure 21E:
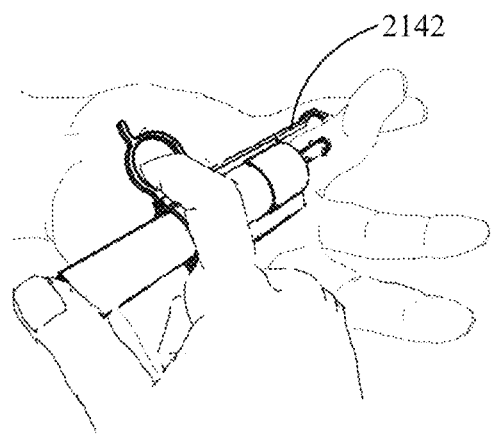
Figure 21F:
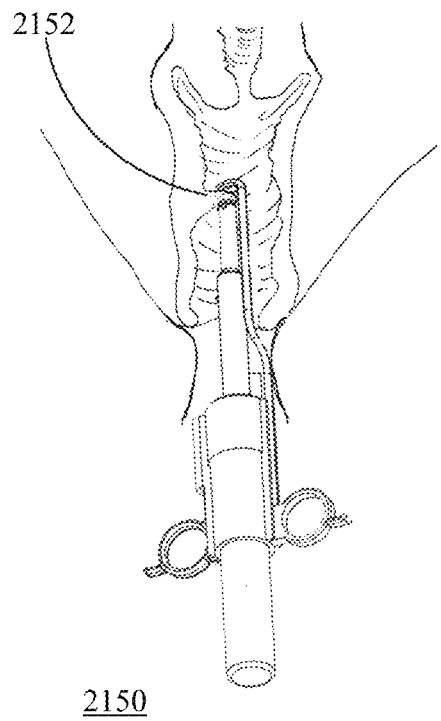
Figure 21G:
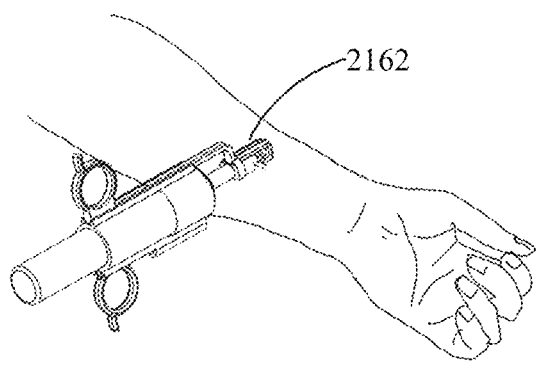

Referring to FIG. 21E, an illustration 2140 depicts the Hutt procedure in accordance with the present embodiment used for the treatment of Dupuytren's Contracture that affects the fingers. The hook restraining adaptor 2142 and needle free injector provide a less invasive and less painful treatment as compared to needle aponeurotomy or surgery. The restraining adaptor's hook is light and the highly maneuverable hand hold provides for a single-handed treatment and precise alignment of the ampoule orifice to the injection spot. FIG. 21D provides an illustration 2130 of another procedure where the restraining adaptor and injector provides for less invasive erectile dysfunction treatment of Peyronie's disease and other ED maladies in accordance with the present embodiment. An extension tube can be used to provide more personal space between the subject and the practitioner.

Intra-Cavity and In-Body Procedures

To extend the reach of the ampoule for an orthogonal injection, an extension tube 734 (FIG. 7) can be attached in between the ampoule and injector. This configuration can be used for orthogonal injection onto the cervix for instance or for other in-body injection procedures.

A long reach intra-cavity configuration is shown in 2060 (FIG. 20D) with a long flat restraint 2062 and an extension tube 2068. This provides the necessary reach for intravaginal 2150 (FIG. 21F) and intra-anal injections such as intra-anal injections for the treatment of Human Papillomavirus (HPV). The long flat restraint provides the grip 2152 to perform a horizontal injection along the virginal canal. Other intra-cavity procedures with narrow passageways can also be done with the ultra-slim versions of the ampoule. For extra-long reach applications where there is a possibility of bodily tissues interfering with the pressure sensing mechanism, the extension tube comes with a low kinetic friction sheath that reduces interference to the sides of the ampoule and extension tube. The same use of sprockets to float the plunger reduces friction considerably.

A rigid extension tube ensures that the pressure of the surface is similarly conveyed accurately and quickly to the injector for automatic injection at a predetermined cavity surface pressure. The various restraints can be properly sized to provide a back support if necessary, as well as to position the surface to be injected. When used in conjunction with a highly sensitive programmable pressure triggering mechanism and a reduced powered jet stream configuration, internal organs can also be injected while preventing harm to live organs. All this is done by manual operation without the use of electricity or pneumatics.

Conventional needle free jet injectors suffer from the lack of an ability to discriminate orifice to surface pressure whereas the injector in accordance with the present embodiment is designed to be triggered by surface pressure. Using a two Newton spring with a stroke length of thirty millimeters, the injector is able to discriminate an analogue change of 0.66 N per mm, or about 66-gram force per mm of pressure spring movement. The injector has a light and rigid body housing weighing approximately fifty grams in total without an ampoule. The restraining adaptor with the familiar dental syringe type hand-hold is designed for one-handed high maneuverability injection procedures. With programmable automatic triggering of the injector and configurable compression spring for application specific programming of the built-in FSMMC, a soft or light touch surface pressure and light injection propulsion pressure profile can be programmed and configured into the injector. To prevent the orifice from causing abrasion on fragile tissue, and to distribute a point pressure over a large area, a selection of soft seals can be used (see FIG. 4), including front seals shaped in medical silicone as well as medical silicone gel.

In summary, the restraining adaptor when used in conjunction with the present embodiment can be applied to any treatment or any procedure which requires a restraining pressure for needle free hypodermic injection. The restraining adaptor allows for a series of actions including but not limited to pulling, pushing, rotating, to snare, strapping, tying and pinching. The injector hardware and mechanical programs can be matched to the medical procedures and to the adaptors used. It is not necessary for the injector to be orthogonal to the skin as the restraining adaptor can apply an injection at any angle to the skin, including the rear surface of a body, as long as you can effect surface contact and provide a seal between the orifice and the surface.

Pedal Reloader

Figure 24A:
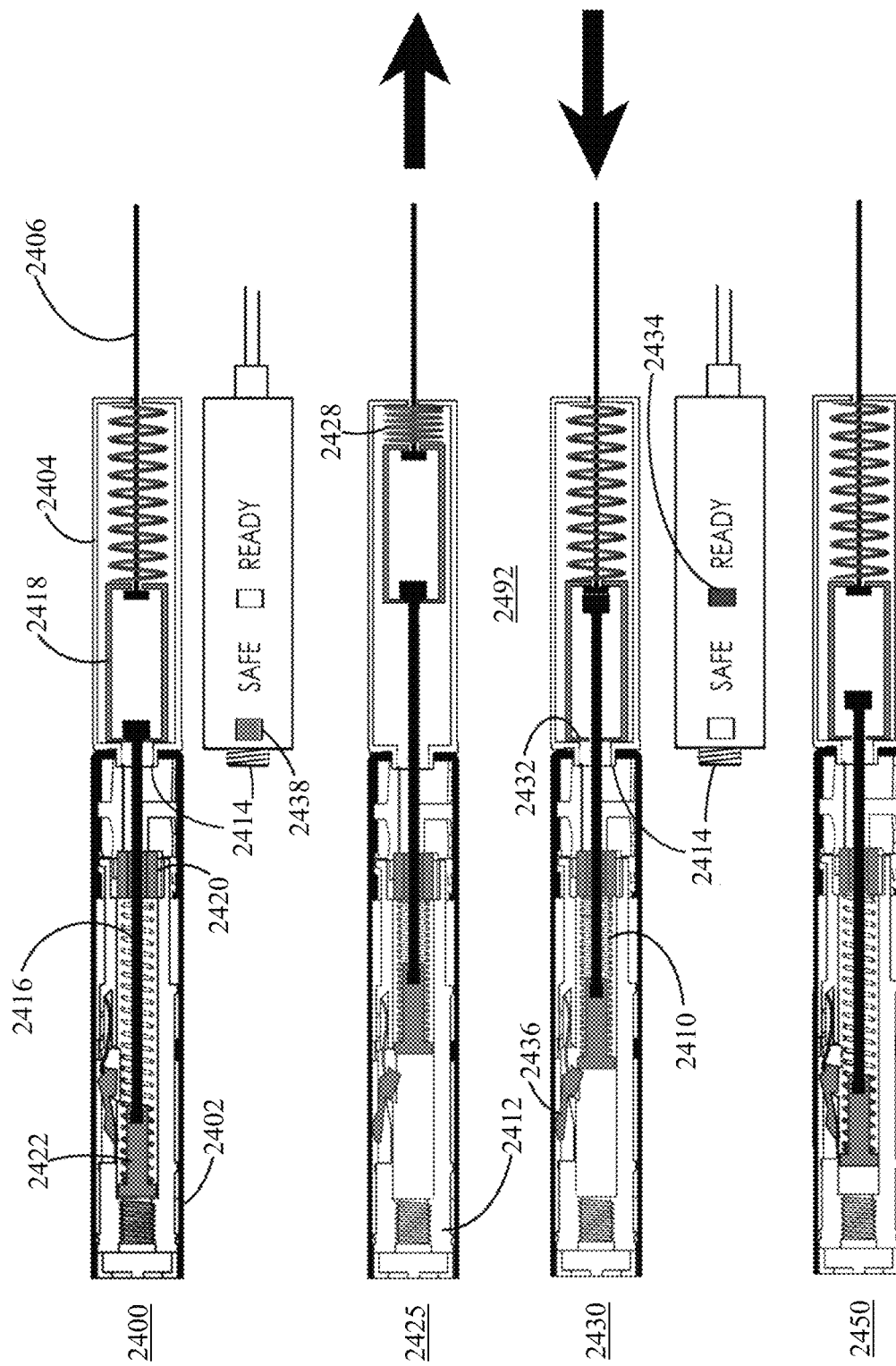
Figure 24B:
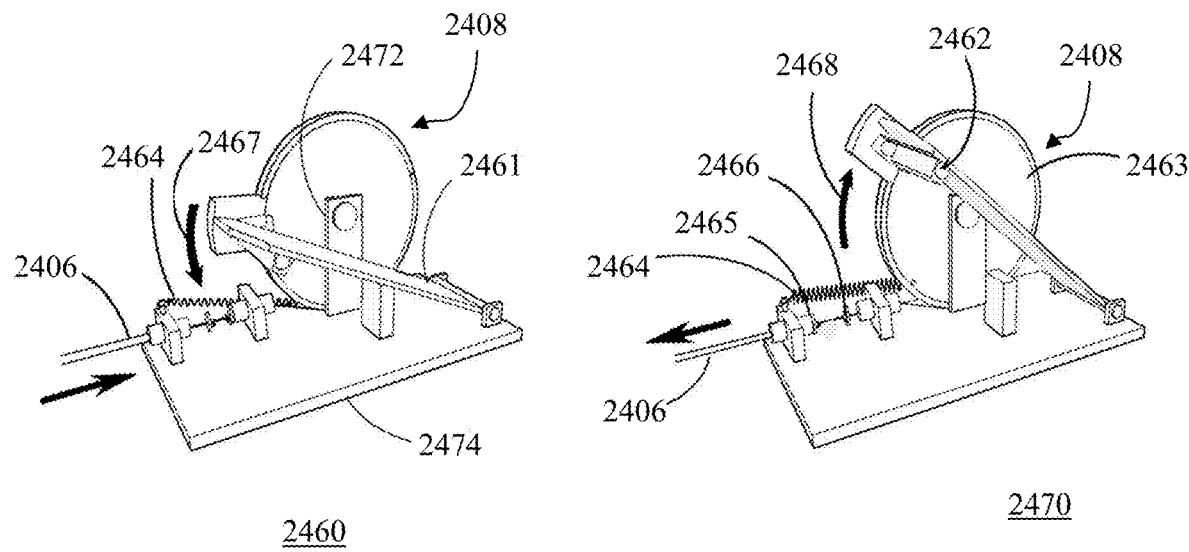
Figure 24C:
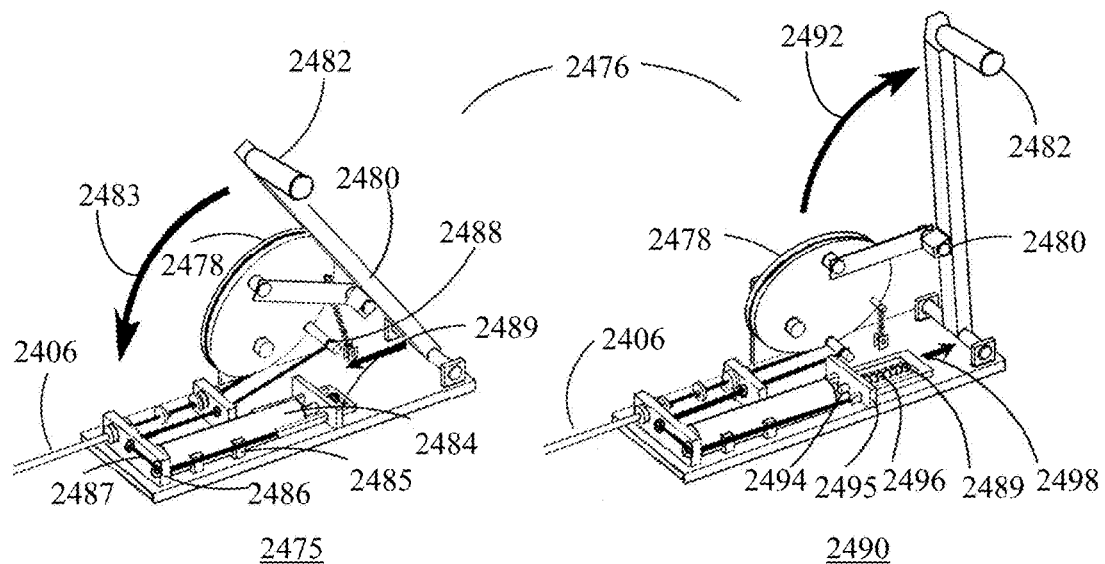

Referring to FIG. 24, comprising FIGS. 24A, 24B and 24C, depict views 2400, 2425, 2430, 2450, 2460, 2470, 2475, 2490 of a foot pedal reloader providing a quick in-situ rear reloading of the injector in accordance with the present embodiment. In-situ reloading using the foot frees the hands to replace fresh ampoules on-the-fly for quick injection turnaround. The planar view 2400 depicts the rear of a modified injector housing 2402 which is connected to a reset chamber 2404. A bicycle-brake style tensioning cable 2406 with a stripped-out sheath connects the reset chamber 2404 to a foot-operated pedal reloader 2408 depicted in the perspective views 2460, 2470. The cable sheath 2406 remains on the outside of the reset chamber 2404 in the same way as a bicycle-brake mechanism. Press and release the foot pedal once to compress the propulsion spring 2410 in the bolt carrier 2412 and the spent injector is ready for use.

A rear hollow screw connector 2414 connects the housing 2402 to the reset chamber 2404 using an optional hollow rear screw 762 (FIG. 7). A long reloading pin 2416 resides in a slide 2418. The long reloading pin 2416 is inserted through the rear hollow screw connector 2414, continues through a hollow end lug 2420 and continues through to connect to the bolt carrier rear reloading pad 2422 (rear reloading pad 740 (FIG. 7)) using a twist lock mechanism. The slide 2418 moves left and right along the reset chamber 2404, pulling and pushing the long reloading pin 2416 along its path.

The reloading cycle begins when the tensioning cable 2406, which is connected to the slide 2418, is pulled; the slide 2418 in turn pulls the long reloading pin 2416 until the slide 2418 fully compresses the reset chamber spring 2428 and is unable to go further. The long reloading pin 2416 would have by now pulled the rear reloading pad 2422 along with it and cocks the propulsion spring 2410. The tension cable 2406 is now relaxed with the release of the foot pedal 2461 (FIG. 24B). At this time, the slide 2418 is pushed towards the injector side 2432 of the reset chamber 2404 by the relaxation movement. This in turn allows the reloading pin 2416 to come to rest at the READY 2434 eyelet position which provides a visual cue that the injector is now ready for the next injection. The reloading cycle is now complete; with the propulsion spring 2410 compressed and latched 2436. When the injection is triggered and the latch released, the long reloading pin 2416 advances forward together with bolt carrier pad 2422 and the long reloading pin 2416 comes to rest at the SAFE position eyelet 2438. The whole cycle is repeated for the next reloading.

The foot pedal reloader 2408 is used to pull the tensioning cable 2406 connected to the reset chamber 2404. Referring to FIG. 24B, the foot pedal 2461 is connected by a pedal lever 2462 to a reduction wheel 2463. The reduction wheel 2463 is connected to a pedal retraction spring 2464 to return the pedal to its normal state when the pedal 2461 is not depressed. An adjustable tension release stopper 2465 and an adjustable full tension stopper 2466 regulate the travel distance of the tensioning cable 2406 to provide a good connection to the reset chamber.

When the pedal 2461 is depressed 2467, the pedal lever 2462 causes the reduction wheel 2463 to rotate and pull the tensioning cable 2406 and the pedal retraction spring 2464. When the pedal is released 2468, the pedal retraction spring 2464 causes the pedal 2461 to return to its original position. A support 2472 is provided to hold the reduction wheel 2461 to a base plate 2474 to which the other parts are connected as shown.

Throttle Reloader

FIG. 24C also shows an alternative embodiment using a throttle reloader 2476 for desktop use. The throttle reloader 2476 is connected to the reset chamber 2404 in the same way as the foot pedal reloader 2408 by using a tensioning cable 2406. The reset chamber 2404 mounted on the rear of the injector operates the same way with both the pedal reloader 2408 and the throttle reloader 2476. Moving the throttle forward and backward once, completes one reloading cycle.

However, the throttle reloader 2476 uses a constant pressure elliptical cam 2478 to replace the reduction wheel 2463. A lever 2480 connected to a throttle handle 2482 provides a fulcrum leverage to reduce the effort in pushing or pulling the throttle handle 2482. This provides a more comfortable and safer feel when the forward tensioning motion is used to reload the compression spring. In the event one loses grip on the throttle handle 2482, there is no recoil to cause any injury to the hand. A recoil would not be a problem for the foot using the pedal reloader 2408. In addition to the visual eyelets on the reset chamber 2404 to indicate READY 2434 or SAFE 2438 states as before, the position of the throttle handle 2482 also provides motion and position cues as to the state of the throttle reloader 2476.

The throttle reloader 2476 can also be used for front reloading of a normal injector. The exhausted injector in the safe position is placed in the reloader 2484. The injector is held in place by the struts 2485 and the rear support 2486. Another tensioning wire 2487 is used to connect to the elliptical cam 2488 at one end and to the ramrod assembly 2489 at the other end. When the throttle handle 2482 is pushed 2483, the tensioning wire 2487 is pulled and the ramrod assembly 2489 is pulled into the injector to cock the propulsion spring. When the throttle handle 2482 is withdrawn 2492, the ramrod 2494 held together by grommets in the assembly plate 2495 is retracted out of the injector by the retraction spring 2496. The whole ramrod assembly 2489 including the ramrod 2494 is retracted in the direction shown 2498. The injector can now be removed for use.

Both these novel reloading methods are designed for in-situ rear reloading. They can be adapted for use with any needle free compression spring injection system with rear access for the reset chamber.

Airlock Adaptor—External Parts

Figure 28:
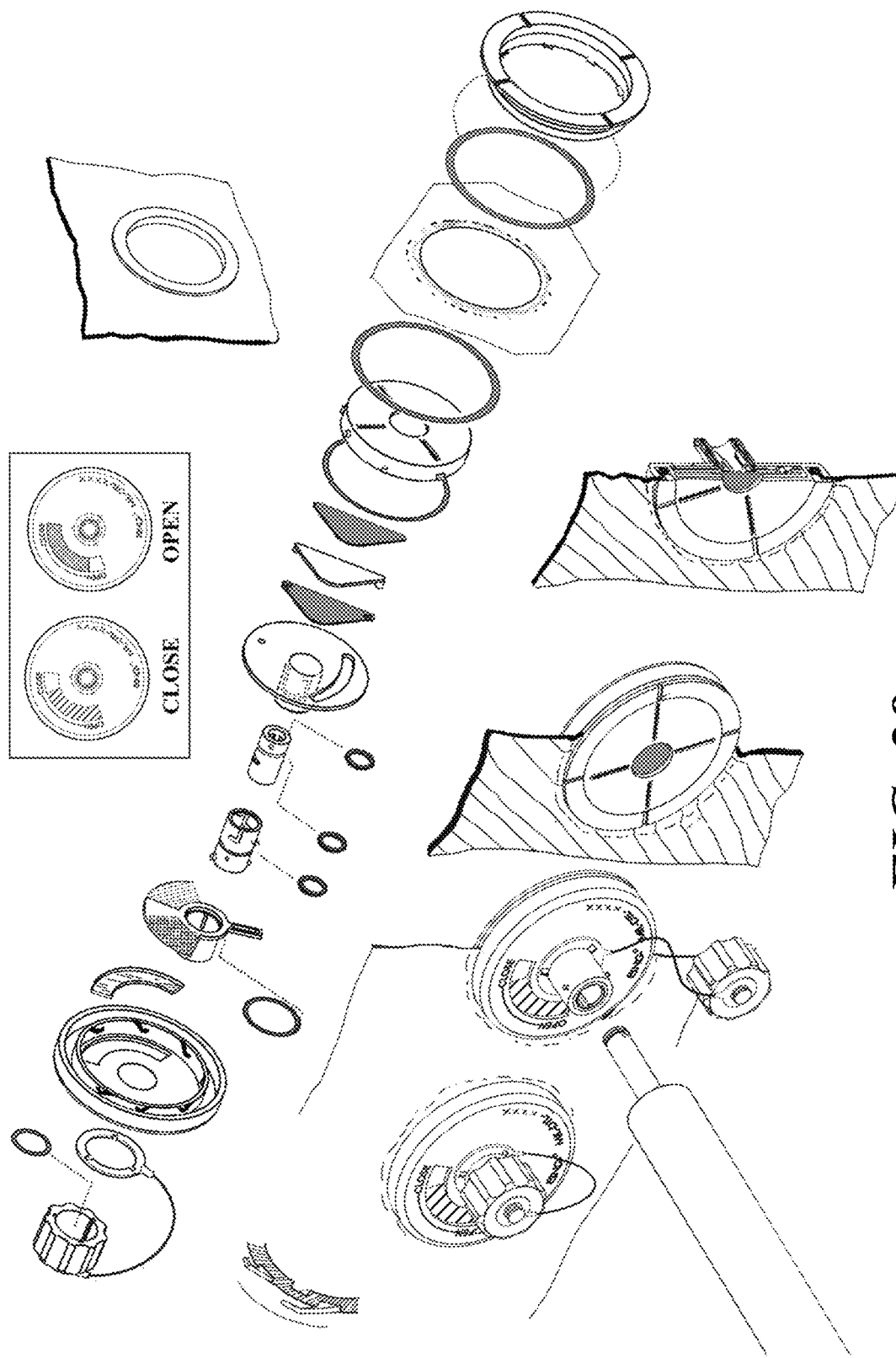
FIG. 28 is an exploded parts perspective view (without reference numerals) of an airlock adaptor for use with the needle-free injector system in accordance with the present embodiment.
Figure 29A:
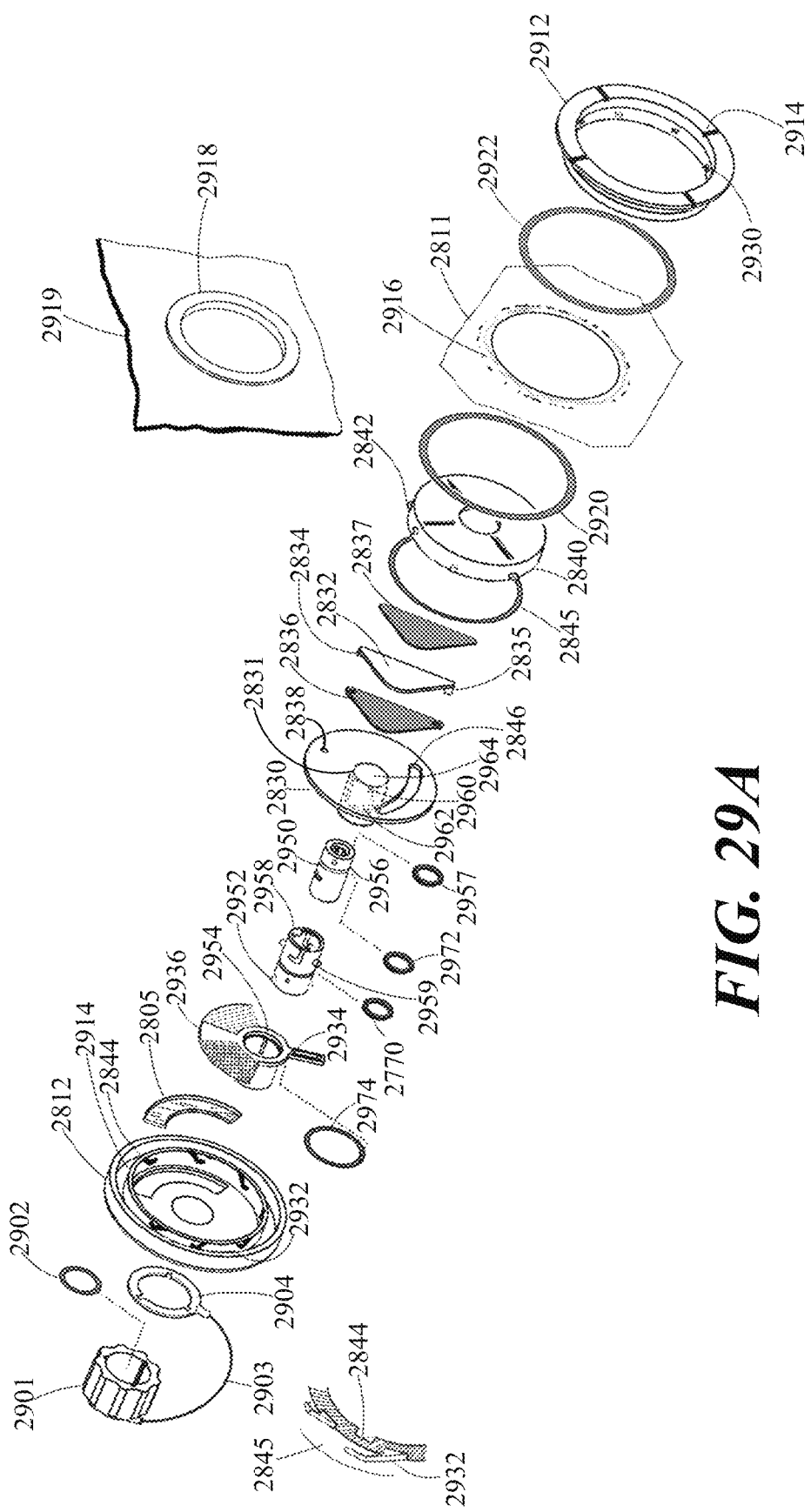

FIG. 28 shows the embodiment of the airlock adaptor and the exploded parts view without reference numerals. Referring to FIG. 29, comprising FIGS. 29A, 29B and 29C, the airlock adaptor is depicted with reference numerals, wherein FIG. 29A depicts a perspective view and an exploded parts view of the adaptor, FIG. 29B depicts perspective and planar views of the outside of the airlock adaptor and FIG. 29C depicts perspective views of the inside of the airlock adaptor.

Figure 29B:
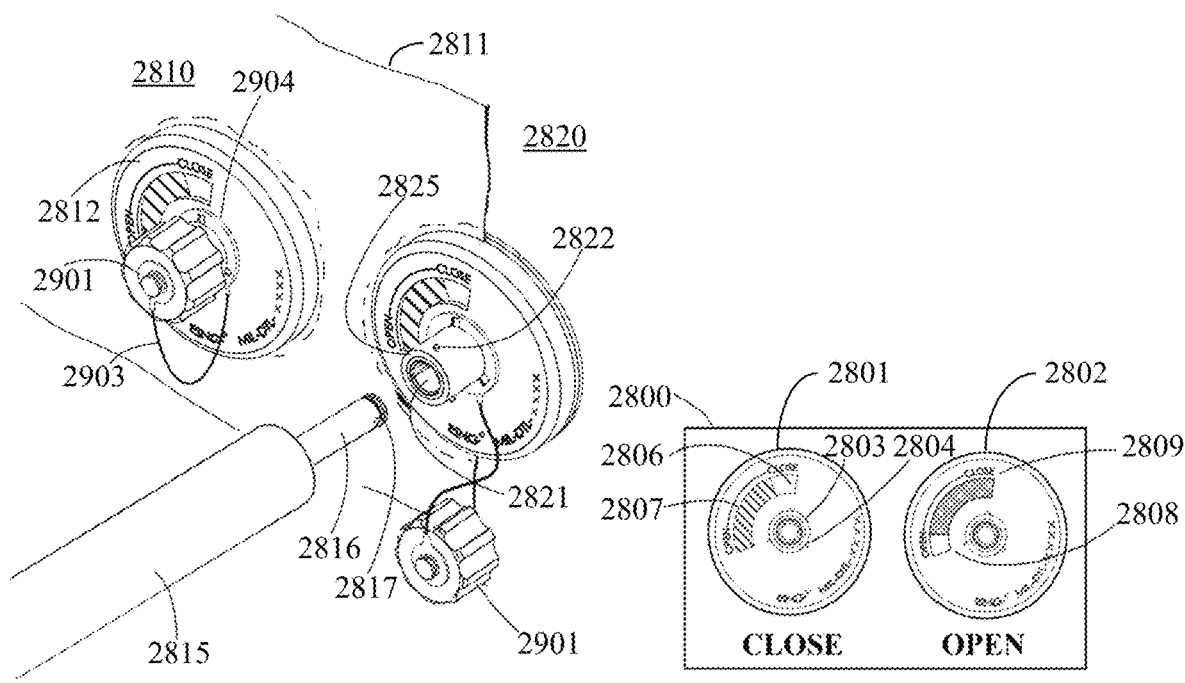
Figure 29C:
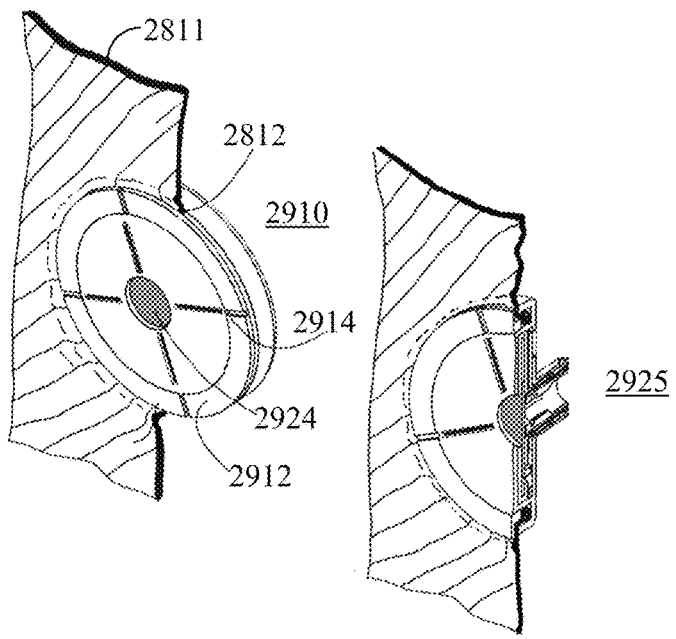

Referring to FIG. 29B, a boxed area 2800 shows a planar view of a front face 2801 of an open airlock adaptor with the cover off and a planar view of a front face 2802 of a closed airlock adaptor with the cover off. At the center of the face 2801 is a hollow protruding tube 2803 sized for an ampoule to be inserted into. The outer surface of the tube 2803 has three sprockets 2804 for a cover 2901 (FIG. 29A). On the face 2801, 2802 is a transparent viewing window 2805 which indicates whether the airlock portal is at the default close position 2806 with a green visual cue 2807 or open 2808 with a red visual cue 2809. The airlock adaptor can be made of any hard material, the seals made of any pliable material and the window made of any transparent material.

A front perspective view 2810 shows the airlock adaptor attached to a cutout illustration of a non-porous material 2811 such as a Nuclear, Biological and Chemical (NBC) hazmat suit or a space suit. When the cover 2901 is on, an O-ring 2902 on the inside of the cover 2901 ensures an effective air and water tight seal against the outer casing 2812 of the adaptor. The cover 2901 is secured to the airlock adaptor via a metal lanyard 2903 and a lanyard ring 2904. The lanyard ring 2904 is pressed fitted into the housing.

When used in conjunction with the injector 2815 with an attached ampoule 2816, the airlock adaptor provides a means to prevent unintended medium from traversing through the non-porous material while allowing the ampoule to move through the airlock device to provide an injection on the other side. A perspective view 2820 shows the airlock adaptor with the military-type cover 2901 taken off to expose a hollow center 2821 into which the ampoule 2816 tip with sprocket 2817 is inserted. The sprockets 2822 are used to secure the cover 2901 to the adaptor. The view 2820 shows concentric cylindrical tubes 2825 whose functions will be described later.

Referring to FIG. 29C, a perspective view 2910 depicts the airlock adaptor viewed from the opposite side of the non-porous material. Note that the outer housing 2812 of the airlock adaptor goes over the non-porous material 2811, sandwiching the material with a 4-slotted restraining clamp 2912. The restraining clamp 2912 is a bayonet-type male mount formed to lock into numerous J-angled female grooves 2914 inside the casing 2812 of the adaptor. An internal support ring 2916 can be stitched threaded or heat sealed inside a more fragile material to prevent the ripping of fragile Positive Pressure Personnel Suit (PPPS) material or a metal grommet 2918 can be crimped over a thicker non-porous material 2919 for sandwiching. Together with the inner washer O-ring seal 2920 and outer washer O-ring seal 2922, an air tight and water tight seal is maintained between the outside and the inside of the non-porous material. A special 4-slotted tool (not shown) uses the four slots 2914 for tightening the restraining clamp to the housing, with the inner washer, non-porous material and outer washer in-between them. The view 2910 shows the airlock in a closed position 2924. A view 2925 shows a cross-sectional cutout of the same adaptor with the parts fully assembled.

Airlock Adaptor—Internal Parts

The two most important internal parts of the airlock adaptor are the portal disc 2830 and the delta gate 2832. The portal disc 2830 has a hole 2831 in the middle for the ampoule to pass through and the delta gate 2832 opens or closes this hole 2831. The delta gate 2832 is always closed except when the ampoule is ready to pass through to perform an injection. There are two sprockets 2834, 2835 on the delta gate 2832 at the two acute vertices of the delta. A front surface seal 2836 and a rear surface seal 2837 are glued onto the delta gate 2832 by adhesives. The delta gate 2832 fits into a portal disc swivel hole 2838 using the sprockets 2834, 2835. and is held in place by a portal disc rear support 2840 held together by inserting the sprockets 2842 into the J-grooves 2844 on the housing 2812 and sealed with a washer seal 2845. Another set of sprockets 2930 on the 4-slotted restraining clamp 2912 secures the clamp against a different set of J-grooves 2932. Each set of sprockets and J-grooves are held in place by the back pressure of the pliable seals and O-ring and, if really necessary, screws, welding and adhesives can be applied to secure the adaptor further.

Figure 31:
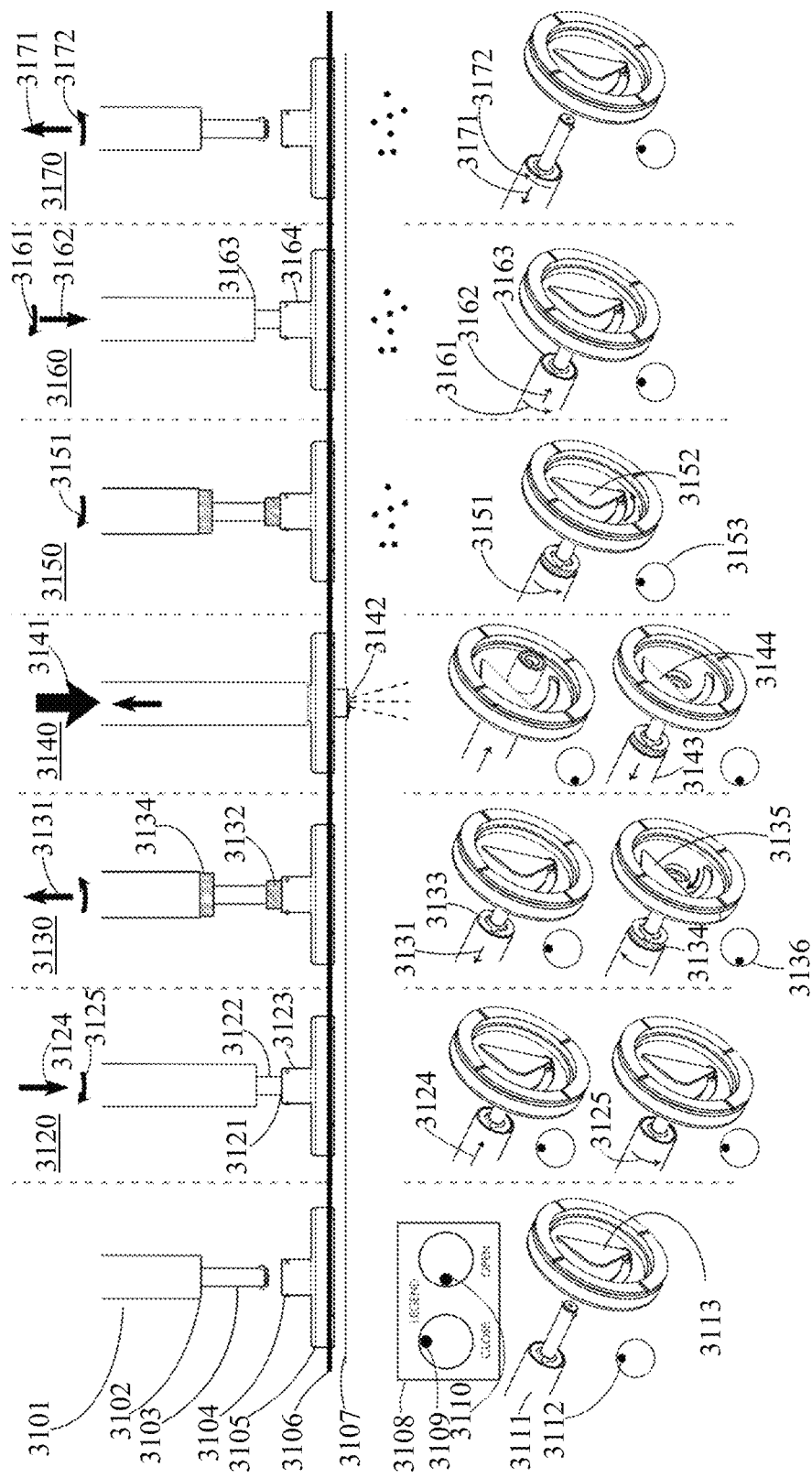
FIG. 31 is the multiple planar and corresponding perspective views of FIG. 30 showing the injector and the airlock adaptor during operation in accordance with the present embodiment with reference numerals.

In FIG. 31 described hereinbelow, the sprocket 2834 swivel the delta gate open 3135 or shut 3152. The other sprocket 2835 on the delta gate 2832 is longer and passes through a swivel slot 2846 on the portal disc 2830 to continue to pass through a slotted arm 2934 of an indicator outer tube 2936. So, as the delta gate 2832 opens or closes, the slotted arm 2934 of the indicator outer tube 2936 twists by the same amount to indicate on the front face whether the hole 2831 is closed 2806 or open 2808.

The next three parts are tubes that make up the hardware to carry out the FSM logic using sprockets and grooves. The three tubes are an inner tube 2950, a middle tube 2952 and an outer tube 2954. Sprockets are extruded and grooves are cut into the various internal and external surfaces of these three tubes to synchronize the various safety interlocks and sequenced order of the airlock adaptor. The function of the inner tube 2950, which has a groove on the inner surface, is to guide the insertion of the ampoule 2816 till it reaches the end 2956 of the tube. Here two ampoule sprockets 2817 twist and lock against the inner tube O-ring 2957 to form an air and water tight seal. When the ampoule sprocket is locked 2817, the locking pushes another sprocket 2958 on the middle tube 2952 causing the middle tube to turn into an arming channel 2960 on the portal disc 2830, while simultaneously holding fast the ampoule sprocket 2817. The arming channel 2960 on the portal disc 2830 only allows the inner and middle tube to slide in and out together, sliding out until they reach the armed position 2962 (see also 3132 in FIG. 31). The pathway 2962 now allows the sprockets to traverse across the tube to open the delta gate 2832 by a twisting action and enter into an ampoule throughway channel 2964. In this manner, the ampoule 2816, along with the inner ring 2950 and the middle ring 2952, can pass through the portal disc 2830 with the delta gate 2832 opened and administer the injection. After injection, travel along the various pathways are reversed to close the delta gate, return the middle ring from armed to safe, and end with the ampoule being removed from the airlock adaptor. The next section describes this in greater detail.

The remaining parts of the airlock adaptor are O-rings 2970, 2972 and a washer seal 2974 at various locations of the inner, middle and outer tube surfaces to seal the airlock adaptor to prevent unintended medium from traversing across the non-porous material.

Functional Operation of the Airlock Adaptor

Figure 30:
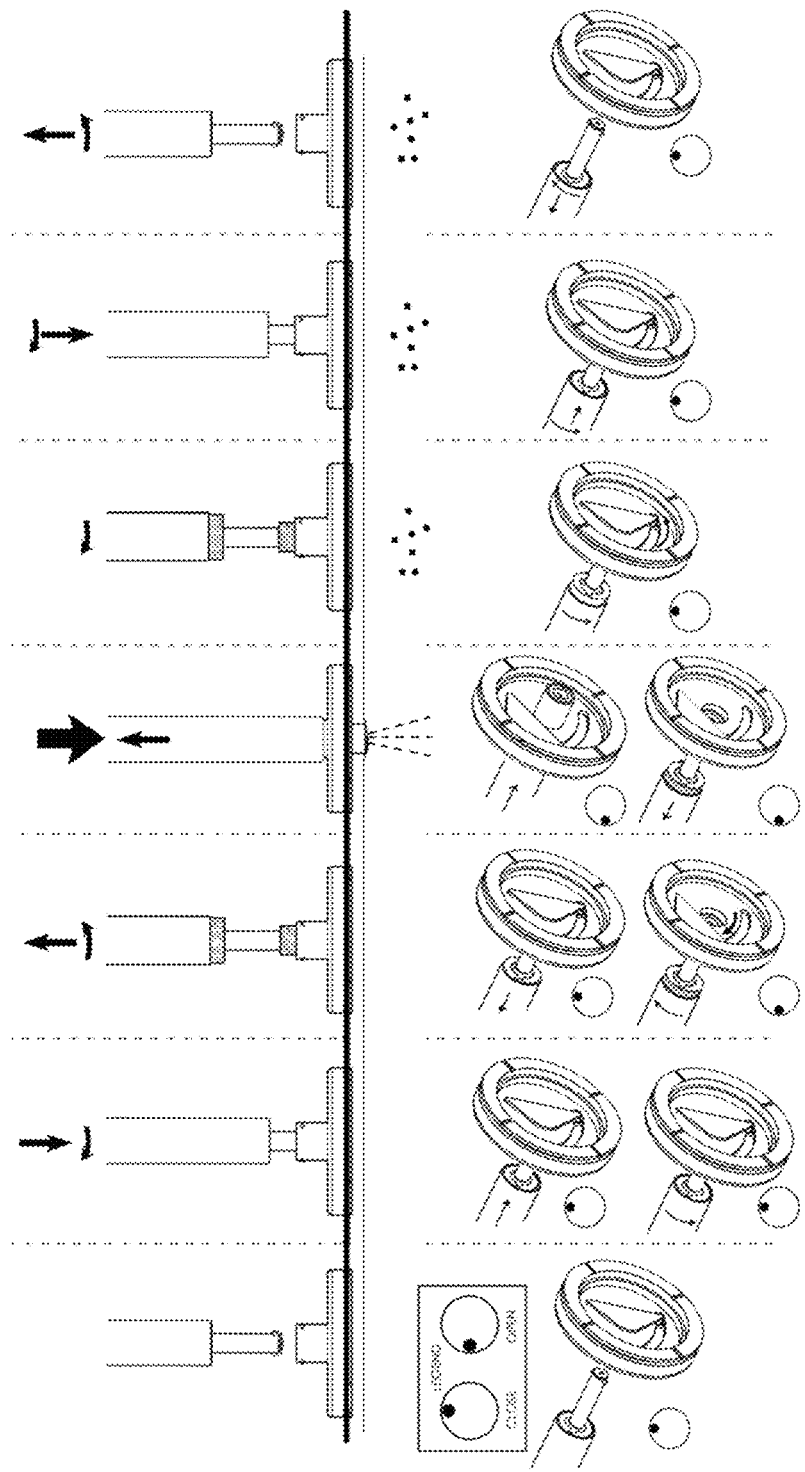
FIG. 30 is multiple planar and corresponding perspective views of the injector and the airlock adaptor during operation in accordance with the present embodiment showing the injector and airlock safety interlocks and handshaking protocol (without reference numerals).

FIG. 30 shows the functional operation of the airlock adaptor without reference numerals and FIG. 31 shows the functional operation of the airlock adaptor with reference numerals. Referring to FIG. 31, seven side-by-side side planar and corresponding perspective views form an illustration 3100 of the interactive operation of the airlock adaptor with the needle-free injector in accordance with the present embodiment. At the start, an injector 3101 is in a safe position 3102 and the ampoule 3103 is pre-filled and ready for use. The cover is removed from the airlock adaptor and the tip 3104 of the airlock is flush with the airlock housing 3105. This symbolizes that the airlock is in a SAFE position and the airlock portal is locked and cannot be opened even if you try to twist the inner tube with the ampoule or another object. The airlock adaptor is attached to the non-porous material 3106 and on the other side of the non-porous material is the surface to be injected 3107. The box 3108 illustrates the two position of the airlock portal, a 12 o'clock position for close 3109 and a 9 o'clock position for open 3110. The default rear perspective view 3111 of the injector, ampoule and airlock adaptor is shown with the visual cue closed 3112, and the portal in the default safe and closed green position 3113.

Moving onto the next column 3120. To begin the injection, the injector housing is held and aligned the ampoule sprocket to the chamfered grooves in the adaptor 3121. The ampoule 3122 is inserted fully into the hollow recess of the airlock adaptor 3123 with a push motion 3124. This is followed with a twist clockwise motion 3125 to lock the ampoule sprockets with the inner tube of the airlock. If the ampoule is not fully inserted, it is not possible to twist clockwise to lock. Just like the FSMMC and PING on the injector, the airlock adaptor is also grooved and sprocketed to allow or restrict certain motions so as to move the airlock from one state to another using similar FSM logic in hardware. With the injector in the safe position, it is not possible to misfire the injector with this motion. The airlock is also restricted in an anti-clockwise motion. The ampoule tip is now locked and sealed with the O-ring in the inner tube. Both the injector and the airlock remain in their respective safe positions.

Moving onto the next column 3130, the injector 3131 is pulled and the inner tube and middle tube of the airlock adaptor are retracted until they stop. This motion arms the airlock adaptor and the airlock adaptor 3132 is no longer flush. A red ring visual cue 3132 can now be seen to indicate that the airlock adaptor is now armed. The injector is still in the safe position at this point of time as the injector visual cue 3133 is not showing. By relaxing the pull motion, the injector is armed in the usual manner by twisting the injector anti-clockwise. At the end of the rotation, the red visual cue on the housing will rotate to portal open position. At this moment, two things have happened simultaneously, a) the injector has armed itself 3134, and b) the airlock portal has opened 3135. That is to say, the injector will auto arm itself when it opens the airlock portal. Also at this time, there are three red visual cues showing: red on the injector 3134, red on the airlock tube 3132, and red on the airlock portal on the housing 3136. The injection is ready to be administered.

Moving onto the next column 3140, the injector housing is pushed into the airlock adaptor using the full stroke length of the injector 3141. The ampoule, locked to the airlock tubes, will slide through the airlock and deliver the orifice tip to the skin surface 3142. At a frictionally compensated surface pressure, the injection will be automatically administered in the usual manner. Appropriately positioned O-rings and washer seals between the various tubes will prevent any leakage between the two sides of the non-porous material. At the end of the injection, the injector is fully withdrawn out of the adaptor at the return stroke 3143, returning to the position at the beginning of the injection. At this time, the airlock portal is still open 3144.

Move onto the next column 3150. At the end of the return stroke and with the injector fully withdrawn, a clockwise twist is performed to close the airlock 3151. The airlock portal will close 3152 and the housing indicator will indicate green and closed 3153.

Moving onto the next column 3160, the clockwise twisting motion is continued from before 3161 and the injector is pushed into the airlock adaptor 3162. Two things will happen simultaneously: a) the injector will go into a safe position 3163 and b) the airlock will return to a safe position 3164. At this moment, the airlock will remain closed. Once the airlock is no longer in the armed position, twisting the injector will not open the airlock because the twisting motion is now restrained by the grooves.

Moving onto the last column 3170, the injector is pulled 3171 together with an anticlockwise motion 3172 and the injector and ampoule are removed from the airlock adaptor. The airlock cover is then returned to the airlock adaptor and the injection process is finished.

FSMMC, PING and the Airlock Adaptor

The three tubes on the airlock adaptor and the portal disc are interlocked together with sprockets and grooves to provide transition pathways similar to the use of sprockets and grooves on the injector housing using the FSMMC and PING. The grooves and sprockets on the airlock adaptor are more complicated because of the multiple dimensional use of pathways, where the state of the airlock is passed from one tube to another. To reiterate the point, in FIG. 29A, when the ampoule sprocket 2817 is locked into the inner tube 2956, control is passed to the middle tube sprocket 2958 which moves both the inner tube and the middle tube together using sprocket 2959 from the safe position 2960 to the armed position 2962 airlock pathway on the portal disc. When the middle tube arrives at the armed position 2962, control is passed onto the outer tube 2936 which rotates the delta gate 2832 using the rotating arm 2934 to open the delta gate to allow the ampoule to pass through.

Reversing the sequence retracts the ampoule from the skin surface, closes the airlock portal, sets the airlock back to safe and unlocks the injector from the adaptor with ease. Using PING on both the injector and the airlock adaptor, safety interlocks between the injector and the airlock adaptor are programmed into the injector to synchronize and control the airlock adaptor. For instance, the injector is set to auto safe if it is not already in the safe position. This is done during the insertion of the ampoule into the airlock by the clockwise twist motion to insert the injector into the airlock's inner tube. This means that the injection cannot be accidentally administered if the airlock is not open. Insufficient pressure on the skin also prevents an injection and this is inherently provided by the injector.

During the pull and anti-clockwise twist motion of opening the airlock, the injector simultaneously enters into the armed position or auto arm. When the injector housing is now pressed into the skin, all the interlocks and pathways are aligned on both the injector and the airlock to provide a pass-through pathway from orifice to surface. The FSM not only allows the injector to set its own safety interlocks but also allows the injector to control the safety interlocks on an external device while simultaneously synchronizing the interlocks between both devices. This handshaking communication also means that it is not possible to remove the injector if the airlock is still open.

Nuclear Nanoparticles, Biological and Chemical Contaminants

In accordance with the present embodiment and in situations where the unintended medium is NBC suit related, that is nuclear, biological or chemical agitators, a pre-treatment agent can be coated on the front seal to pre-treat the surface of the airlock prior to the opening of the airlock portal. It can be appreciated that these NBC agitating agents are too small and beyond the ability of O-rings and sealing technology. This pre-treatment agent can be in a gel that both pre-treats and captures contaminants at the same time. The recessed opening in the inner tube can also be configured for decontamination and uses the forward surface of the ampoule as the activation action for such pre-treatment.

A properly-sized pressure activated gel seal 422 (FIG. 4) will dispense a gel to sterilize the entrance of the airlock adaptor when the ampoule is inserted and locked into the airlock. This gel can be designed to neutralize and entrap any nanoparticles and/or viruses, or chemical agents present within the insertion hollow cavity during the process of the injection, and to continue to protect the airlock after the ampoule is withdrawn. An alternative embodiment is that the airlock adaptor's inner tube "O-ring" seal can be replaced with a pressure activated seal which can also be adapted for the same purpose.

The use of the airlock adaptor extends beyond portal interfaces for protective wear. The adaptor can be placed on any surface which can accommodate the airlock adaptor such as a hermetically sealed chamber, hyperbaric chamber or a hypobaric chamber.

Alternate Embodiments

It should be appreciated that any person suitably skilled in the art of pressure sealing and suitably informed by this description can modify and adapt the method, position and type of O-rings, washer seals or any type of pressure sealing methodology without changing the purpose of the use of the airlock. It should also be appreciated that any person skilled in the art of FSMMC, PING or sequenced logic and suitably informed by this description can also program or reprogram the airlock hardware to switch the sprockets and groove positions amongst the concentric tubes to perform the same function and ordered sequence as described or emulate the sequence without using FSMMC or PING. It should also be appreciated that any person skilled in the art of FSMMC, PING or sequenced logic can also change the push/pull and twist left/right motion, permutation and sequenced order without changing the purpose of the airlock adaptor.

It should also be appreciated that the airlock adaptor is not limited to the use of inhibiting air, or limited to the use with the injector or ampoule described herein. The airlock adaptor can function equally well with any suitable modified jet injector or needle syringes. It should also be appreciated that the airlock adaptor is not limited to the use of conveying an ampoule through the airlock. Any material or object can be conveyed through the airlock portal when opened. Such conveyable material conveyed can be oxygen, waste gases, human waste, water, food, medical or non-medical objects or materials, electrical devices or fiber communication devices.

Likewise, any device with a sequenced order can be used to interface and interact with the safety interlocking sequence of arming the airlock adaptor prior to opening the airlock and such arming and airlock opening need not be limited to the various push/pull or twist left/right motion sequences.

The number of safety interlocks can be increased or reduced without changing the purpose of this airlock adaptor. Although the present embodiment allows both the injector and the airlock adaptor to perform their own safety interlocks while simultaneously synchronizing the safety interlocks of each other, this is not a strict requirement for alternative embodiments. The safety interlocks acting together in concert so that the arming process of the both the injector and airlock adaptor is done at the same time is preferred but any other form of interlocking can be used without changing the purpose of the present embodiments.

Airlock Adaptor Flow Chart

Figure 32:
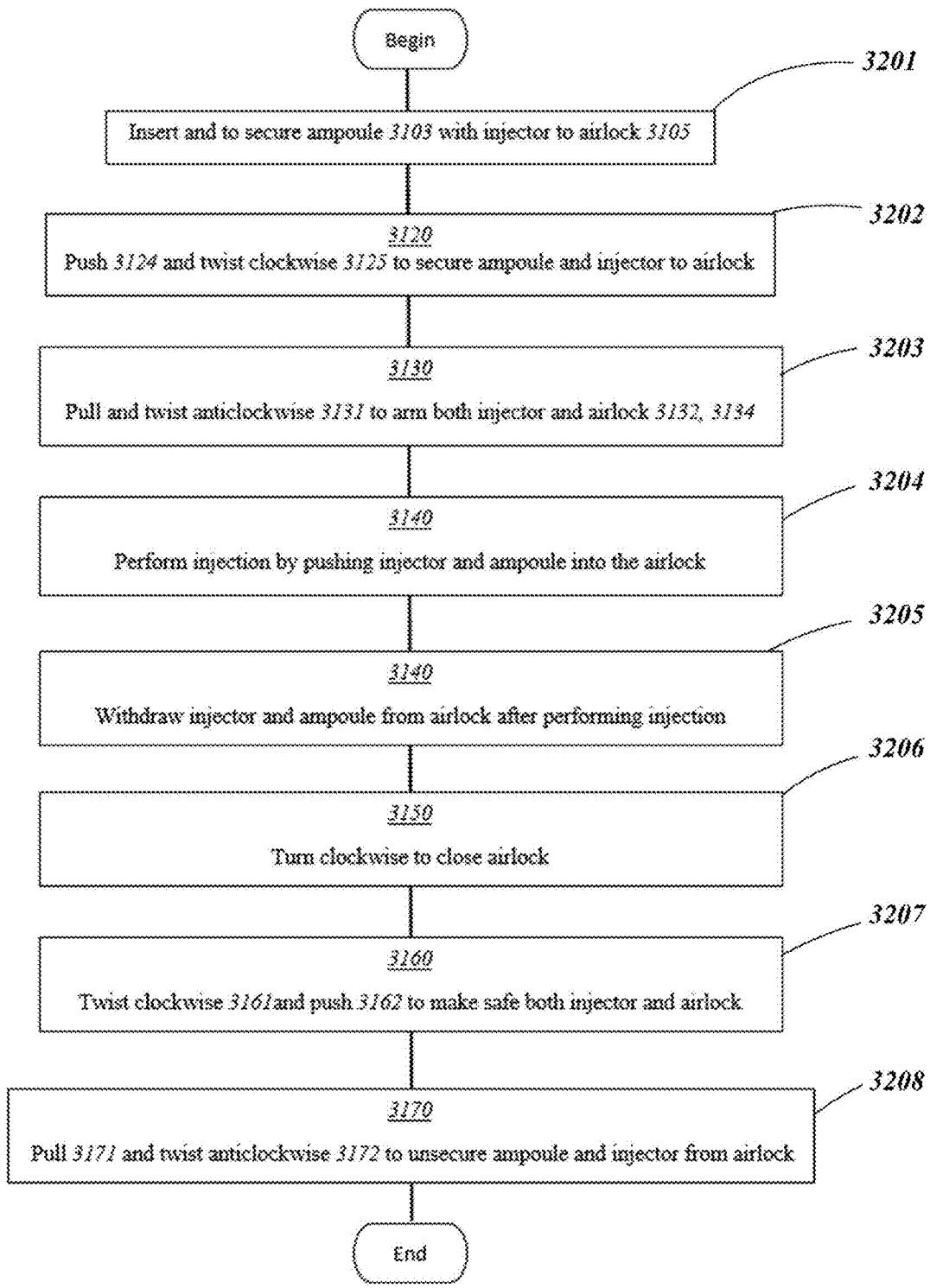
FIG. 32 is a flowchart depicting the functional operation of the injector with the airlock adaptor in accordance with the present embodiment.

Referring to FIG. 32, a flowchart 3200 depicts the functional operation of the injector with the airlock adaptor. The functional operation begins with inserting 3201 the ampoule with injector into the airlock. This is done by a push and twist clockwise motion to secure 3202 the ampoule and injector to the airlock. Next, a pull and twist anticlockwise motion arms 3203 both the injector and the airlock. Thereafter, the injection is performed by pushing 3204 the injector and the ampoule into the airlock 3204. Next, the injector and ampoule are withdrawn 3205 from airlock after performing the injection. Turning the airlock clockwise closes the airlock 3206, after which a twist clockwise and push 3207 make both the injector and airlock safe. Finally, a pull and twist anticlockwise motion unsecures 3208 the ampoule and injector from the airlock to end the injection cycle.

Alternative Airlock Embodiments

Figure 33A:
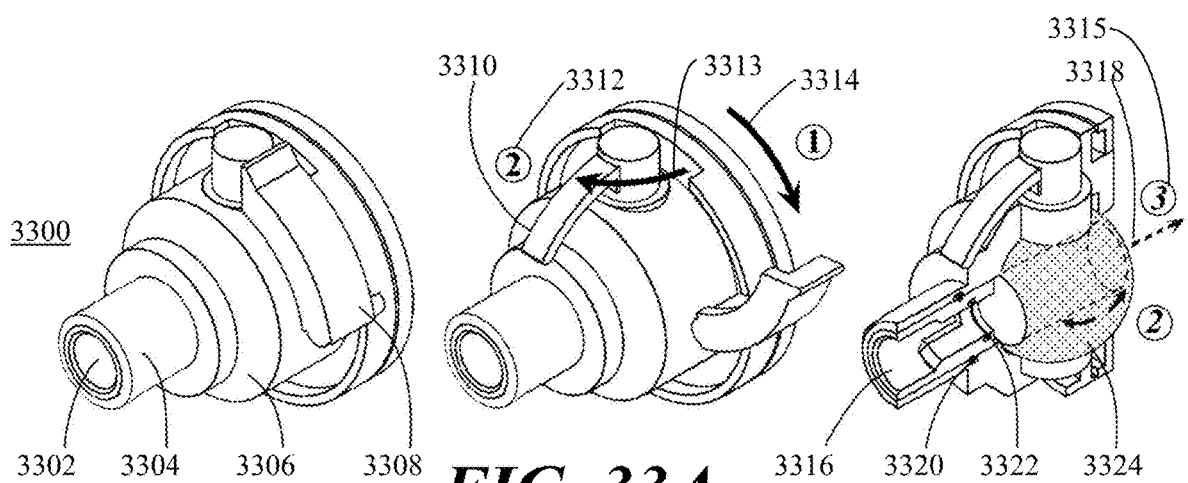
Figure 33B:
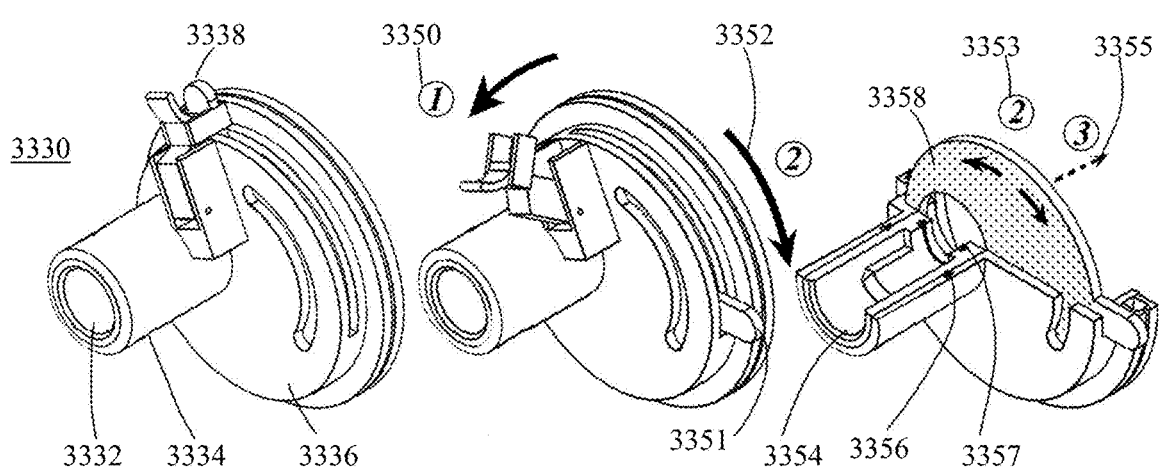
Figure 33C:
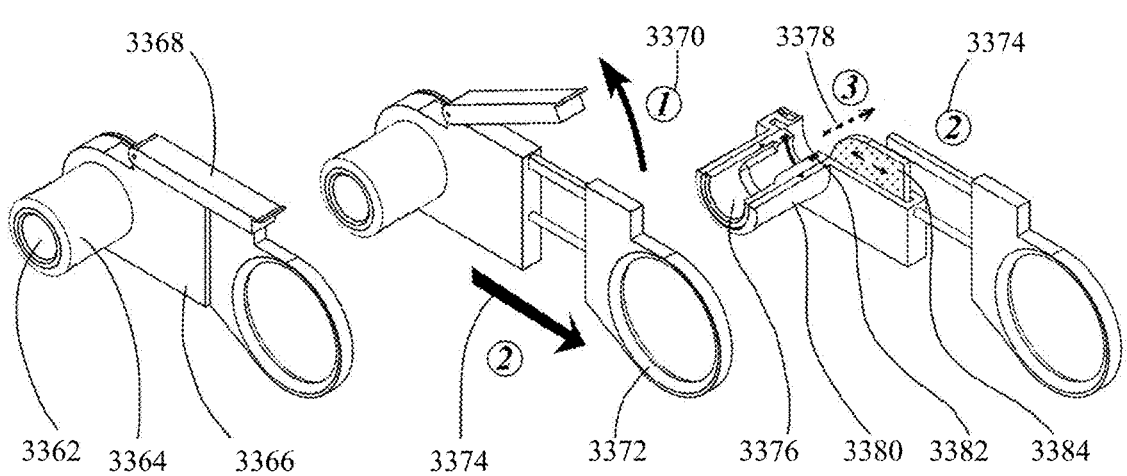

FIG. 33, comprising FIGS. 33A, 33B and 33C, depicts alternative airlock adaptors which use a simple three-motion action after inserting and securing the ampoule into the airlock in accordance with the present embodiment. These simple airlock adaptors require manual safety interlocking sequences, do not have FSMMC and the user needs to be mindful about synchronous use. Three types of alternative airlock adaptors include, but are not limited to, a ball valve airlock adaptor 3300, a rotating gate airlock adaptor 3330 and a sliding gate airlock adaptor 3360. The shape, size and form of the safety and valve mechanisms can vary as long as the purpose of the safety and valve mechanisms remains the same. The purpose of the safety mechanism is to provide a safety interlock so that the airlock valve is not accidentally opened. The purpose of the airlock valve is to provide access to an ampoule and/or injector for a needle or needle-free injection through the airlock valve opening. All three designs have O-rings and sealant coating on the valves for an air and water tight seal.

The ball valve airlock adaptor 3300 includes an inner tube 3302 for insertion and securing of the ampoule, an outer tube 3304 attached to a housing 3306, and a safety lever 3308 covering another rotating lever 3310 that opens the ball valve 3324. The first motion is to arm the airlock 3314 by moving the safety lever 3308 away to expose the rotating lever 3310. The second motion is to open the airlock 3312, 3313 by rotating the ball valve 3324. The third motion 3315 is to perform the injection by sliding the inner tube and ampoule 3316 through the valve opening 3318. The sequence is reversed to withdraw the inner ring and ampoule, close the airlock, return to safety and remove the ampoule and injector. An O-ring 3320 between the inner ring and the outer ring provides a seal during sliding. The O-ring 3322 provides a seal when the ampoule is inserted and secured in the hollow inner ring, and the ball valve 3324 is sealant coated and greased for additional sealing capabilities.

The rotating gate 3330 and the sliding gate 3360 operate in the same manner—both having an inner tube 3332, 3362, an outer tube 3334, 3364, a housing 3336, 3366, and a safety 3338, 3368 covering an airlock opening lever 3351, 3372. A first motion 3350, 3370, a second motion 3352, 3374 and a third motion 3355, 3378 are sequentially required to move from safe to arm, to move from arm to open airlock, and to move to inject correspondingly. The sequence is reversed after injection. O-rings 3356, 3357, 3380, 382 and gate sealant 3358, 3384 facilitate maintaining of airlock integrity (e.g., an air-tight and/or water-tight seal).

Figure 34:
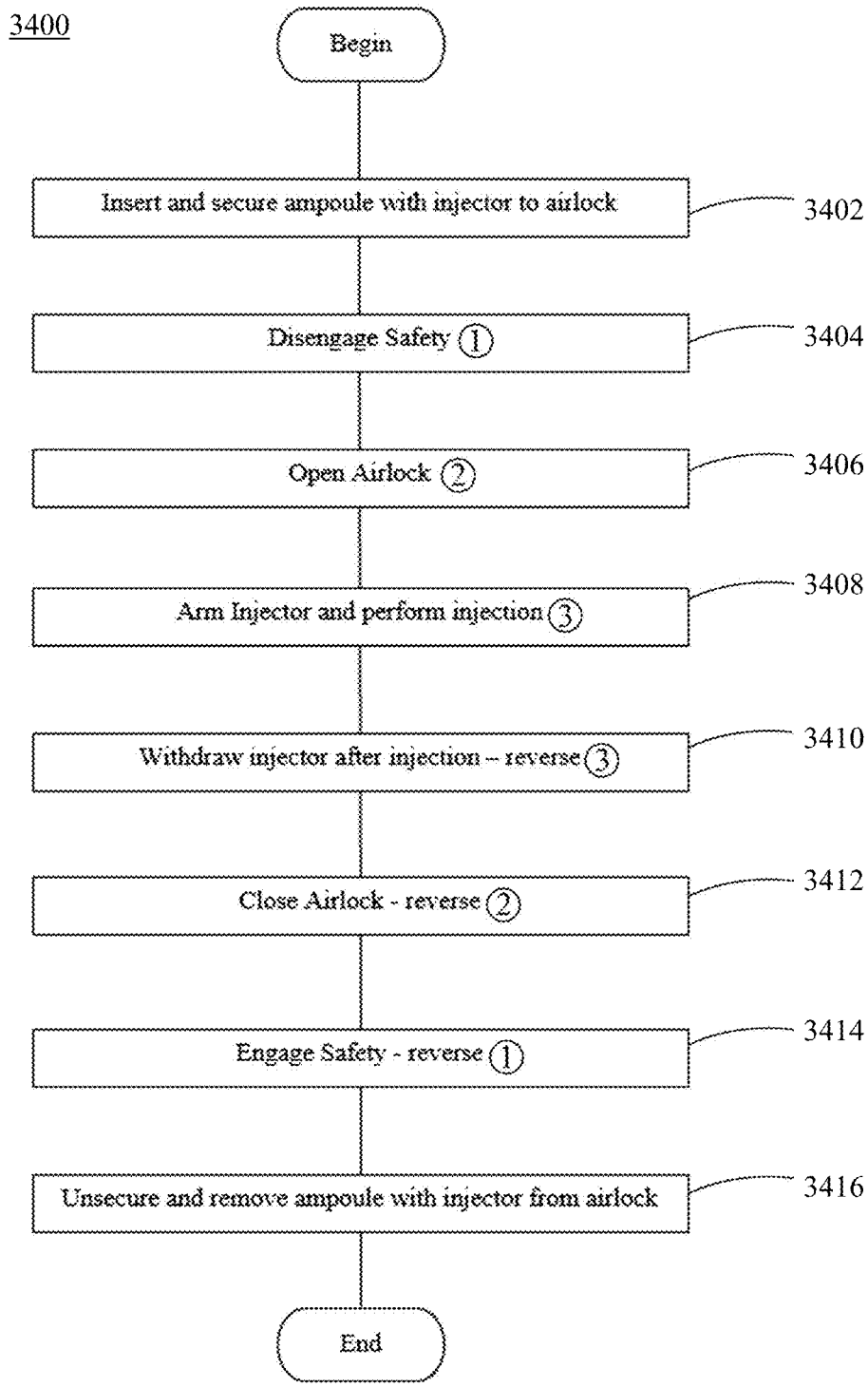
FIG. 34 is a flowchart for functional operation of alternative adaptors (e.g., the alternative adaptors of FIG. 33) in accordance with the present embodiment.

Referring to FIG. 34, a flowchart 3400 depicts functional operation of alternative airlock adaptors (e.g., the alternative adaptors of FIG. 33) in accordance with the present embodiment. The flowchart 3400 begins with insertion and securing 3402 of the ampoule with injector to the airlock. Then, the safety is disengaged 3404 with a first motion and the airlock is opened with second motion 3406. Next, the injector is armed and an injection is performed 3408 with a third motion. This is followed by withdrawal of the injector after the injection by reversing the third motion 3410. Then, the airlock is closed by reversing the second motion 3412 and the safety is engaged by reversing the first motion 3414. Finally, the ampoule with injector is secured and removed from the airlock to complete the process 3416.

The Needle-Free Injector System and its Accessories

Figure 25:
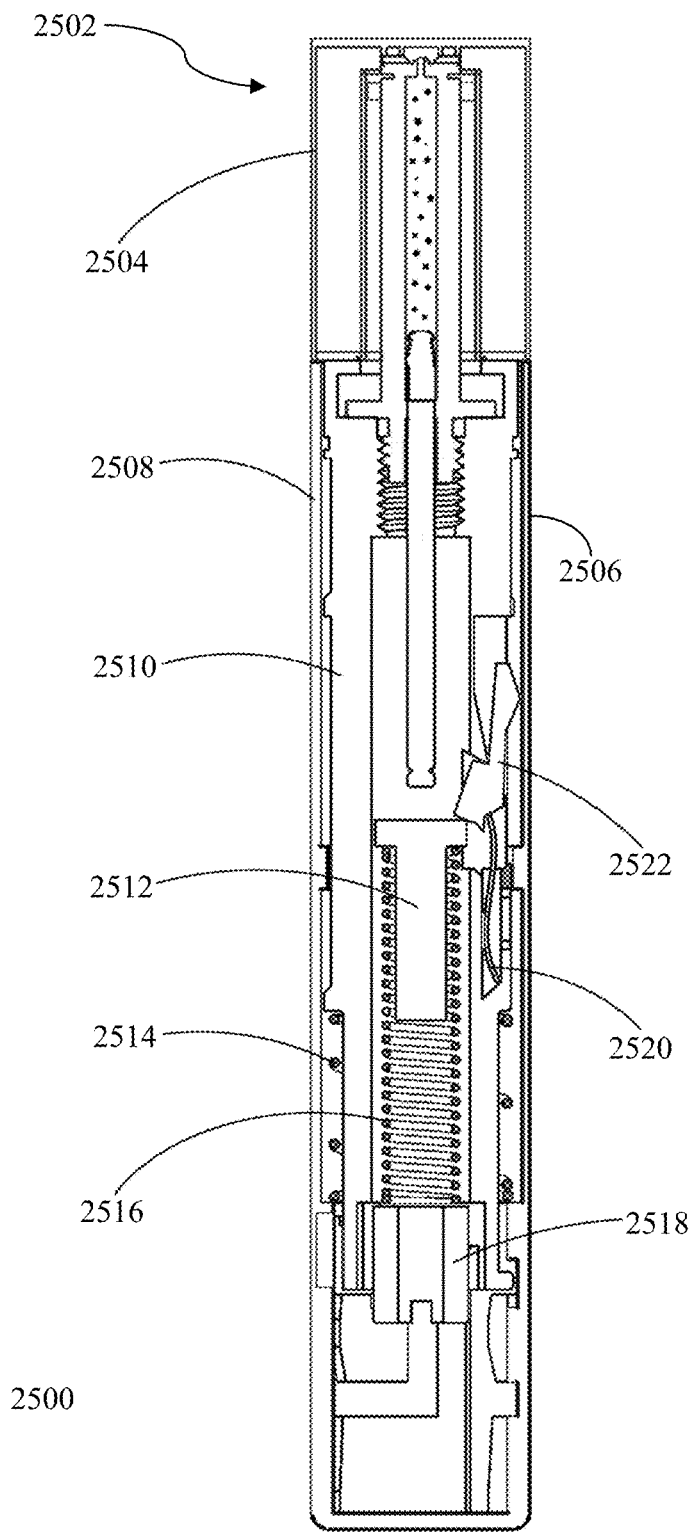
FIG. 25 is a side planar view of the ampoule module and injector in accordance with the present embodiment.

Referring to FIG. 25, a side planar cross-sectional view 2500 depicts the needle-free injector system 2502 in accordance with the present embodiment. The system 2502 includes an ampoule module 2504 and a pressure sensitive injector 2506. The ampoule module 2504 is attached to the injector enclosed by an injector housing 2508. The housing 2508 contains a bolt carrier 2510. The bolt carrier carries a pad 2512, a pressure sensitive spring 2514, a propulsion spring 2516, a hollow end lug 2518, a leaf spring 2520 and a latch 2522. A total of eight parts make up the injector and the ampoule module 2502 makes up the ninth.

Figure 35A:
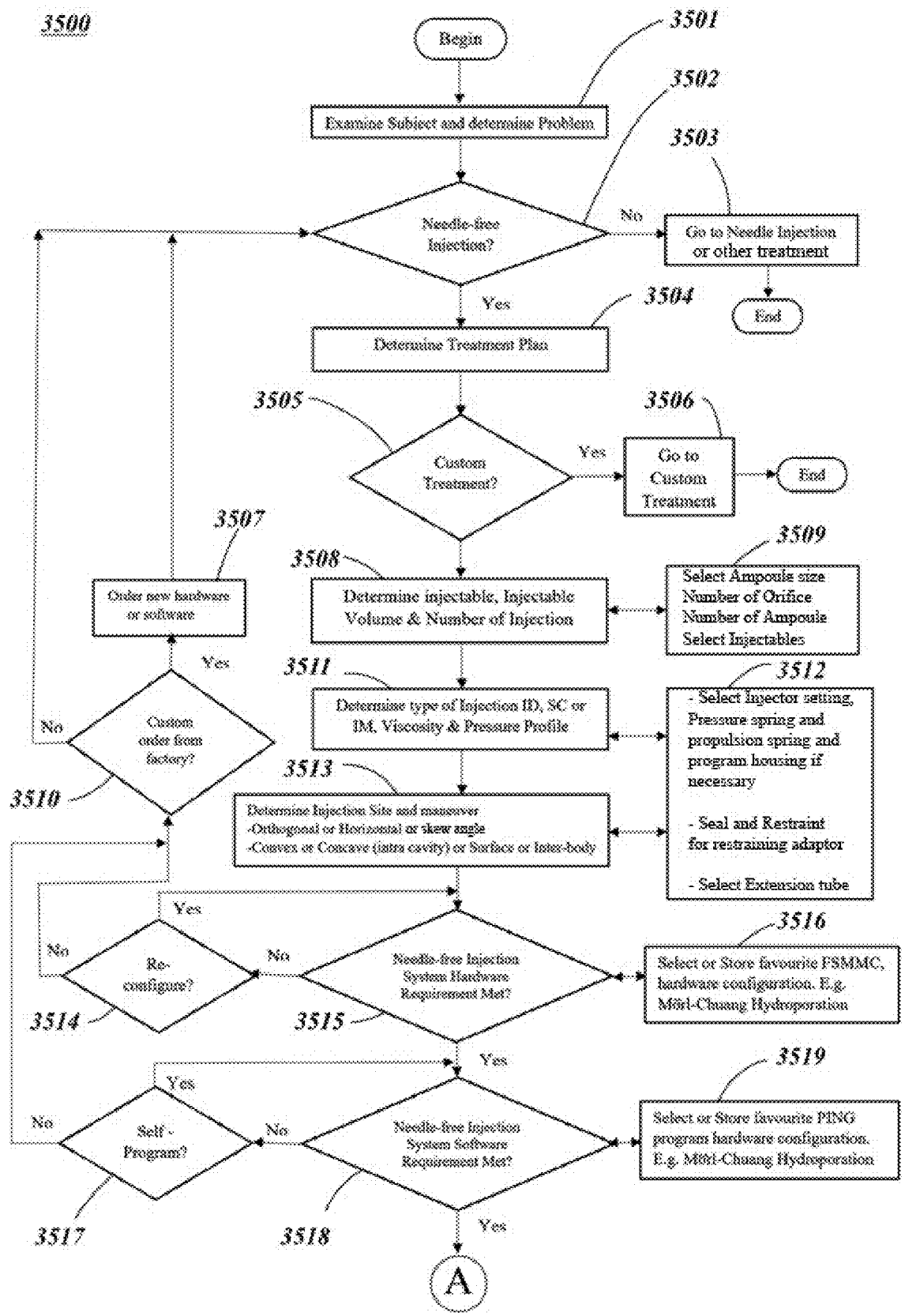
FIG. 35 depicts a flowchart comprising FIGS. 35A and 35B illustrating a process for treatment using the needle-free injector in accordance with the present embodiment.
Figure 35B:
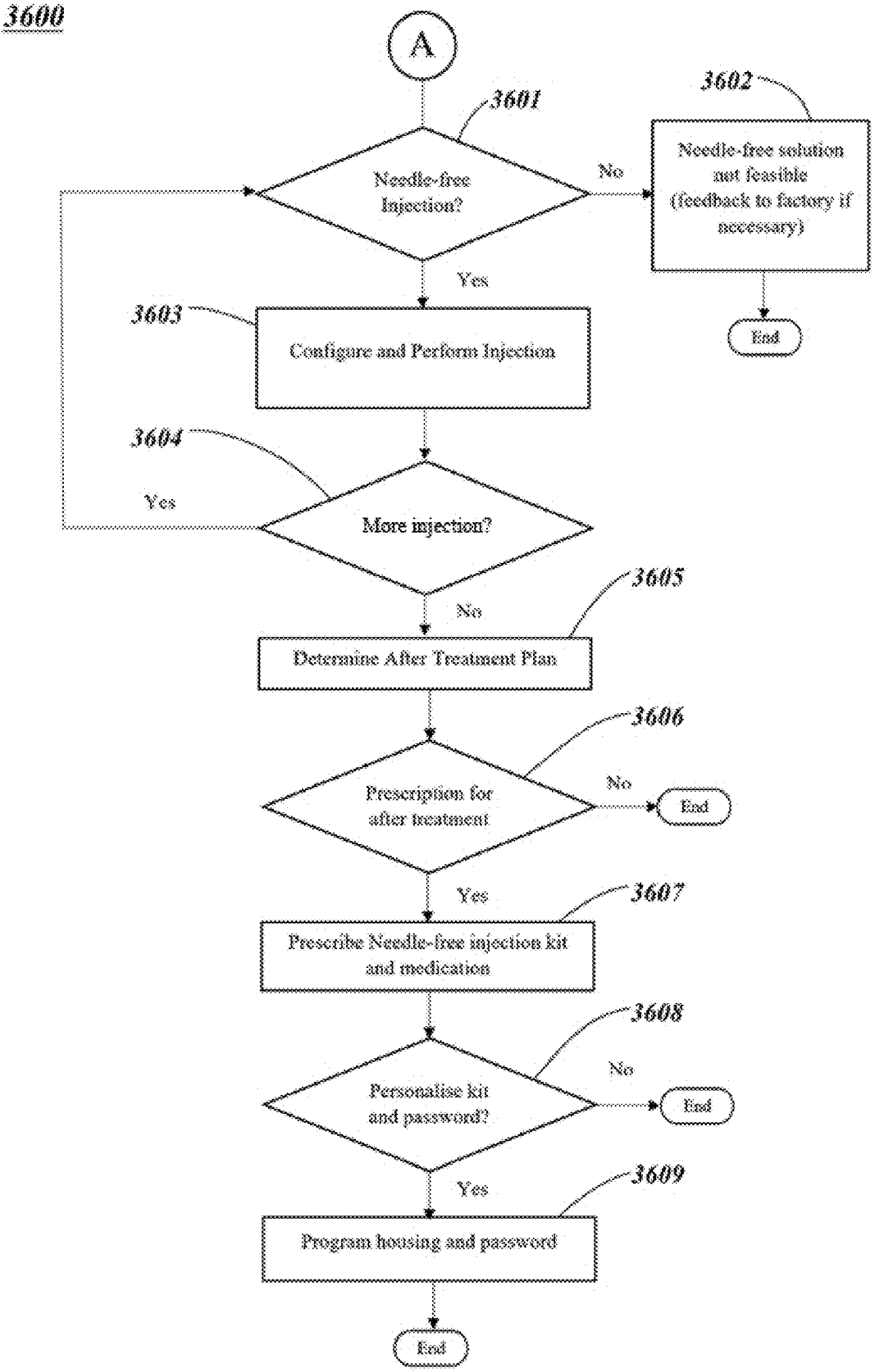

Referring to FIG. 35, a flowchart 3500, 3600 comprising FIGS. 35A and 35B depicts a process for medical treatment using the needle-free injector in accordance with the present embodiment. The method begins with examination of the subject to determine the problem 3501. The first evaluation is whether a needle-free injection is suitable 3502. If not, a needle injection or other medical procedure is considered 3503 and the flow in accordance with the present embodiment ends. If needle-free injection is suitable, a treatment plan has to be considered 3504. Does the treatment require a specialized custom treatment that cannot be handled by current methodology? If so, custom needle-free injection treatment planned and performed 3506 and the flow in accordance with the present embodiment ends. For regular needle-free injection treatment, the injectable(s) has to be determined, the injectable volume considered and the number of injections to be performed has to be decided 3508. This is done in conjunction with selection of needle-free hardware described hereinbefore. An ampoule size and ampoule type (prefilled ampoule modules or user filled types) and their numbers, with the appropriate number of orifices, to match one or more injectables to be hypodermically administered has to be determined 3509. Next, the type of injection, for instance intradermal, subcutaneous or intramuscular, is determined 3511 and whether fine depth tuning of these types of injections is needed, for instance, cascaded subcutaneous hydroporation injections at slightly varying depths as previously discussed. In the case of hydroporation or other specialized types of hypodermic procedure, whether or not to administer sequenced injectables or cocktails needs to be determined. This will provide viscosity parameters of the injectable or combination of injectables to determine the optimal propulsion pressure profiles and skin pressure profiles. With this information, the injector is selected, configured and/or programmed with the appropriate pressure spring and propulsion spring to correspond to these parameters 3512. If the practitioner is not familiar with such a selection process, information is available from the PING Replication System or on-line to guide the practitioner through such a selection process. At this point 3512, all other injection parameters and any new methodology or new factory upgrades, adaptors and accessories, and information released from time to time are considered before moving on further. Next, the injection site and maneuvers necessary to perform the injection are determined 3513, such as determining whether a standard orthogonal injection is enough, or a horizontal or skewed angle injection is necessary and whether the injection surface is convex, concave, intra-cavity or inter-body. Next, it is determined 3512 whether a standard seal is sufficient or whether the ampoules need to be configured with other types of seals or detachable seals, or new seals from the factory, if any. It is also determined 3512 if a restraining adaptor is necessary (and the appropriate restraint) and if an extension tube for a longer reach is required 3512. A maneuver for each of the injection sites must be planned.

After careful determination and selection, considerate is considered whether the needle-free injection system hardware requirements have been met 3515, and if a favorite combination of hardware has been previously concocted, for instance a Mori-Chuang hydroporation combination, which can be used. A new hardware combination can also be configured 3514 and if there is no suitable combination 3510, the process can be terminated 3503, or the factory using the PING Replicator System can be consulted to order new or replacement parts or custom parts 3507. Next, it is determined if the needle-free injection system software requirements have been met 3518 (i.e., has the appropriate surface pressure profile and propulsion spring profiles within the injector been met and/or is there is a need to program a new housing using PING). If the needle-free injection system software requirements have been met, either the requirements are self-programmed 3517 or custom-ordered from the factory using the PING Replicator System 3510. Alternatively, a user can store 3419 a favorite PING program with one or more settings (such as custom settings SC1, SC2 and SC3 for Mörl-Chuang hydroporation) and later select 3519 a housing already with a favorite PING program with one or more settings which is already stored. If the software requirements have been met, flow proceeds.

Next, a final check is performed to see if a feasible needle-free injection solution and all the safety interlocks and requirements are met, and that the injection is ready to be performed 3601. If there is a problem, the entire injection process can be aborted, feeding back to the factory or to a forum of similar-minded users if necessary. The aborted process ends here 3602. Otherwise, the injection is performed 3503, reconfiguring with each injection, if necessary. This is repeated until no more injections are needed 3604.

After completion of injections, it is determined if there is a need for an after treatment plan 3605 and if a prescription for after treatment is necessary 3606. With some medical treatment, such as insulin injections for diabetic patients, a homecare needle-free injection kit can be prescribed 3607. Professional and semi-professional kits can also be prescribed by hospitals, pharmacies and medical authorities for qualified doctors and nurses for independent use. The flow ends by deciding how the kitting out process is to be completed or personalized and whether a level of password is necessary 3609.

Alternative Embodiment of the Injector without the FSM

The FSMMC and PING provide advantageous effects and preferred operational functions in accordance with the present embodiment. Relocating the PING programs and maneuvering sprockets of the FSMMC to another position on the housing does not change the program's functionality. Removing the FSM and replacing each of the functionalities of the injector with an alternative implementation would require more parts but the behavior of the injector would nevertheless be the same. Thus, the automatic injecting needle free hypodermic injection apparatus, system and method in accordance with the present embodiment provide unique and novel advantages over conventional devices, system and methods for needle-free injection whether the FSM is implemented as part of the present embodiment or not. For the simplest of alternative embodiments, a safety cover is used to prevent the ampoule from being depressed. Removing the cover arms the injector. Replacing the cover puts the injector in a safe state. The bolt carrier travels unrestricted for the automatic injecting mechanism to fire. A way to prevent the bolt carrier from falling out is needed. A front housing cover secures the bolt carrier from the front. Alternatively, a rear housing part can be used to secure the bolt carrier from the rear.

Another alternative embodiment includes having the back of the bolt carrier extend out of the rear of the hollow tube during firing or have a minimal shortened hollow tube just covering the trigger. The view 1150 (FIG. 11) illustrates such an alternative embodiment. Anyone skilled in the art of mechanical design with the teachings provided in this description can easily design such alternatives.

Thus, it can be seen that the present embodiment can provide a close loop low latency mechanical pressure sensitive mechanism is used to automatically administer an injection with selectable settings. Any shape or design of the latch that allows a bi-directional movement of a pressure sensitive mechanism over the latch can be used without distracting from the purpose of the latch. Any shape or design of the latch that allows a pivoting point on the latch to be used with a separate pivot on another part also does not distract from the purpose of the latch. Further, any shape or design of the latch to be used with a zero or low latency pressure sensor with selectable firing positions does not distract from the purpose of the latch. Also, any shape or design of the latch to be used with an automatic pressure sensor for multiple firing positions does not distract from the purpose of the latch. In accordance with the present embodiment, one or more pre-determined surface pressure settings are used to provide one or more types of injection on the same injector. Also, one or more propulsion spring configurations can be provided in accordance with the present embodiment. These propulsion spring configurations include propulsion spring configurations for intradermal (ID), subcutaneous (SC) and intramuscular (IM) needle-free injections, for three subcutaneous injection settings, SC1, SC2 and SC3, for hydroporation applications, and different propulsion settings such as SP1 or SP2 for propulsion pressure type one and propulsion pressure type two or more. In accordance with the present embodiment, one or more predetermined surface pressure and propulsion pressure can be programmed into the injector without the need for electricity or pneumatics and these pressures, when used with the restraining adaptor for instance, is custom programmed for a particular corresponding medical procedure (e.g. hydroporation), so much so that when the medical procedure is performed with other jet injectors, the result is different or not achievable.

Description of FSMMC, PING and programs, and the PING Replicator System have been described as well as their accessories and their interrelationship to each other as a whole or in parts. The present embodiment includes the PING Replicator System as a means to produce the needle-free injector, its parts and accessories as described herein. In particular, the means to produce the injector, ampoules, FSMMC, PING and programs, and their accessories and their interrelationship to each other as a whole or in parts has been disclosed herein. That a whole or reduced version of the PING Replicator System can be distributed and applied in standalone application or in conjunction with other PING Replicator System and with every aspect of the present embodiment is also disclosed.

That the present embodiment when used intimately with medical procedures, actuating procedures or logical procedures is also embodied, with its parts and features as described herein is disclosed. Their alternatives are also disclosed and suggested.

Alternative embodiments and detailed description of aspects of the present embodiment are also described for the ampoule module, its parts and its features. Alternative embodiments and detailed description of these embodiments are also described for the injector, its parts and its features. In particular, FSMMC and PING and their parts and features and alternative embodiments of FSMMC and PING and the description of their parts and features are disclosed herein.

Numerous accessories for the systems and apparatuses disclosed herein are also embodied along with their parts and features as disclosed. A password key and its password sleeves, a restraining adaptor and its parts, two mechanical reloaders and an airlock adaptor are also presented and embodied within the present embodiment.

While exemplary embodiments have been presented in the foregoing detailed description, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing one or more exemplary embodiments of the invention, it being understood that various changes may be made in the function and arrangement of steps and method of operation described in the exemplary embodiment without departing from the scope of the invention as set forth in the appended claims.

What is claimed is:

1. A safety-enhanced needle-free injector system comprising:
    a housing;
    a bolt carrier with one or more springs held at a first end and having a firing chamber formed therein from the one or more springs to an opening at a second end opposite the first end, wherein the bolt carrier further includes a spring-driven member coupled to the one or more springs and located in the firing chamber;
    an ampoule coupleable to the bolt carrier, the ampoule having a compartment for storing an injectable for needle-free delivery and a seal for driving the injectable out an opening at a first end of the ampoule, wherein a plunger couples between the spring-driven member and the seal when a second end of the ampoule opposite the first end of the ampoule is coupled to the bolt carrier to allow the spring-driven member to engage the seal for driving the injectable along a length of the ampoule from the second end of the ampoule to the first end of the ampoule and out the opening at the first end of the ampoule, the opening at the first end of the ampoule comprising one or more orifices;
    a user-sensible safety mechanism having safety cues for providing safety-enhanced needle-free injection of the injectable, the safety cues comprising a pressure-sensed, tactile-sensed or visual-sensed mechanism, said pressure-sensed, tactile-sensed of visual-sensed mechanism including a protruding ring positioned within the housing, said protruding ring selectably positioned within the housing to prevent inadvertent user activation of the needle-free injector system; and
    a textured pattern positioned within an inner surface of the housing, said textured pattern configured to set a state of the needle-free injector system to one or more predetermined states in response to one or more predefined movements of one of the housing, the bolt carrier and the ampoule relative to one another corresponding to one or more finite state machine mechanical computer (FSMMC) programmed instructions.

2. The needle-free injector system in accordance with claim 1, wherein the one or more FSMMC programmed instructions comprise a FSMMC programmed instruction to set the state of the needle-free injector system to a state which inhibits further use of the needle-free injector system in response to a number of uses of the needle-free injector system.

3. The needle-free injector system in accordance with claim 1, wherein the one or more FSMMC programmed instructions comprise a FSMMC programmed instruction to set the state of the needle-free injector system to a lock state which prevents further use of the needle free injector system and/or a FSMMC programmed instruction to set the state of the needle-free injector system to an unlock state for reuse or recycling.

4. The needle-free injector system in accordance with claim 3, wherein the FSMMC programmed instruction to set the state of the needle-free injector system to the lock state comprises entry of an incorrect password.

5. The needle-free injector system in accordance with claim 1, wherein the one or more FSMMC programmed instructions comprise an injection pressure FSMMC instruction to determine an injectable delivery pressure wherein the bolt carrier when arming the one or more springs is configured to compress the one or more springs a distance determined in response to the injection pressure FSMMC instruction.

6. The needle-free injector system in accordance with claim 5, wherein the injection pressure FSMMC instruction is operable in response to coupling the ampoule to the bolt carrier providing a FSMMC input corresponding to a type of injectable and/or a type of injection.

* * * * *